US012575612B2

(12) United States Patent
Raichman

(10) Patent No.: US 12,575,612 B2
(45) Date of Patent: Mar. 17, 2026

(54) SMOKING DEVICE WITH FLATTENING FUNCTION

(71) Applicant: N2B LIMITED, Limassol (CY)

(72) Inventor: Yossef Raichman, Limassol (CY)

(73) Assignee: N2B LIMITED, Limassol (CY)

( * ) Notice: Subject to any disclaimer, the term of this patent is extended or adjusted under 35 U.S.C. 154(b) by 397 days.

(21) Appl. No.: 18/314,325

(22) Filed: May 9, 2023

(65) Prior Publication Data

US 2024/0245116 A1     Jul. 25, 2024

Related U.S. Application Data

(63) Continuation of application No. PCT/IB2023/052521, filed on Mar. 15, 2023.

(Continued)

(51) Int. Cl.
*A24F 47/00*          (2020.01)
*A24D 1/02*          (2006.01)
(Continued)

(52) U.S. Cl.
CPC ............... *A24F 40/57* (2020.01); *A24D 1/02* (2013.01); *A24D 1/20* (2020.01); *A24F 40/20* (2020.01); *A24F 40/42* (2020.01); *A24F 40/46* (2020.01); *A24F 40/465* (2020.01); *A24F 40/50* (2020.01); *A24F 40/51* (2020.01); *A24F 40/53* (2020.01); *A24F 40/60* (2020.01); *G01J 5/0014* (2013.01); *G01K 1/026* (2013.01); *G01K 3/02* (2013.01); *G01K 7/02* (2013.01); *H05B 1/023* (2013.01);
(Continued)

(58) Field of Classification Search
CPC ......... A24F 40/20; A24F 40/40; A24F 40/465
See application file for complete search history.

(56) References Cited

U.S. PATENT DOCUMENTS 818,150 A     4/1906   Du Brul
4,184,495 A     1/1980   Rainer et al.
(Continued)

FOREIGN PATENT DOCUMENTS

CA           3208054 A1     8/2022
CN         203012511 U     6/2013
(Continued)

OTHER PUBLICATIONS

International Search Report and Written Opinion from International Application No. PCT/IB2023/052518 mailed Oct. 19, 2023.
(Continued)

*Primary Examiner* — Eric Yaary
(74) *Attorney, Agent, or Firm* — Ballard Spahr LLP

(57) ABSTRACT

Apparatus and methods are provided for use with a cylindrically-shaped capsule that contains a smoking material containing one or more active agents. A smoking device receives the cylindrically-shaped capsule that contains the smoking material and flattens at least part of a portion of the capsule that contains the smoking material. The smoking device vaporizes one or more of the active agents from within the smoking material by heating the smoking material while at least part of the portion of the capsule that contains the smoking material is in a flattened configuration. Other applications are also described.

18 Claims, 43 Drawing Sheets

Related U.S. Application Data

(60) Provisional application No. 63/438,643, filed on Jan. 12, 2023.

(51) Int. Cl.

| | |
|---|---|
| *A24D 1/20* | (2020.01) |
| *A24F 40/20* | (2020.01) |
| *A24F 40/42* | (2020.01) |
| *A24F 40/46* | (2020.01) |
| *A24F 40/465* | (2020.01) |
| *A24F 40/50* | (2020.01) |
| *A24F 40/51* | (2020.01) |
| *A24F 40/53* | (2020.01) |
| *A24F 40/57* | (2020.01) |
| *A24F 40/60* | (2020.01) |
| *G01J 5/00* | (2022.01) |
| *G01K 1/02* | (2021.01) |
| *G01K 3/02* | (2006.01) |
| *G01K 7/02* | (2021.01) |
| *H05B 1/02* | (2006.01) |
| *H05B 3/00* | (2006.01) |
| *H05B 6/10* | (2006.01) |
| *A61M 11/04* | (2006.01) |
| *A61M 15/00* | (2006.01) |
| *A61M 15/06* | (2006.01) |
| *H05B 6/36* | (2006.01) |

(52) U.S. Cl.
CPC ......... *H05B 1/0252* (2013.01); *H05B 3/0004* (2013.01); *H05B 3/0014* (2013.01); *H05B 6/105* (2013.01); *A61M 11/042* (2014.02); *A61M 15/003* (2014.02); *A61M 15/06* (2013.01); *H05B 6/36* (2013.01)

(56) References Cited

U.S. PATENT DOCUMENTS

| | | | |
|---|---|---|---|
| 4,928,714 | A | 5/1990 | Shannon |
| 5,144,962 | A | 9/1992 | Counts et al. |
| 5,379,789 | A | 1/1995 | Schneider et al. |
| 10,179,215 | B2 | 1/2019 | Raichman |
| 10,542,776 | B2 | 1/2020 | Lavanchy et al. |
| 10,721,967 | B2 | 7/2020 | Raichman |
| 10,765,821 | B2 | 9/2020 | Raichman |
| 11,058,834 | B2 | 7/2021 | Raichman |
| 11,058,835 | B2 | 7/2021 | Raichman |
| 11,076,642 | B1 | 8/2021 | Fuisz et al. |
| 11,382,356 | B2 | 7/2022 | Worm et al. |
| 11,478,016 | B2 | 10/2022 | John et al. |
| 11,696,599 | B2 | 7/2023 | Raichman |
| 11,696,989 | B2 | 7/2023 | Raichman |
| 2008/0092912 | A1 | 4/2008 | Robinson et al. |
| 2011/0126848 | A1 | 6/2011 | Zuber et al. |
| 2013/0143468 | A1 | 6/2013 | Raichman et al. |
| 2014/0083438 | A1 | 3/2014 | Sebastian et al. |
| 2014/0301721 | A1 | 10/2014 | Ruscio et al. |
| 2014/0305449 | A1 | 10/2014 | Plojoux et al. |
| 2015/0083150 | A1 | 3/2015 | Conner et al. |
| 2015/0111059 | A1 | 4/2015 | Tanaka et al. |
| 2015/0157052 | A1 | 6/2015 | Ademe et al. |
| 2015/0257443 | A1 | 9/2015 | Rado |
| 2016/0271347 | A1 | 9/2016 | Raichman |
| 2016/0309779 | A1 | 10/2016 | Liu |
| 2017/0018863 | A1 | 1/2017 | Gao et al. |
| 2017/0055580 | A1 | 3/2017 | Blandino et al. |
| 2017/0055581 | A1 | 3/2017 | Wilke et al. |
| 2017/0119048 | A1 | 5/2017 | Kaufman et al. |
| 2017/0119049 | A1 | 5/2017 | Blandino et al. |
| 2017/0188632 | A1 | 7/2017 | Hon |
| 2017/0314094 | A1 | 11/2017 | Ooyama et al. |
| 2017/0360092 | A1 | 12/2017 | Althorpe et al. |
| 2017/0367407 | A1 | 12/2017 | Althorpe et al. |
| 2018/0104214 | A1 | 4/2018 | Raichman |
| 2018/0110943 | A1 | 4/2018 | Raichman |
| 2018/0168224 | A1 | 6/2018 | Naughton et al. |
| 2018/0235279 | A1 | 8/2018 | Wilke et al. |
| 2018/0271147 | A1* | 9/2018 | Rado ..................... A24F 40/46 |
| 2019/0000133 | A1 | 1/2019 | Park et al. |
| 2019/0008208 | A1 | 1/2019 | Cirillo et al. |
| 2019/0037924 | A1 | 2/2019 | Habicht et al. |
| 2019/0098927 | A1 | 4/2019 | Mironov |
| 2019/0117915 | A1 | 4/2019 | Raichman |
| 2019/0208823 | A1 | 7/2019 | Raichman |
| 2019/0224430 | A1 | 7/2019 | Raichman |
| 2019/0261684 | A1 | 8/2019 | Reevell |
| 2019/0289908 | A1 | 9/2019 | Worm et al. |
| 2019/0380390 | A1 | 12/2019 | Jeong et al. |
| 2019/0387806 | A1 | 12/2019 | Nakano et al. |
| 2020/0037669 | A1 | 2/2020 | Bowen et al. |
| 2020/0046023 | A1 | 2/2020 | Reevell |
| 2020/0093181 | A1 | 3/2020 | Hubbard et al. |
| 2020/0093185 | A1* | 3/2020 | Lim ........................ A24F 40/53 |
| 2020/0154784 | A1 | 5/2020 | Sebastian et al. |
| 2020/0179625 | A1 | 6/2020 | Raichman |
| 2020/0187556 | A1 | 6/2020 | Raichman |
| 2020/0187563 | A1 | 6/2020 | Raichman |
| 2020/0188614 | A1 | 6/2020 | Raichman |
| 2020/0221782 | A1 | 7/2020 | Lim |
| 2020/0236998 | A1* | 7/2020 | Batista .................. A24F 40/465 |
| 2020/0237004 | A1 | 7/2020 | Larsen |
| 2020/0238027 | A1 | 7/2020 | Raichman |
| 2020/0245683 | A1 | 8/2020 | Batista et al. |
| 2020/0246563 | A1 | 8/2020 | Raichman |
| 2021/0015153 | A1 | 1/2021 | Raichman |
| 2021/0178090 | A1 | 6/2021 | Lahoud et al. |
| 2021/0235747 | A1 | 8/2021 | Iwanaga et al. |
| 2021/0244082 | A9 | 8/2021 | Monsees et al. |
| 2021/0289841 | A1 | 9/2021 | Batista et al. |
| 2021/0322688 | A1 | 10/2021 | Raichman |
| 2022/0110368 | A1 | 4/2022 | Jang et al. |
| 2022/0143338 | A1 | 5/2022 | Davidson et al. |
| 2022/0167663 | A1 | 6/2022 | Paton et al. |
| 2022/0183394 | A1 | 6/2022 | Halliday et al. |
| 2022/0218023 | A1 | 7/2022 | Fuisz et al. |
| 2022/0279838 | A1 | 9/2022 | Graf et al. |
| 2022/0369705 | A1 | 11/2022 | Besso et al. |
| 2023/0018415 | A1 | 1/2023 | Abi Aoun et al. |
| 2023/0058955 | A1 | 2/2023 | Selby et al. |
| 2023/0107605 | A1 | 4/2023 | Tasselli |
| 2023/0114383 | A1 | 4/2023 | Jiang et al. |
| 2023/0346019 | A1 | 11/2023 | Saygili |
| 2024/0099391 | A1 | 3/2024 | Parry et al. |
| 2024/0237701 | A1 | 7/2024 | Raichman |
| 2024/0237703 | A1 | 7/2024 | Raichman |
| 2024/0237704 | A1 | 7/2024 | Raichman |
| 2024/0237705 | A1 | 7/2024 | Raichman |
| 2024/0237707 | A1 | 7/2024 | Raichman |
| 2024/0237708 | A1 | 7/2024 | Raichman |
| 2024/0237709 | A1 | 7/2024 | Raichman |
| 2024/0237714 | A1 | 7/2024 | Raichman |
| 2024/0237720 | A1 | 7/2024 | Raichman |
| 2024/0237721 | A1 | 7/2024 | Raichman |
| 2024/0237722 | A1 | 7/2024 | Raichman |
| 2024/0237723 | A1 | 7/2024 | Raichman |
| 2024/0237724 | A1 | 7/2024 | Raichman |
| 2024/0237725 | A1 | 7/2024 | Raichman |
| 2024/0237726 | A1 | 7/2024 | Raichman |
| 2024/0237737 | A1 | 7/2024 | Raichman |
| 2024/0237738 | A1 | 7/2024 | Raichman |
| 2024/0237739 | A1 | 7/2024 | Raichman |
| 2024/0237740 | A1 | 7/2024 | Raichman |
| 2024/0237741 | A1 | 7/2024 | Raichman |
| 2024/0237742 | A1 | 7/2024 | Raichman |
| 2024/0237743 | A1 | 7/2024 | Raichman |
| 2024/0237751 | A1 | 7/2024 | Raichman |
| 2024/0237753 | A1 | 7/2024 | Raichman |
| 2024/0237754 | A1 | 7/2024 | Raichman |
| 2024/0237758 | A1 | 7/2024 | Raichman |
| 2024/0237759 | A1 | 7/2024 | Raichman |
| 2024/0237760 | A1 | 7/2024 | Raichman |

(56) References Cited

U.S. PATENT DOCUMENTS

| | | | |
|---|---|---|---|
| 2025/0000168 A1 | 1/2025 | Bessant et al. |
| 2025/0057249 A1 | 2/2025 | Murray et al. |
| 2025/0176625 A1 | 6/2025 | Monticone et al. |

FOREIGN PATENT DOCUMENTS

| | | |
|---|---|---|
| DE | 102018207126 A1 | 6/2018 |
| EP | 0305788 A1 | 3/1989 |
| EP | 3610743 A2 | 2/2020 |
| EP | 3925461 A1 | 12/2021 |
| EP | 3957196 A1 | 2/2022 |
| EP | 3984387 A1 | 4/2022 |
| EP | 4091486 A1 | 11/2022 |
| GB | 2069310 A | 8/1981 |
| GB | 2534208 A | 7/2016 |
| KR | 101345117 B1 | 12/2013 |
| KR | 20190049389 A | 5/2019 |
| WO | 2016147188 A1 | 9/2016 |
| WO | 2018051346 A1 | 3/2018 |
| WO | 2018141467 A1 | 8/2018 |
| WO | 2019005526 A1 | 1/2019 |
| WO | 2019030168 A1 | 2/2019 |
| WO | 2019073237 A1 | 4/2019 |
| WO | 2019101623 A1 | 5/2019 |
| WO | 2020070109 A1 | 4/2020 |
| WO | 2020074744 A1 | 4/2020 |
| WO | 2020182772 A1 | 9/2020 |
| WO | 2020211315 A1 | 10/2020 |
| WO | 2021171180 A1 | 9/2021 |
| WO | 2022155175 A1 | 7/2022 |
| WO | 2022189452 A1 | 9/2022 |
| WO | 2023170182 A1 | 9/2023 |
| WO | 2024150033 A1 | 7/2024 |
| WO | 2024150034 A1 | 7/2024 |
| WO | 2024150035 A1 | 7/2024 |
| WO | 2024150036 A1 | 7/2024 |
| WO | 2024150037 A1 | 7/2024 |
| WO | 2024150038 A1 | 7/2024 |
| WO | 2024150183 A1 | 7/2024 |

OTHER PUBLICATIONS

International Search Report and Written Opinion from International Application No. PCT/IB2023/052519 mailed Oct. 18, 2023.
International Search Report and Written Opinion from International Application No. PCT/IB2023/052520 mailed Oct. 18, 2023.
International Search Report and Written Opinion from International Application No. PCT/IB2023/052521 mailed Dec. 12, 2023.
International Search Report and Written Opinion from International Application No. PCT/IB2023/052523 mailed Oct. 18, 2023.
International Search Report and Written Opinion from International Application No. PCT/IB2023/052526 mailed Dec. 11, 2023.
International Search Report and Written Opinion from International Application No. PCT/IB2024/050322 mailed Jun. 4, 2024.
Invitation to Pay Additional Fees for International Application No. PCT/IB2023/052521 mailed Oct. 19, 2023.
Invitation to Pay Additional Fees for International Application No. PCT/IB2023/052526 mailed Oct. 19, 2023.
Invitation to Pay Additional Fees for International Application No. PCT/IB2024/050322 mailed Apr. 12, 2024.
Notice of Allowance from U.S. Appl. No. 16/851,804 mailed Jul. 25, 2022.
U.S. Appl. No. 18/211,849, filed Jun. 20, 2023.
U.S. Appl. No. 18/314,265, filed May 9, 2023.
U.S. Appl. No. 18/314,269, filed May 9, 2023.
U.S. Appl. No. 18/314,271, filed May 9, 2023.
U.S. Appl. No. 18/314,274, filed May 9, 2023.
U.S. Appl. No. 18/314,314, filed May 9, 2023.
U.S. Appl. No. 18/314,316, filed May 9, 2023.
U.S. Appl. No. 18/315,052, filed May 10, 2023.
U.S. Appl. No. 18/315,059, filed May 10, 2023.
U.S. Appl. No. 18/315,063, filed May 10, 2023.
U.S. Appl. No. 18/315,068, filed May 10, 2023.
U.S. Appl. No. 18/315,073, filed May 10, 2023.
U.S. Appl. No. 18/315,697, filed May 11, 2023.
U.S. Appl. No. 18/315,700, filed May 11, 2023.
U.S. Appl. No. 18/315,702, filed May 11, 2023.
U.S. Appl. No. 18/315,704, filed May 11, 2023.
U.S. Appl. No. 63/457,182, filed Apr. 5, 2023.
U.S. Appl. No. 63/463,117, filed May 1, 2023.
U.S. Appl. No. 63/468,418, filed May 23, 2023.
U.S. Appl. No. 63/521,685, filed Jun. 18, 2023.
U.S. Appl. No. 63/522,303, filed Jun. 21, 2023.
U.S. Appl. No. 63/524,736, filed Jul. 3, 2023.
U.S. Appl. No. 63/531,667, filed Jul. 9, 2023.
Written Opinion from International Application No. PCT/IB2022/012084 mailed May 23, 2022.
U.S. Appl. No. 18/303,623, filed Apr. 20, 2023.
U.S. Appl. No. 18/303,624, filed Apr. 20, 2023.
U.S. Appl. No. 18/303,627, filed Apr. 20, 2023.
U.S. Appl. No. 18/303,629, filed Apr. 20, 2023.
U.S. Appl. No. 18/303,633, filed Apr. 20, 2023.
U.S. Appl. No. 18/303,636, filed Apr. 20, 2023.
U.S. Appl. No. 18/307,516, filed Apr. 26, 2023.
U.S. Appl. No. 18/307,524, filed Apr. 26, 2023.
U.S. Appl. No. 18/307,534, filed Apr. 26, 2023.
U.S. Appl. No. 18/308,162, filed Apr. 27, 2023.
U.S. Appl. No. 18/308,170, filed Apr. 27, 2023.
U.S. Appl. No. 18/308,173, filed Apr. 27, 2023.
U.S. Appl. No. 18/312,058, filed May 4, 2023.
U.S. Appl. No. 18/312,061, filed May 4, 2023.
U.S. Appl. No. 18/312,063, filed May 4, 2023.
U.S. Appl. No. 18/312,066, filed May 4, 2023.
U.S. Appl. No. 18/312,070, filed May 4, 2023.
U.S. Appl. No. 63/438,643, filed Jan. 12, 2023.
Dr. Dabber Knowledge Base, "Switch User Manual" https://drdabber.helpscoutdocs.com/article/76-switch-user-manual, Jan. 27, 2023.
Non-Final Office Action for U.S. Appl. No. 18/303,623 mailed Nov. 14, 2025.
Non-Final Office Action for U.S. Appl. No. 18/303,627 mailed Sep. 3, 2025.
Non-Final Office Action for U.S. Appl. No. 18/303,636 mailed Nov. 4, 2025.
Non-Final Office Action for U.S. Appl. No. 18/307,516 mailed Oct. 2, 2025.
Non-Final Office Action for U.S. Appl. No. 18/307,524 mailed Sep. 17, 2025.
Non-Final Office Action for U.S. Appl. No. 18/307,534 mailed Jul. 22, 2025.
Non-Final Office Action for U.S. Appl. No. 18/308,162 mailed Aug. 14, 2025.
Non-Final Office Action for U.S. Appl. No. 18/308,170 mailed Aug. 11, 2025.
Non-Final Office Action for U.S. Appl. No. 18/308,173 mailed Oct. 2, 2025.
Non-Final Office Action for U.S. Appl. No. 18/312,058 mailed Oct. 2, 2025.
Non-Final Office Action for U.S. Appl. No. 18/312,061 mailed Aug. 5, 2025.
Non-Final Office Action for U.S. Appl. No. 18/312,063 mailed Sep. 11, 2025.
Non-Final Office Action for U.S. Appl. No. 18/312,066 mailed Sep. 17, 2025.
Non-Final Office Action for U.S. Appl. No. 18/312,070 mailed Jul. 25, 2025.
Non-Final Office Action for U.S. Appl. No. 18/314,265 mailed Nov. 3, 2025.
Non-Final Office Action for U.S. Appl. No. 18/314,314 mailed Aug. 8, 2025.
Non-Final Office Action for U.S. Appl. No. 18/314,316 mailed Aug. 1, 2025.
Non-Final Office Action for U.S. Appl. No. 18/314,321 mailed Sep. 16, 2025.

(56)  References Cited

OTHER PUBLICATIONS

Non-Final Office Action for U.S. Appl. No. 18/315,052 mailed Aug. 8, 2025.
Non-Final Office Action for U.S. Appl. No. 18/315,059 mailed Sep. 23, 2025.
Non-Final Office Action for U.S. Appl. No. 18/315,068 mailed Oct. 1, 2025.
Non-Final Office Action for U.S. Appl. No. 18/315,073 mailed Nov. 6, 2025.
Non-Final Office Action for U.S. Appl. No. 18/315,697 mailed Aug. 12, 2025.
Non-Final Office Action for U.S. Appl. No. 18/315,700 mailed Aug. 4, 2025.
Non-Final Office Action for U.S. Appl. No. 18/315,702 mailed Sep. 17, 2025.
Notice of Allowance for U.S. Appl. No. 18/303,629 mailed Sep. 16, 2025.
Restriction Requirement for U.S. Appl. No. 18/303,623 mailed Aug. 4, 2025.
Restriction Requirement for U.S. Appl. No. 18/303,624 mailed Aug. 13, 2025.
Restriction Requirement for U.S. Appl. No. 18/303,633 mailed Aug. 27, 2025.
Restriction Requirement for U.S. Appl. No. 18/303,636 mailed Aug. 4, 2025.
Restriction Requirement for U.S. Appl. No. 18/314,265 mailed Aug. 11, 2025.
Restriction Requirement for U.S. Appl. No. 18/314,271 mailed Oct. 3, 2025.
Restriction Requirement for U.S. Appl. No. 18/315,704 mailed Sep. 16, 2025.
U.S. Appl. No. 18/314,321, filed May 9, 2023.
U.S. Appl. No. 18/349,477, filed Jul. 10, 2023.
U.S. Appl. No. 63/602,545, filed Nov. 24, 2023 .

* cited by examiner

FIG. 18A
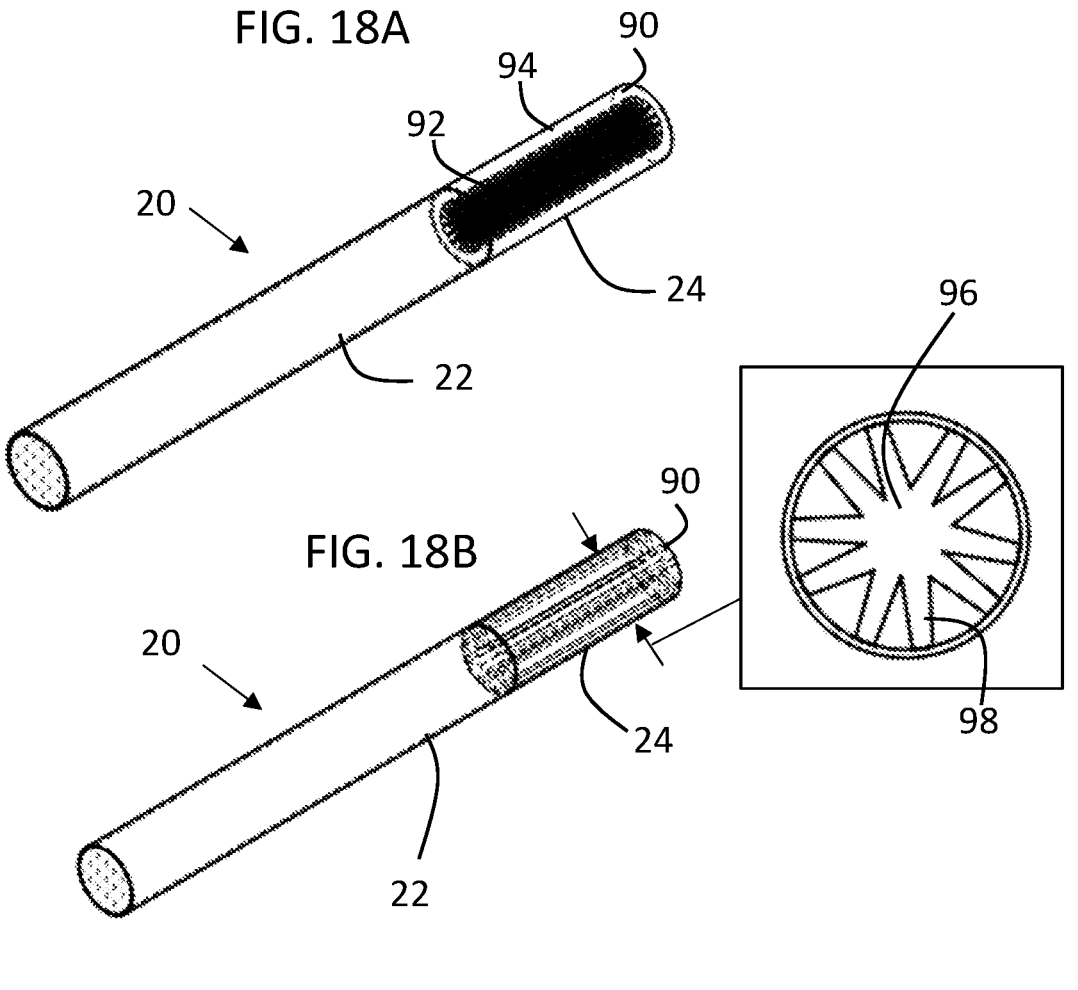
FIG. 18B
FIG. 18C
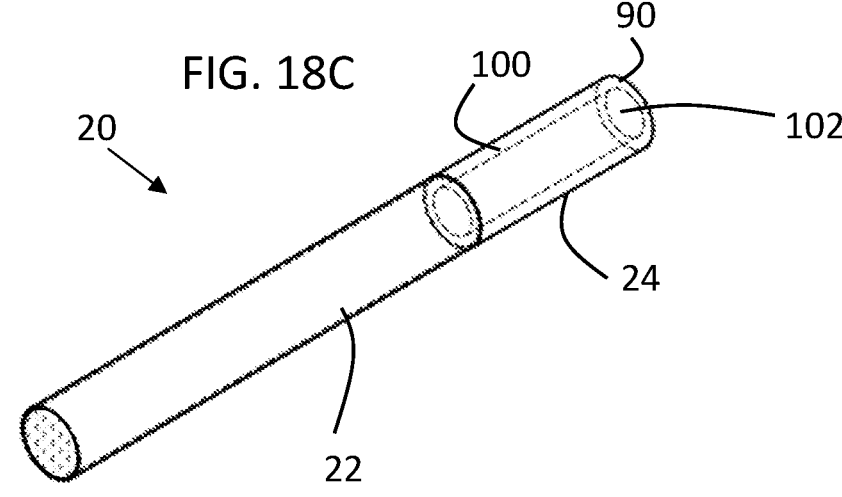

240     242     20

20

242

240

SMOKING DEVICE WITH FLATTENING FUNCTION

CROSS-REFERENCES TO RELATED APPLICATIONS

The present application is a continuation of PCT/IB2023/052521 to Raichman, filed Mar. 15, 2023, entitled "Smoking device with flattening function," which claims priority from U.S. Provisional Patent Application 63/438,643 to Raichman, filed Jan. 12, 2023, entitled "Smoking device and capsule for use therewith," which is incorporated herein by reference.

FIELD OF EMBODIMENTS OF THE INVENTION

The present invention relates to methods and apparatus relating to smoking devices, and particularly apparatus and methods relating to heat-not-burn smoking devices.

BACKGROUND

Heat-not-burn smoking devices (also known as "smokeless" devices) are devices that heat a smoking material that contains active agents (e.g., a plant material, such as tobacco and/or a cannabinoid-containing plant material (such as marijuana), or a non-plant material) without burning the smoking material. The user sucks in vaporized active agents that are generated. Such devices have become popular in recent years, and in particular some users who previously smoked traditional cigarettes have switched to using such products.

SUMMARY OF EMBODIMENTS

In accordance with some applications of the present invention, a capsule is configured to be inserted in a smoking device. Typically, the capsule is a disposable capsule that is configured to be used during a single smoking session, whereas the smoking device is configured to be reusable. The capsule typically has the general structure (e.g., shape and size) of a traditional cigarette. Many users and manufacturers of such capsule and smoking devices have a preference for single-use capsules having the general structure of a traditional cigarette, due to (a) habitual preferences of the users, (b) habitual preferences of the manufacturers, (c) production lines of the manufacturers being best-equipped to manufacture such capsules relative to capsules that differ from traditional cigarettes, (d) single-use capsules being more hygienic than capsules that are designed for repeated use, and/or (e) additional reasons.

Typically, the capsule includes a first portion that contains a smoking material (that contains active agents) and a heating element. The smoking material is typically a plant material, such as tobacco and/or a cannabinoid-containing plant material (such as marijuana). For some applications, the smoking material is a non-plant material that contains active agents. The smoking device is configured to heat the smoking material, such as to generate vapors containing active agents within the smoking material in a heat-not-burn manner. The user typically sucks the generated vapors out of a second portion of the capsule that functions as a mouthpiece.

As described hereinabove in the Background, heat-not-burn smoking devices (also known as "smokeless" devices) are devices that heat a smoking material without burning (i.e., pyrolyzing) the smoking material. The user sucks in vaporized active agents that are generated. An important element in heat-not-burn smoking devices is the time that it takes to heat the smoking material and the uniformity of the heating. The time that it takes to heat up the smoking material is defined by the following equation:

$$t = Q * d / (K * A * \Delta T) \qquad \text{[Equation 1]}$$

where
t is the time taken to heat the smoking material,
Q is the quantity of heat transferred to the smoking material,
d is the distance from the location at which the heat is generated to the smoking material that is being heated,
K is the constant that defines the heat conduction of the smoking material (which is relatively low for smoking materials as they are relatively non-conductive), and any other material between the heating element and the smoking material,
A is the area of contact between the heating element and the smoking material, and
T is temperature change that is applied at the heating element.

There are several challenges to heating up smoking material in a heat-not-burn process, including the following:
low heat conduction of the smoking material (i.e., a low value of K in Equation 1);
a limited temperature to which the heating element can be heated in order to avoid pyrolysis (i.e., burning) of the smoking material (i.e., a low value of AT in Equation 1);
many designs of heating-elements-capsule combinations providing a relatively small area of contact between the heating elements and the smoking material (i.e., a low value of A in Equation 1), particularly if the capsule is designed to have the general shape of a traditional cigarette;
in order to provide the appearance and feel of a traditional cigarette, there may be a heat-insulating material (e.g., paper) between the heating element and the smoking material (thereby further decreasing K in Equation 1), for example, if heating is applied by a heating element that is disposed within the smoking device outside the capsule;
the distance from the heating element to the smoking material that is located toward the radial center of the capsule is relatively large (i.e., a high value of d in Equation 1).

In accordance with some applications of the present invention, apparatus and methods are provided that (a) provide a relatively large area of contact between the heating element and the smoking material (i.e., A in Equation 1), and (b) provide a relatively small distance between the heating element and the smoking material even at the radial center of the capsule (i.e., d in Equation 1), while (c) providing the user with a capsule having the same general structure as a traditional cigarette.

Typically, the heating element is built-in to the capsule, such that it is in direct contact with smoking material. For some applications, at least some of the heating element is embedded within the smoking material, as described in further detail hereinbelow. For some applications, the heating element comprises a metal material (such as metallic foil, e.g., stainless steel foil, nickel-titanium foil, titanium foil, copper foil, aluminum foil, steel foil), which is typically disposed within the capsule and/or is typically in direct contact with the smoking material, and that is heated via electrical resistive heating, as described in further detail hereinbelow. Alternatively or additionally, the heating element comprises one or more magnetically-heated materials that are susceptible to being heated by a magnetic field (such as, magnetic materials and/or ferromagnetic materials), which are typically disposed within the capsule and/or are typically in direct contact with smoking material and that are heated via magnetic induction, as described in further detail hereinbelow.

Typically, the capsule is an elongate capsule. For some applications, the capsule has a length of between 15 mm and 150 mm (e.g., between 50 mm and 90 mm). For some applications, the capsule has the same general structure as a traditional cigarette, but differs from the general structure of a cigarette in that the capsule is provided to the user with at least a portion of the capsule having a shape that is flattened relative to a traditional cigarette (e.g., such that it has an elliptical, rectangular, pill-shaped, or racetrack-shaped cross-sectional shape). Typically, by being flattened, the smoking material that is disposed toward the radial center of the capsule is disposed closer to the heating element than if the capsule had a circular cross section with a similar cross-sectional area, as described in further detail hereinbelow. Alternatively, the capsule is provided to the user with a circular cross-section shape, typically having a diameter of between 4 mm and 12 mm (e.g., between 5 and 8.5 mm). Typically, for such applications, although the capsule is provided to the user with the capsule having a circular cross-sectional shape, at least a portion of the capsule is flattened upon being inserted into the smoking device (e.g., such that it has an elliptical, rectangular, pill-shaped, or racetrack-shaped cross-sectional shape), such that the smoking material that was disposed toward the radial center of the capsule is disposed closer to the heating element than it would have been before being flattened, as described in further detail hereinbelow.

For some applications, the smoking device includes two or more electrodes that are configured (a) to heat a heating element that is disposed within the capsule via electrical resistive heating, and (b) to apply mechanical pressure to the capsule in order to flatten all or part of the portion of the capsule that contains the smoking material.

There is therefore provided, in accordance with some applications of the present invention, apparatus for use with a smoking device, the apparatus including:
    a capsule including:
        a smoking material containing one or more active agents; and
        one or more heating elements disposed within the capsule, the one or more heating elements being configured to vaporize one or more of the active agents from within the smoking material, by the one or more heating elements being heated by the smoking device,
        at least a portion of the capsule being configured to be flattened by the smoking device prior to the one or more heating elements being heated by the smoking device.

In some applications, the capsule has a circular cross-sectional shape and is configured to be flattened to define a non-circular cross-sectional shape.

In some applications, the capsule includes a collapse-prevention element disposed along a portion of the capsule that contains the smoking material, the collapse-prevention element being configured to prevent the portion of the capsule that contains the smoking material from collapsing when mechanical pressure is applied to the portion of the capsule that contains the smoking material.

In some applications, the capsule includes two or more cylindrical collapse-prevention elements disposed at respective ends of a portion of the capsule that contains the smoking material, the cylindrical collapse-prevention elements being configured to prevent the portion of the capsule that contains the smoking material from collapsing when mechanical pressure is applied to the portion of the capsule that contains the smoking material.

In some applications, the one or more heating elements include one or more magnetically-heated materials that are susceptible to being heated by a magnetic field.

In some applications, the portion of the capsule is configured to be inserted into a coil that has a non-circular cross-sectional shape.

In some applications, the portion of the capsule is configured to be flattened while the portion of the capsule is disposed within a coil.

In some applications, the one or more heating elements include a metallic foil that is configured to be heated via resistive heating.

In some applications, the smoking device includes two or more electrodes that are configured to drive an electrical current through the metallic foil, and the capsule is configured to be flattened by the two or more electrodes.

In some applications, the metallic foil has a thickness of between 1 micron and 20 microns. In some applications, the metallic foil has a thickness of between 3 microns and 10 microns.

In some applications, the capsule includes an elongate capsule having a length of between 15 mm and 150 mm. In some applications, the elongate capsule has a length of between 50 mm and 90 mm.

In some applications, the capsule is configured to be flattened such as to define a cross-sectional shape having a ratio of more than 2:1 between a long side of the cross-sectional shape and a short side of the cross-sectional shape. In some applications, the capsule is configured to be flattened such as to define a cross-sectional shape having a ratio of more than 3:1 between a long side of the cross-sectional shape and a short side of the cross-sectional shape. In some applications, the capsule is configured to be flattened such as to define a cross-sectional shape having a ratio of more than 4:1 between a long side of the cross-sectional shape and a short side of the cross-sectional shape. In some applications, the capsule is configured to be flattened such as to define a cross-sectional shape having a ratio of more than 6:1 between a long side of the cross-sectional shape and a short side of the cross-sectional shape.

There is further provided, in accordance with some applications of the present invention, apparatus for use with a smoking device, the apparatus including:
    an elongate capsule including:
        a smoking material containing one or more active agents; and
        one or more heating elements disposed within the capsule, the one or more heating elements being configured to vaporize one or more of the active agents from within the smoking material, by the one or more heating elements being heated by the smoking device,
        at least when the one or more heating elements are being heated by the smoking device, the elongate capsule being configured such as to define a cross-sectional shape having a ratio of more than 2:1 between a long side of the cross-sectional shape and a short side of the cross-sectional shape.

In some applications, the elongate capsule is manufactured such as to define the cross-sectional shape having a ratio of more than 2:1 between a long side of the cross-sectional shape and a short side of the cross-sectional shape.

In some applications, the elongate capsule includes a collapse-prevention element disposed along a portion of the capsule that contains the smoking material, the collapse-prevention element being configured to prevent the portion of the capsule that contains the smoking material from collapsing when mechanical pressure is applied to the portion of the capsule that contains the smoking material.

In some applications, the elongate capsule includes two or more cylindrical collapse-prevention elements disposed at respective ends of a portion of the capsule that contains the smoking material, the collapse-prevention elements being configured to prevent the portion of the capsule that contains the smoking material from collapsing when mechanical pressure is applied to the portion of the capsule that contains the smoking material.

In some applications, the one or more heating elements include one or more magnetically-heated materials that are susceptible to being heated by a magnetic field.

In some applications, the elongate capsule has a length of between 15 mm and 150 mm. In some applications, the elongate capsule has a length of between 50 mm and 90 mm.

In some applications, the elongate capsule is manufactured such as to define a cylindrical shape and at least a portion of the capsule is configured to be flattened by the smoking device such as to define the cross-sectional shape having a ratio of more than 2:1 between a long side of the cross-sectional shape and a short side of the cross-sectional shape, prior to the one or more heating elements being heated by the smoking device.

In some applications, the one or more heating elements include one or more magnetically-heated materials that are susceptible to being heated by a magnetic field.

In some applications, the portion of the capsule is configured to be inserted into a coil that has a non-circular cross-sectional shape.

In some applications, the portion of the capsule is configured to be flattened while the portion of the capsule is disposed within a coil.

In some applications, the one or more heating elements include a metallic foil that is configured to be heated via resistive heating.

In some applications, the smoking device includes two or more electrodes that are configured to drive an electrical current through the metallic foil, and the capsule is configured to be flattened by the two or more electrodes.

In some applications, at least when the one or more heating elements are being heated by the smoking device, the elongate capsule is configured such as to define a cross-sectional shape having a ratio of more than 3:1 between a long side of the cross-sectional shape and a short side of the cross-sectional shape. In some applications, at least when the one or more heating elements are being heated by the smoking device, the elongate capsule is configured such as to define a cross-sectional shape having a ratio of more than 4:1 between a long side of the cross-sectional shape and a short side of the cross-sectional shape. In some applications, at least when the one or more heating elements are being heated by the smoking device, the elongate capsule is configured such as to define a cross-sectional shape having a ratio of more than 6:1 between a long side of the cross-sectional shape and a short side of the cross-sectional shape.

In some applications, the one or more heating elements include a metallic foil that is configured to be heated via resistive heating. In some applications, the metallic foil has a thickness of between 1 micron and 20 microns. In some applications, the metallic foil has a thickness of between 3 microns and 10 microns.

There is further provided, in accordance with some applications of the present invention, apparatus for use with a smoking device, the apparatus including:

a capsule including:
  a smoking material containing one or more active agents;
  one or more heating elements disposed within the capsule, the one or more heating elements being configured to vaporize one or more of the active agents from within the smoking material, by the one or more heating elements being heated by the smoking device; and
  a collapse-prevention element disposed along an axis of a portion of the capsule that contains the smoking material, the collapse-prevention element being configured to prevent the portion of the capsule that contains the smoking material from collapsing when mechanical pressure is applied to the portion of the capsule that contains the smoking material.

In some applications, at least part of the portion of the capsule that contains the smoking material is configured to be flattened by the smoking device and the collapse-prevention element is configured to prevent the portion of the capsule that contains the smoking material from collapsing when at least part of the portion of the capsule that contains the smoking material is flattened by the smoking device.

In some applications, the collapse-prevention element is configured to diffuse one or more chemicals. In some applications, the collapse-prevention element includes a phase-change material that is configured to prevent the temperature of the smoking material from exceeding the phase-change temperature of the phase-change material. In some applications, the collapse-prevention element is configured to absorb chemicals that are generated by pyrolysis of the smoking material.

In some applications, the capsule includes two or more cylindrical collapse-prevention elements disposed at respective ends of a portion of the capsule that contains the smoking material, the collapse-prevention elements being configured to prevent the portion of the capsule that contains the smoking material from collapsing when mechanical pressure is applied to the portion of the capsule that contains the smoking material.

In some applications, the collapse-prevention element is configured to facilitate adequate airflow through the capsule by preventing the portion of the capsule that contains the smoking material from collapsing when mechanical pressure is applied to the portion of the capsule that contains the smoking material.

In some applications, the one or more heating elements include one or more magnetically-heated materials that are susceptible to being heated by a magnetic field.

In some applications, the capsule is manufactured such as to define a cross-sectional shape having a ratio of more than 2:1 between a long side of the cross-sectional shape and a short side of the cross-sectional shape.

In some applications, the smoking device includes two or more electrodes, and the one or more heating elements include a metallic foil that is configured to be heated via resistive heating via the two or more electrodes.

In some applications, the collapse-prevention element is configured to facilitate electrical contact between the two or more electrodes and the metallic foil by preventing the portion of the capsule that contains the smoking material from collapsing when mechanical pressure is applied to the portion of the capsule that contains the smoking material.

In some applications, the metallic foil has a thickness of between 1 micron and 20 microns. In some applications, the metallic foil has a thickness of between 3 microns and 10 microns.

In some applications, at least a portion of the capsule is configured to be flattened by the smoking device prior to the one or more heating elements being heated by the smoking device. In some applications, the capsule has a circular cross-sectional shape and is configured to be flattened to define a non-circular cross-sectional shape.

In some applications, the capsule is configured to be flattened such as to define a cross-sectional shape having a ratio of more than 2:1 between a long side of the cross-sectional shape and a short side of the cross-sectional shape.

In some applications, the one or more heating elements include one or more magnetically-heated materials that are susceptible to being heated by a magnetic field.

In some applications, the portion of the capsule that is configured to be flattened by the smoking device is configured to be inserted into a coil that has a non-circular cross-sectional shape.

In some applications, the portion of the capsule is configured to be flattened by the smoking device is configured to be flattened while the portion of the capsule is disposed within a coil.

In some applications, the one or more heating elements include a metallic foil that is configured to be heated via resistive heating.

In some applications, the smoking device includes two or more electrodes that are configured to drive an electrical current through the metallic foil, and the capsule is configured to be flattened by the two or more electrodes.

In some applications, the collapse-prevention element is shaped as at least one rod that extends axially along a longitudinal axis of the portion of the capsule that contains the smoking material. In some applications, the rod has a diameter of between 0.5 mm and 5 mm. In some applications, the rod extends along only part of the portion of the capsule that contains the smoking material. In some applications, the collapse-prevention element is shaped as two or more rods. In some applications, the smoking device includes two or more electrodes that are configured to drive an electrical current into the capsule, and at locations at which the electrodes are configured to come into contact with the capsule, the rod includes radially-protruding portions having a greater diameter than at other locations along the rod.

In some applications, the collapse-prevention element is shaped as at least one tube that extends axially along a longitudinal axis of the portion of the capsule that contains the smoking material. In some applications, the tube contains one or more chemicals that are configured to be released from the tube during heating of the smoking material.

In some applications, the capsule includes a mouthpiece, and the tube is configured to collect vaporized active agents generated by the heating of the smoking material and direct the vapors toward the mouthpiece.

In some applications, the capsule includes an elongate capsule having a length of between 15 mm and 150 mm. In some applications, the elongate capsule has a length of between 50 mm and 90 mm.

There is further provided, in accordance with some applications of the present invention, apparatus for use with a smoking device, the apparatus including:

a capsule including:

a smoking material containing one or more active agents;

one or more heating elements disposed within the capsule the one or more heating elements being configured to vaporize one or more of the active agents from within the smoking material, by the one or more heating element being heated by the smoking device; and two or more cylindrical collapse-prevention elements disposed at respective ends of a portion of the capsule that contains the smoking material, the collapse-prevention elements being configured to prevent the portion of the capsule that contains the smoking material from collapsing when mechanical pressure is applied to the portion of the capsule that contains the smoking material.

In some applications, at least part of the portion of the capsule that contains the smoking material is configured to be flattened by the smoking device and the cylindrical collapse-prevention elements are configured to prevent the portion of the capsule that contains the smoking material from collapsing when at least part of the portion of the capsule that contains the smoking material is flattened by the smoking device.

In some applications, the capsule further includes a rod-shaped collapse-prevention element disposed along a portion of the capsule that contains the smoking material, the rod-shaped collapse-prevention element being configured to prevent the portion of the capsule that contains the smoking material from collapsing when mechanical pressure is applied to the portion of the capsule that contains the smoking material.

In some applications, the capsule further includes a tube-shaped collapse-prevention element disposed along a portion of the capsule that contains the smoking material, the tube-shaped collapse-prevention element being configured to prevent the portion of the capsule that contains the smoking material from collapsing when mechanical pressure is applied to the portion of the capsule that contains the smoking material.

In some applications, the cylindrical collapse-prevention elements are configured to facilitate adequate airflow through the capsule by preventing the portion of the capsule that contains the smoking material from collapsing when mechanical pressure is applied to the portion of the capsule that contains the smoking material.

In some applications, the one or more heating elements include one or more magnetically-heated materials that are susceptible to being heated by a magnetic field.

In some applications, the capsule is manufactured such as to define a cross-sectional shape having a ratio of more than 2:1 between a long side of the cross-sectional shape and a short side of the cross-sectional shape.

In some applications, the smoking device includes two or more electrodes, and the one or more heating elements include a metallic foil that is configured to be heated via resistive heating via the two or more electrodes.

In some applications, the cylindrical collapse-prevention elements are configured to facilitate electrical contact between the two or more electrodes and the metallic foil by preventing the portion of the capsule that contains the smoking material from collapsing when mechanical pressure is applied to the portion of the capsule that contains the smoking material.

In some applications, the metallic foil has a thickness of between 1 micron and 20 microns. In some applications, the metallic foil has a thickness of between 3 microns and 10 microns.

In some applications, at least a portion of the capsule is configured to be flattened by the smoking device prior to the one or more heating elements being heated by the smoking device. In some applications, the capsule has a circular cross-sectional shape and is configured to be flattened to define a non-circular cross-sectional shape.

In some applications, the capsule is configured to be flattened such as to define a cross-sectional shape having a ratio of more than 2:1 between a long side of the cross-sectional shape and a short side of the cross-sectional shape.

In some applications, the one or more heating elements include one or more magnetically-heated materials that are susceptible to being heated by a magnetic field.

In some applications, the portion of the capsule is configured to be inserted into a coil that has a non-circular cross-sectional shape.

In some applications, the portion of the capsule is configured to be flattened while the portion of the capsule is disposed within a coil.

In some applications, the one or more heating elements include a metallic foil that is configured to be heated via resistive heating.

In some applications, the smoking device includes two or more electrodes that are configured to drive an electrical current through the metallic foil, and the capsule is configured to be flattened by the two or more electrodes.

In some applications, the capsule includes an elongate capsule having a length of between 15 mm and 150 mm. In some applications, the elongate capsule has a length of between 50 mm and 90 mm.

There is further provided, in accordance with some applications of the present invention, apparatus for use with a smoking device, the apparatus including:

an elongate capsule including:

a smoking material containing one or more active agents disposed along a portion of a length of the capsule;

two cylindrical elements disposed at respective ends of the portion of the length of the capsule that contains the smoking material, such that a predefined quantity of smoking material disposed between the two cylindrical elements;

one or more heating elements disposed within the capsule, the one or more heating elements being configured to vaporize one or more of the active agents from within the smoking material, by the one or more heating elements being heated by the smoking device, the predefined quantity of smoking material disposed between the two cylindrical elements is configured to provide a metered dose of the one or more active agents to a user.

In some applications, the one or more heating elements include a metallic foil that is configured to be heated via resistive heating.

In some applications, the one or more heating elements include one or more magnetically-heated materials that are susceptible to being heated by a magnetic field.

In some applications, the elongate capsule is manufactured such as to define a cross-sectional shape having a ratio of more than 2:1 between a long side of the cross-sectional shape and a short side of the cross-sectional shape.

In some applications, the two cylindrical elements are configured to prevent the portion of the capsule that contains the smoking material from collapsing when mechanical pressure is applied to the portion of the capsule that contains the smoking material.

In some applications, at least part of the portion of the elongate capsule that contains the smoking material is configured to be flattened by the smoking device and the cylindrical elements are configured to prevent the portion of the capsule that contains the smoking material from collapsing when at least part of the portion of the capsule that contains the smoking material is flattened by the smoking device.

In some applications, the elongate capsule further includes a rod-shaped collapse-prevention element disposed along a portion of the capsule that contains the smoking material, the rod-shaped collapse-prevention element being configured to prevent the portion of the capsule that contains the smoking material from collapsing when mechanical pressure is applied to the portion of the capsule that contains the smoking material.

In some applications, the elongate capsule further includes a tube-shaped collapse-prevention element disposed along a portion of the capsule that contains the smoking material, the tube-shaped collapse-prevention element being configured to prevent the portion of the capsule that contains the smoking material from collapsing when mechanical pressure is applied to the portion of the capsule that contains the smoking material.

In some applications, the cylindrical elements are configured to facilitate adequate airflow through the capsule by preventing the portion of the capsule that contains the smoking material from collapsing when mechanical pressure is applied to the portion of the capsule that contains the smoking material.

In some applications, the smoking device includes two or more electrodes, and the one or more heating elements include a metallic foil that is configured to be heated via resistive heating via the two or more electrodes.

In some applications, the cylindrical collapse-prevention elements are configured to facilitate electrical contact between the two or more electrodes and the metallic foil by preventing the portion of the capsule that contains the smoking material from collapsing when mechanical pressure is applied to the portion of the capsule that contains the smoking material.

In some applications, the metallic foil has a thickness of between 1 micron and 20 microns. In some applications, the metallic foil has a thickness of between 3 microns and 10 microns.

In some applications, at least a portion of the capsule is configured to be flattened by the smoking device prior to the one or more heating elements being heated by the smoking device.

In some applications, the cylindrical elements are configured to facilitate adequate airflow through the capsule by preventing the portion of the capsule that contains the smoking material from collapsing when the portion of the capsule is flattened.

In some applications, the capsule has a circular cross-sectional shape and is configured to be flattened to define a non-circular cross-sectional shape.

In some applications, the capsule is configured to be flattened such as to define a cross-sectional shape having a ratio of more than 2:1 between a long side of the cross-sectional shape and a short side of the cross-sectional shape.

In some applications, the one or more heating elements include one or more magnetically-heated materials that are susceptible to being heated by a magnetic field.

In some applications, the portion of the capsule is configured to be inserted into a coil that has a non-circular cross-sectional shape.

In some applications, the portion of the capsule is configured to be flattened while the portion of the capsule is disposed within a coil.

In some applications, the one or more heating elements include a metallic foil that is configured to be heated via resistive heating. In some applications, the smoking device includes two or more electrodes that are configured to drive an electrical current through the metallic foil, and the capsule is configured to be flattened by the two or more electrodes.

In some applications, the elongate capsule has a length of between 15 mm and 150 mm. In some applications, the elongate capsule has a length of between 50 mm and 90 mm.

There is further provided, in accordance with some applications of the present invention, apparatus for use with a smoking device including an infrared temperature sensor, the apparatus including:

a capsule including:
   a smoking material containing one or more active agents;
   a metallic foil disposed around at least a portion of the smoking material, the metallic foil being configured to vaporize one or more of the active agents from within the smoking material, by the metallic foil being heated by the smoking device via resistive heating; and
   a coating disposed around at least a portion of the metallic foil at which the infrared temperature sensor is configured to detect a temperature of the capsule, the coating having an emissivity value of at least 0.5.

In some applications, the coating has an emissivity value of at least 0.95.

There is further provided, in accordance with some applications of the present invention, apparatus for use with a smoking device including an infrared temperature sensor, the apparatus including:

a capsule including:
   a smoking material containing one or more active agents;
   a metallic foil disposed around at least a portion of the smoking material, the metallic foil being configured to vaporize one or more of the active agents from within the smoking material, by the metallic foil being heated by the smoking device via resistive heating; and
   at least a portion of the metallic foil at which the infrared temperature sensor the infrared temperature sensor is configured to detect a temperature of the capsule the metallic foil being treated such as to have an emissivity value of at least 0.5.

In some applications, the portion of the metallic foil is treated such as to have an emissivity value of at least 0.95.

There is further provided, in accordance with some applications of the present invention, apparatus for use with a smoking device including an infrared temperature sensor, the apparatus including:

a capsule including:
   a smoking material containing one or more active agents;
   one or more resistive elements, the resistive elements being configured to provide an electrical resistance profile to the capsule that provides identifying information regarding the capsule.

There is further provided, in accordance with some applications of the present invention, apparatus for use with a smoking device that includes at least first and second electrodes, the apparatus including:

an elongate capsule having a length of between 15 mm and 150 mm, the elongate capsule including:
   a smoking material containing one or more active agents; and
   metallic foil surrounding the smoking material, the metallic foil being configured to be heated via resistive heating by the first electrode driving a current to the second electrode along a length of more than 5 mm in an axial direction along the metallic foil.

In some applications, the elongate capsule has a length of between 50 mm and 90 mm.

In some applications, the capsule is configured such that airflow through the capsule is substantially in an axial direction along a length of the capsule.

In some applications, the metallic foil is configured to be heated via resistive heating by the first electrode driving a current to the second electrode along a length of more than 15 mm in the axial direction along the metallic foil.

In some applications, the capsule further includes a paper covering that covers the make electrical contact with the metallic foil.

In some applications, the metallic foil is shaped such that at least a portion of the metallic foil is embedded within the smoking material.

In some applications, the metallic foil includes a plurality of regions, each of the regions having a respective, different electrical resistance profile, such that upon a given current being driven through the metallic foil each of the regions heats to a respective, different temperature.

In some applications, the capsule further includes a collapse-prevention element configured to facilitate electrical contact between the electrodes and the metallic foil, by preventing the capsule from collapsing.

In some applications, the capsule further includes an electrical-contact coating that coats the metallic foil at locations at which the electrodes are configured to contact the capsule.

In some applications, the metallic foil has a first configuration at locations at which the electrodes are configured to contact the metallic foil, and a second configuration along a region in which the metallic foil surrounds the smoking material that is between the locations at which the electrodes are configured to contact the metallic foil.

In some applications, the capsule further includes an inner lining that lines an inside of the metallic foil, the inner lining being configured to diffuse heat that is generated by the metallic foil.

In some applications, the smoking device includes one or more batteries, and an overall resistance to the current that is provided by the capsule is configured to substantially match an internal resistance of the one or more batteries of the smoking device.

In some applications, the capsule further includes a paper covering that covers the metallic foil, the paper covering being adhered to itself along a band of overlap such as to form a cylindrical shape, and an electrically insulating material is disposed along the band of overlap, to isolate an inner layer of the metallic foil from the electrodes.

In some applications, the capsule further includes a paper covering that covers the metallic foil, the paper covering being adhered to itself along a band of overlap, such as to form a cylindrical shape, and the metallic foil is treated along the band of overlap, in order to increase resistance of the metallic foil along the band of overlap.

In some applications, the capsule is shaped to define a cross-sectional shape having a ratio of more than 2:1 between a long side of the cross-sectional shape and a short side of the cross-sectional shape.

In some applications, at least a portion of the capsule is configured to be flattened by the smoking device prior to the one or more heating elements being heated by the smoking device. In some applications, the capsule has a circular cross-sectional shape and is configured to be flattened to define a non-circular cross-sectional shape. In some applications, the capsule is configured to be flattened such as to define a cross-sectional shape having a ratio of more than 2:1 between a long side of the cross-sectional shape and a short side of the cross-sectional shape.

In some applications, the metallic foil has a thickness of between 1 micron and 20 microns. In some applications, the metallic foil has a thickness of between 3 microns and 10 microns.

There is further provided, in accordance with some applications of the present invention, apparatus for use with a smoking device that includes at least first and second electrodes, the apparatus including:

a capsule including:

a smoking material containing one or more active agents; and metallic foil surrounding the smoking material, the metallic foil being configured to be heated via resistive heating by the electrodes driving a current into the metallic foil; and a paper covering that covers the metallic foil, the paper covering defining openings via which the electrodes are configured to make electrical contact with the metallic foil.

In some applications, the metallic foil is shaped such that at least a portion of the metallic foil is embedded within the smoking material.

In some applications, the metallic foil includes a plurality of regions, each of the regions having a respective, different electrical resistance profile, such that upon a given current being driven through the metallic foil each of the regions heats to a respective, different temperature.

In some applications, the capsule further includes a collapse-prevention element configured to facilitate electrical contact between the electrodes and the metallic foil, by preventing the capsule from collapsing.

In some applications, the capsule further includes an electrical-contact coating that coats the metallic foil at locations at which the electrodes are configured to contact the capsule.

In some applications, the metallic foil has a first configuration at locations at which the electrodes are configured to contact the metallic foil, and a second configuration along a region in which the metallic foil surrounds the smoking material that is between the locations at which the electrodes are configured to contact the metallic foil.

In some applications, the capsule further includes an inner lining that lines an inside of the metallic foil, the inner lining being configured to diffuse heat that is generated by the metallic foil.

In some applications, the smoking device includes one or more batteries, and an overall resistance to the current that is provided by the capsule is configured to substantially match an internal resistance of the one or more batteries of the smoking device.

In some applications, the paper covering is adhered to itself along a band of overlap, such as to form a cylindrical shape, and an electrically insulating material is disposed along the band of overlap, to isolate an inner layer of the metallic foil from the electrodes. In some applications, the paper covering is adhered to itself along a band of overlap, such as to form a cylindrical shape, and the metallic foil is treated along the band of overlap, in order to increase resistance of the metallic foil along the band of overlap.

In some applications, the capsule is shaped to define a cross-sectional shape having a ratio of more than 2:1 between a long side of the cross-sectional shape and a short side of the cross-sectional shape.

In some applications, at least a portion of the capsule is configured to be flattened by the smoking device prior to the one or more heating elements being heated by the smoking device. In some applications, the capsule has a circular cross-sectional shape and is configured to be flattened to define a non-circular cross-sectional shape. In some applications, the capsule is configured to be flattened such as to define a cross-sectional shape having a ratio of more than 2:1 between a long side of the cross-sectional shape and a short side of the cross-sectional shape.

In some applications, the capsule includes an elongate capsule having a length of between 15 mm and 150 mm. In some applications, the elongate capsule has a length of between 50 mm and 90 mm.

In some applications, the capsule is configured such that airflow through the capsule is substantially in an axial direction along a length of the capsule.

In some applications, the metallic foil is configured to be heated via resistive heating by the first electrode driving a current to the second electrode along a length of more than 5 mm in an axial direction along the metallic foil. In some applications, the capsule is configured such that airflow through the capsule is substantially in the axial direction along a length of the capsule. In some applications, the metallic foil is configured to be heated via resistive heating by the first electrode driving a current to the second electrode along a length of more than 15 mm in the axial direction along the metallic foil.

In some applications, the metallic foil has a thickness of between 1 micron and 20 microns. In some applications, the metallic foil has a thickness of between 3 microns and 10 microns.

There is further provided, in accordance with some applications of the present invention, apparatus for use with a smoking device that includes at least first and second electrodes, the apparatus including:

a capsule including:

a smoking material containing one or more active agents; and metallic foil surrounding the smoking material, the metallic foil being configured to be heated via resistive heating by the electrodes driving a current into the metallic foil, the metallic foil being shaped such that at least a portion of the metallic foil is embedded within the smoking material.

In some applications, the metallic foil is folded such as to define ribs that are embedded within the smoking material.

In some applications, the metallic foil is shaped to define a flap that is embedded within the smoking material.

In some applications, the metallic foil is shaped to define a spiral that spirals through the smoking material.

In some applications, the metallic foil includes a plurality of regions, each of the regions having a respective, different electrical resistance profile, such that upon a given current being driven through the metallic foil each of the regions heats to a respective, different temperature.

In some applications, the capsule further includes a collapse-prevention element configured to facilitate electrical contact between the electrodes and the metallic foil, by preventing the capsule from collapsing.

In some applications, the capsule further includes an electrical-contact coating that coats the metallic foil at locations at which the electrodes are configured to contact the capsule.

In some applications, the metallic foil has a first configuration at locations at which the electrodes are configured to contact the metallic foil, and a second configuration along a region in which the metallic foil surrounds the smoking material that is between the locations at which the electrodes are configured to contact the metallic foil.

In some applications, the capsule further includes an inner lining that lines an inside of the metallic foil, the inner lining being configured to diffuse heat that is generated by the metallic foil.

In some applications, the smoking device includes one or more batteries, and an overall resistance to the current that is provided by the capsule is configured to substantially match an internal resistance of the one or more batteries of the smoking device.

In some applications, the capsule further includes a paper covering that covers the metallic foil, the paper covering being adhered to itself along a band of overlap, such as to form a cylindrical shape, and an electrically insulating material is disposed along the band of overlap, to isolate an inner layer of the metallic foil from the electrodes.

In some applications, the capsule further includes a paper covering that covers the metallic foil, the paper covering being adhered to itself along a band of overlap, such as to form a cylindrical shape, and the metallic foil is treated along the band of overlap, in order to increase resistance of the metallic foil along the band of overlap.

In some applications, the capsule is shaped to define a cross-sectional shape having a ratio of more than 2:1 between a long side of the cross-sectional shape and a short side of the cross-sectional shape.

In some applications, the capsule further includes a paper covering that covers the metallic foil, the paper covering defining openings via which the electrodes are configured to make electrical contact with the metallic foil.

In some applications, at least a portion of the capsule is configured to be flattened by the smoking device prior to the one or more heating elements being heated by the smoking device. In some applications, the capsule has a circular cross-sectional shape and is configured to be flattened to define a non-circular cross-sectional shape. In some applications, the capsule is configured to be flattened such as to define a cross-sectional shape having a ratio of more than 2:1 between a long side of the cross-sectional shape and a short side of the cross-sectional shape.

In some applications, the capsule includes an elongate capsule having a length of between 15 mm and 150 mm. In some applications, the elongate capsule has a length of between 50 mm and 90 mm.

In some applications, the capsule is configured such that airflow through the capsule is substantially in an axial direction along a length of the capsule.

In some applications, the metallic foil is configured to be heated via resistive heating by the first electrode driving a current to the second electrode along a length of more than 5 mm in an axial direction along the metallic foil. In some applications, the capsule is configured such that airflow through the capsule is substantially in the axial direction along a length of the capsule. In some applications, the metallic foil is configured to be heated via resistive heating by the first electrode driving a current to the second electrode along a length of more than 15 mm in the axial direction along the metallic foil.

In some applications, the metallic foil has a thickness of between 1 micron and 20 microns. In some applications, the metallic foil has a thickness of between 3 microns and 10 microns.

There is further provided, in accordance with some applications of the present invention, apparatus for use with a smoking device that includes at least first and second electrodes, the apparatus including:

a capsule including:
  a smoking material containing one or more active agents; and
  metallic foil surrounding the smoking material, the metallic foil being configured to be heated via resistive heating by the electrodes driving a current into the metallic foil, the metallic foil including a plurality of regions along its length, each of the regions having a respective, different electrical resistance profile, such that upon a given current being driven through the metallic foil each of the regions heats to a respective, different temperature.

In some applications, the metallic foil is shaped such that at least a portion of the metallic foil is embedded within the smoking material.

In some applications, the capsule further includes a collapse-prevention element configured to facilitate electrical contact between the electrodes and the metallic foil, by preventing the capsule from collapsing.

In some applications, the capsule further includes an electrical-contact coating that coats the metallic foil at locations at which the electrodes are configured to contact the capsule.

In some applications, the metallic foil has a first configuration at locations at which the electrodes are configured to contact the metallic foil, and a second configuration along a region in which the metallic foil surrounds the smoking material that is between the locations at which the electrodes are configured to contact the metallic foil.

In some applications, the capsule further includes an inner lining that lines an inside of the metallic foil, the inner lining being configured to diffuse heat that is generated by the metallic foil.

In some applications, the smoking device includes one or more batteries, and an overall resistance to the current that is provided by the capsule is configured to substantially match an internal resistance of the one or more batteries of the smoking device.

In some applications, the capsule further includes a paper covering that covers the metallic foil, the paper covering being adhered to itself along a band of overlap, such as to form a cylindrical shape, and an electrically insulating material is disposed along the band of overlap, to isolate an inner layer of the metallic foil from the electrodes.

In some applications, the capsule further includes a paper covering that covers the metallic foil, the paper covering being adhered to itself along a band of overlap, such as to form a cylindrical shape, and the metallic foil is treated along the band of overlap, in order to increase resistance of the metallic foil along the band of overlap.

In some applications, the capsule is shaped to define a cross-sectional shape having a ratio of more than 2:1 between a long side of the cross-sectional shape and a short side of the cross-sectional shape.

In some applications, the capsule further includes a paper covering that covers the metallic foil, the paper covering defining openings via which the electrodes are configured to make electrical contact with the metallic foil.

In some applications, the capsule is configured for use with a smoking device that includes respective temperature sensors that are configured to detect temperatures of the respective regions along the metallic foil.

In some applications, at least a portion of the capsule is configured to be flattened by the smoking device prior to the one or more heating elements being heated by the smoking device. In some applications, the capsule has a circular cross-sectional shape and is configured to be flattened to define a non-circular cross-sectional shape. In some applications, the capsule is configured to be flattened such as to define a cross-sectional shape having a ratio of more than 2:1 between a long side of the cross-sectional shape and a short side of the cross-sectional shape.

In some applications, the capsule includes an elongate capsule having a length of between 15 mm and 150 mm. In some applications, the elongate capsule has a length of between 50 mm and 90 mm.

In some applications, the capsule is configured such that airflow through the capsule is substantially in an axial direction along a length of the capsule.

In some applications, the metallic foil is configured to be heated via resistive heating by the first electrode driving a current to the second electrode along a length of more than 5 mm in an axial direction along the metallic foil. In some applications, the capsule is configured such that airflow through the capsule is substantially in the axial direction along a length of the capsule. In some applications, the metallic foil is configured to be heated via resistive heating by the first electrode driving a current to the second electrode along a length of more than 15 mm in the axial direction along the metallic foil.

In some applications, the metallic foil has a thickness of between 1 micron and 20 microns. In some applications, the metallic foil has a thickness of between 3 microns and 10 microns.

In some applications, each of the regions along the length of the metallic foil includes a respective, different material that is configured to be vaporized by heating of the metallic foil.

In some applications, the capsule is configured for use with a smoking device that is configured to receive an input from a user indicating a preferred mix of vapors of the user, and to heat the respective regions along the length of the metallic foil to respective, different temperatures responsively thereto.

There is further provided, in accordance with some applications of the present invention, apparatus for use with a smoking device that includes at least first and second electrodes, the apparatus including:

a capsule including:

a smoking material containing one or more active agents; and metallic foil surrounding the smoking material, the metallic foil being configured to be heated via resistive heating by the electrodes driving a current into the metallic foil; and a collapse-prevention element configured to facilitate electrical contact between the electrodes and the metallic foil, by preventing the capsule from collapsing.

In some applications, the metallic foil includes a plurality of regions, each of the regions having a respective, different electrical resistance profile, such that upon a given current being driven through the metallic foil each of the regions heats to a respective, different temperature.

In some applications, the metallic foil is shaped such that at least a portion of the metallic foil is embedded within the smoking material.

In some applications, the capsule further includes an electrical-contact coating that coats the metallic foil at locations at which the electrodes are configured to contact the capsule.

In some applications, the metallic foil has a first configuration at locations at which the electrodes are configured to contact the metallic foil, and a second configuration along a region in which the metallic foil surrounds the smoking material that is between the locations at which the electrodes are configured to contact the metallic foil.

In some applications, the capsule further includes an inner lining that lines an inside of the metallic foil, the inner lining being configured to diffuse heat that is generated by the metallic foil.

In some applications, the smoking device includes one or more batteries, and an overall resistance to the current that is provided by the capsule is configured to substantially match an internal resistance of the one or more batteries of the smoking device.

In some applications, the capsule further includes a paper covering that covers the metallic foil, the paper covering being adhered to itself along a band of overlap, such as to form a cylindrical shape, and an electrically insulating material is disposed along the band of overlap, to isolate an inner layer of the metallic foil from the electrodes.

In some applications, the capsule further includes a paper covering that covers the metallic foil, the paper covering being adhered to itself along a band of overlap, such as to form a cylindrical shape, and the metallic foil is treated along the band of overlap, in order to increase resistance of the metallic foil along the band of overlap.

In some applications, the capsule is shaped to define a cross-sectional shape having a ratio of more than 2:1 between a long side of the cross-sectional shape and a short side of the cross-sectional shape.

In some applications, the capsule further includes a paper covering that covers the make electrical contact with the metallic foil.

In some applications, the collapse-prevention element is configured to diffuse one or more chemicals. In some applications, the collapse-prevention element includes a phase-change material that is configured to prevent the temperature of the smoking material from exceeding the phase-change temperature of the phase-change material. In some applications, the collapse-prevention element is configured to absorb chemicals that are generated by pyrolysis of the smoking material. In some applications, the collapse-prevention element includes two or more cylindrical collapse-prevention elements disposed at respective ends of the portion of the capsule that contains the smoking material.

In some applications, at least a portion of the capsule is configured to be flattened by the smoking device prior to the one or more heating elements being heated by the smoking device. In some applications, the capsule has a circular cross-sectional shape and is configured to be flattened to define a non-circular cross-sectional shape. In some applications, the capsule is configured to be flattened such as to define a cross-sectional shape having a ratio of more than 2:1 between a long side of the cross-sectional shape and a short side of the cross-sectional shape.

In some applications, the capsule includes an elongate capsule having a length of between 15 mm and 150 mm. In some applications, the elongate capsule has a length of between 50 mm and 90 mm.

In some applications, the capsule is configured such that airflow through the capsule is substantially in an axial direction along a length of the capsule.

In some applications, the metallic foil is configured to be heated via resistive heating by the first electrode driving a current to the second electrode along a length of more than 5 mm in an axial direction along the metallic foil. In some applications, the capsule is configured such that airflow through the capsule is substantially in the axial direction along a length of the capsule. In some applications, the metallic foil is configured to be heated via resistive heating by the first electrode driving a current to the second electrode along a length of more than 15 mm in the axial direction along the metallic foil.

In some applications, the collapse-prevention element is shaped as at least one rod that extends axially along a longitudinal axis of the portion of the capsule that contains the smoking material. In some applications, the rod has a diameter of between 0.5 mm and 5 mm. In some applications, the rod extends along only part of the portion of the capsule that contains the smoking material. In some applications, the collapse-prevention element is shaped as two or more rods. In some applications, the smoking device includes two or more electrodes that are configured to drive an electrical current into the capsule, and at locations at which the electrodes are configured to come into contact with the capsule, the rod includes radially-protruding portions having a greater diameter than at other locations along the rod.

In some applications, the collapse-prevention element is shaped as at least one tube that extends axially along a longitudinal axis of the portion of the capsule that contains the smoking material. In some applications, the tube contains one or more chemicals that are configured to be released from the tube during heating of the smoking material. In some applications, the capsule includes a mouthpiece, and the tube is configured to collect vaporized active agents generated by the heating of the smoking material and direct the vapors toward the mouthpiece.

In some applications, the metallic foil has a thickness of between 1 micron and 20 microns. In some applications, the metallic foil has a thickness of between 3 microns and 10 microns.

There is further provided, in accordance with some applications of the present invention, apparatus for use with a smoking device that includes at least first and second electrodes and one or more batteries, the apparatus including:

a capsule including:

a smoking material containing one or more active agents; and metallic foil surrounding the smoking material, the metallic foil being configured to be heated via resistive heating by the electrodes driving a current into the metallic foil, an overall resistance to the current that is provided by the capsule is configured to substantially match an internal resistance of the one or more batteries of the smoking device.

In some applications, the capsule further includes a collapse-prevention element configured to facilitate electrical contact between the electrodes and the metallic foil, by preventing the capsule from collapsing.

In some applications, the metallic foil includes a plurality of regions, each of the regions having a respective, different electrical resistance profile, such that upon a given current being driven through the metallic foil each of the regions heats to a respective, different temperature.

In some applications, the metallic foil is shaped such that at least a portion of the metallic foil is embedded within the smoking material.

In some applications, the capsule further includes an electrical-contact coating that coats the metallic foil at locations at which the electrodes are configured to contact the capsule.

In some applications, the metallic foil has a first configuration at locations at which the electrodes are configured to contact the metallic foil, and a second configuration along a region in which the metallic foil surrounds the smoking material that is between the locations at which the electrodes are configured to contact the metallic foil.

In some applications, the capsule further includes an inner lining that lines an inside of the metallic foil, the inner lining being configured to diffuse heat that is generated by the metallic foil.

In some applications, the capsule further includes a paper covering that covers the metallic foil, the paper covering being adhered to itself along a band of overlap, such as to form a cylindrical shape, and an electrically insulating material is disposed along the band of overlap, to isolate an inner layer of the metallic foil from the electrodes.

In some applications, the capsule further includes a paper covering that covers the metallic foil, the paper covering being adhered to itself along a band of overlap, such as to form a cylindrical shape, and the metallic foil is treated along the band of overlap, in order to increase resistance of the metallic foil along the band of overlap.

In some applications, the capsule is shaped to define a cross-sectional shape having a ratio of more than 2:1 between a long side of the cross-sectional shape and a short side of the cross-sectional shape.

In some applications, the capsule further includes a paper covering that covers the make electrical contact with the metallic foil.

In some applications, at least a portion of the capsule is configured to be flattened by the smoking device prior to the one or more heating elements being heated by the smoking device. In some applications, the capsule has a circular cross-sectional shape and is configured to be flattened to define a non-circular cross-sectional shape. In some applications, the capsule is configured to be flattened such as to define a cross-sectional shape having a ratio of more than 2:1 between a long side of the cross-sectional shape and a short side of the cross-sectional shape.

In some applications, the capsule includes an elongate capsule having a length of between 15 mm and 150 mm. In some applications, the elongate capsule has a length of between 50 mm and 90 mm.

In some applications, the capsule is configured such that airflow through the capsule is substantially in an axial direction along a length of the capsule.

In some applications, the metallic foil is configured to be heated via resistive heating by the first electrode driving a current to the second electrode along a length of more than 5 mm in an axial direction along the metallic foil. In some applications, the capsule is configured such that airflow through the capsule is substantially in the axial direction along a length of the capsule. In some applications, the metallic foil is configured to be heated via resistive heating by the first electrode driving a current to the second electrode along a length of more than 15 mm in the axial direction along the metallic foil.

In some applications, the metallic foil has a thickness of between 1 micron and 20 microns. In some applications, the metallic foil has a thickness of between 3 microns and 10 microns.

There is therefore provided, in accordance with some applications of the present invention, apparatus for use with a smoking device that includes at least first and second electrodes, the apparatus including:

a capsule including:

a smoking material containing one or more active agents; and metallic foil surrounding the smoking material, the metallic foil being configured to be heated via resistive heating by the electrodes driving a current into the metallic foil; and an electrical-contact coating that coats the metallic foil at locations at which the electrodes are configured to contact the capsule.

In some applications, the electrical-contact coating coats an outside of the metallic foil. In some applications, the electrical-contact coating coats an inside of the metallic foil. In some applications, the electrical-contact coating has a lower resistance than a resistance of the metallic foil. In some applications, the electrical-contact coating is configured to prevent generation of hotspots at the locations at which the electrodes are configured to contact the capsule. In some applications, the electrical-contact coating includes a ring-shaped coating at each of the locations at which the electrodes are configured to contact the capsule. In some applications, an edge of the electrical-contact coating is zigzagged at a side at which the coating contacts the metallic foil to thereby conduct electrical current to the metallic foil in a uniform manner.

In some applications, the capsule further includes a collapse-prevention element configured to facilitate electrical contact between the electrodes and the metallic foil, by preventing the capsule from collapsing.

In some applications, the metallic foil includes a plurality of regions, each of the regions having a respective, different electrical resistance profile, such that upon a given current being driven through the metallic foil each of the regions heats to a respective, different temperature.

In some applications, the metallic foil is shaped such that at least a portion of the metallic foil is embedded within the smoking material.

In some applications, the metallic foil has a first configuration at locations at which the electrodes are configured to contact the metallic foil, and a second configuration along a region in which the metallic foil surrounds the smoking material that is between the locations at which the electrodes are configured to contact the metallic foil.

In some applications, the capsule further includes an inner lining that lines an inside of the metallic foil, the inner lining being configured to diffuse heat that is generated by the metallic foil.

In some applications, the smoking device includes one or more batteries, and an overall resistance to the current that is provided by the capsule is configured to substantially match an internal resistance of the one or more batteries of the smoking device.

In some applications, the capsule further includes a paper covering that covers the metallic foil, the paper covering being adhered to itself along a band of overlap, such as to form a cylindrical shape, and an electrically insulating material is disposed along the band of overlap, to isolate an inner layer of the metallic foil from the electrodes.

In some applications, the capsule further includes a paper covering that covers the metallic foil, the paper covering being adhered to itself along a band of overlap, such as to form a cylindrical shape, and the metallic foil is treated along the band of overlap, in order to increase resistance of the metallic foil along the band of overlap.

In some applications, the capsule is shaped to define a cross-sectional shape having a ratio of more than 2:1 between a long side of the cross-sectional shape and a short side of the cross-sectional shape.

In some applications, the capsule further includes a paper covering that covers the metallic foil, the paper covering defining openings via which the electrodes are configured to make electrical contact with the metallic foil.

In some applications, at least a portion of the capsule is configured to be flattened by the smoking device prior to the one or more heating elements being heated by the smoking device. In some applications, the capsule has a circular cross-sectional shape and is configured to be flattened to define a non-circular cross-sectional shape. In some applications, the capsule is configured to be flattened such as to define a cross-sectional shape having a ratio of more than 2:1 between a long side of the cross-sectional shape and a short side of the cross-sectional shape.

In some applications, the capsule includes an elongate capsule having a length of between 15 mm and 150 mm. In some applications, the elongate capsule has a length of between 50 mm and 90 mm.

In some applications, the capsule is configured such that airflow through the capsule is substantially in an axial direction along a length of the capsule.

In some applications, the metallic foil is configured to be heated via resistive heating by the first electrode driving a current to the second electrode along a length of more than 5 mm in an axial direction along the metallic foil. In some applications, the capsule is configured such that airflow through the capsule is substantially in the axial direction along a length of the capsule. In some applications, the metallic foil is configured to be heated via resistive heating by the first electrode driving a current to the second electrode along a length of more than 15 mm in the axial direction along the metallic foil.

In some applications, the metallic foil has a thickness of between 1 micron and 20 microns. In some applications, the metallic foil has a thickness of between 3 microns and 10 microns.

There is further provided, in accordance with some applications of the present invention, apparatus for use with a smoking device that includes at least first and second electrodes, the apparatus including:

a capsule including:

a smoking material containing one or more active agents; and metallic foil surrounding the smoking material, the metallic foil being configured to be heated via resistive heating by the electrodes driving a current into the metallic foil; and the metallic foil having a first configuration at locations at which the electrodes are configured to contact the metallic foil, and the metallic foil having a second configuration along a region in which the metallic foil surrounds the smoking material that is between the locations at which the electrodes are configured to contact the metallic foil.

In some applications, the first configuration of the metallic foil is thicker than the second configuration of the metallic foil.

In some applications, the capsule further includes a collapse-prevention element configured to facilitate electrical contact between the electrodes and the metallic foil, by preventing the capsule from collapsing.

In some applications, the metallic foil includes a plurality of regions, each of the regions having a respective, different electrical resistance profile, such that upon a given current being driven through the metallic foil each of the regions heats to a respective, different temperature.

In some applications, the metallic foil is shaped such that at least a portion of the metallic foil is embedded within the smoking material.

In some applications, the capsule further includes an electrical-contact coating that coats the metallic foil at locations at which the electrodes are configured to contact the capsule.

In some applications, the capsule further includes an inner lining that lines an inside of the metallic foil, the inner lining being configured to diffuse heat that is generated by the metallic foil.

In some applications, the smoking device includes one or more batteries, and an overall resistance to the current that is provided by the capsule is configured to substantially match an internal resistance of the one or more batteries of the smoking device.

In some applications, the capsule further includes a paper covering that covers the metallic foil, the paper covering being adhered to itself along a band of overlap, such as to form a cylindrical shape, and an electrically insulating material is disposed along the band of overlap, to isolate an inner layer of the metallic foil from the electrodes.

In some applications, the capsule further includes a paper covering that covers the metallic foil, the paper covering being adhered to itself along a band of overlap, such as to form a cylindrical shape, and the metallic foil is treated along the band of overlap, in order to increase resistance of the metallic foil along the band of overlap.

In some applications, the capsule is shaped to define a cross-sectional shape having a ratio of more than 2:1 between a long side of the cross-sectional shape and a short side of the cross-sectional shape.

In some applications, the capsule further includes a paper covering that covers the metallic foil, the paper covering defining openings via which the electrodes are configured to make electrical contact with the metallic foil.

In some applications, at least a portion of the capsule is configured to be flattened by the smoking device prior to the one or more heating elements being heated by the smoking device. In some applications, the capsule has a circular cross-sectional shape and is configured to be flattened to define a non-circular cross-sectional shape. In some applications, the capsule is configured to be flattened such as to define a cross-sectional shape having a ratio of more than 2:1 between a long side of the cross-sectional shape and a short side of the cross-sectional shape.

In some applications, the capsule includes an elongate capsule having a length of between 15 mm and 150 mm. In some applications, the elongate capsule has a length of between 50 mm and 90 mm.

In some applications, the capsule is configured such that airflow through the capsule is substantially in an axial direction along a length of the capsule.

In some applications, the metallic foil is configured to be heated via resistive heating by the first electrode driving a current to the second electrode along a length of more than 5 mm in an axial direction along the metallic foil. In some applications, the capsule is configured such that airflow through the capsule is substantially in the axial direction along a length of the capsule. In some applications, the metallic foil is configured to be heated via resistive heating by the first electrode driving a current to the second electrode along a length of more than 15 mm in the axial direction along the metallic foil.

In some applications, the first configuration of the metallic foil is configured to provide lower electrical resistance than the second configuration of the metallic foil. In some applications, the metallic foil is etched in the second configuration of the metallic foil. In some applications, the metallic foil defines openings therethrough in the second configuration of the metallic foil.

In some applications, the capsule further includes a paper covering that covers the metallic foil, and the paper covering covers the openings. In some applications, the capsule further includes a paper covering that covers the metallic foil, and the paper covering does not cover the openings.

In some applications, the metallic foil has a thickness of between 1 micron and 20 microns. In some applications, the metallic foil has a thickness of between 3 microns and 10 microns.

There is further provided, in accordance with some applications of the present invention, apparatus for use with a smoking device that includes at least first and second electrodes, the apparatus including:

a capsule including:

a smoking material containing one or more active agents; and metallic foil surrounding the smoking material, the metallic foil being configured to be heated via resistive heating by the electrodes driving a current into the metallic foil; and an inner lining that lines an inside of the metallic foil, the inner lining being configured to diffuse heat that is generated by the metallic foil.

In some applications, the inner lining includes polyimide. In some applications, the inner lining is configured to diffuse heat that is generated by the metallic foil across the smoking material, thereby preventing hotspots from being generated within the smoking material. In some applications, the inner lining is configured to provide mechanical strength to the capsule, such as to reduce a likelihood of the capsule tearing as a result of mechanical pressure being applied to the capsule. In some applications, the electrodes are configured to apply mechanical pressure to the capsule, and the inner lining is disposed at regions of the capsule that are configured to be compressed by the electrodes.

In some applications, the inner lining is configured to diffuse one or more chemicals. In some applications, the inner lining includes a phase-change material that is configured to prevent the temperature of the smoking material from exceeding the phase-change temperature of the phase-change material. In some applications, the inner lining is configured to absorb chemicals that are generated by pyrolysis of the smoking material.

In some applications, the capsule further includes a collapse-prevention element configured to facilitate electrical contact between the electrodes and the metallic foil, by preventing the capsule from collapsing.

In some applications, the metallic foil includes a plurality of regions, each of the regions having a respective, different electrical resistance profile, such that upon a given current being driven through the metallic foil each of the regions heats to a respective, different temperature.

In some applications, the metallic foil is shaped such that at least a portion of the metallic foil is embedded within the smoking material.

In some applications, the capsule further includes an electrical-contact coating that coats the metallic foil at locations at which the electrodes are configured to contact the capsule.

In some applications, the metallic foil has a first configuration at locations at which the electrodes are configured to contact the metallic foil, and a second configuration along a region in which the metallic foil surrounds the smoking material that is between the locations at which the electrodes are configured to contact the metallic foil.

In some applications, the smoking device includes one or more batteries, and an overall resistance to the current that is provided by the capsule is configured to substantially match an internal resistance of the one or more batteries of the smoking device.

In some applications, the capsule further includes a paper covering that covers the metallic foil, the paper covering being adhered to itself along a band of overlap, such as to form a cylindrical shape, and an electrically insulating material is disposed along the band of overlap, to isolate an inner layer of the metallic foil from the electrodes.

In some applications, the capsule further includes a paper covering that covers the metallic foil, the paper covering being adhered to itself along a band of overlap, such as to form a cylindrical shape, and the metallic foil is treated along the band of overlap, in order to increase resistance of the metallic foil along the band of overlap.

In some applications, the capsule is shaped to define a cross-sectional shape having a ratio of more than 2:1 between a long side of the cross-sectional shape and a short side of the cross-sectional shape.

In some applications, the capsule further includes a paper covering that covers the metallic foil, the paper covering defining openings via which the electrodes are configured to make electrical contact with the metallic foil.

In some applications, at least a portion of the capsule is configured to be flattened by the smoking device prior to the one or more heating elements being heated by the smoking device. In some applications, the capsule has a circular cross-sectional shape and is configured to be flattened to define a non-circular cross-sectional shape. In some applications, the capsule is configured to be flattened such as to define a cross-sectional shape having a ratio of more than 2:1 between a long side of the cross-sectional shape and a short side of the cross-sectional shape.

In some applications, the capsule includes an elongate capsule having a length of between 15 mm and 150 mm. In some applications, the elongate capsule has a length of between 50 mm and 90 mm.

In some applications, the capsule is configured such that airflow through the capsule is substantially in an axial direction along a length of the capsule.

In some applications, the metallic foil is configured to be heated via resistive heating by the first electrode driving a current to the second electrode along a length of more than 5 mm in an axial direction along the metallic foil. In some applications, the capsule is configured such that airflow through the capsule is substantially in the axial direction along a length of the capsule. In some applications, the metallic foil is configured to be heated via resistive heating by the first electrode driving a current to the second electrode along a length of more than 15 mm in the axial direction along the metallic foil.

In some applications, the metallic foil has a thickness of between 1 micron and 20 microns. In some applications, the metallic foil has a thickness of between 3 microns and 10 microns.

There is further provided, in accordance with some applications of the present invention, apparatus for use with a smoking device that includes at least first and second electrodes, the apparatus including:

a capsule including:
    a smoking material containing one or more active agents; and
    metallic foil surrounding the smoking material, the metallic foil being configured to be heated via resistive heating by the electrodes driving a current into the metallic foil; and
    a paper covering that covers the metallic foil,
    the paper covering being adhered to itself along a band of overlap, such as to form a cylindrical shape, and
    an electrically insulating material being disposed along the band of overlap, to isolate an inner layer of the metallic foil from the electrodes.

In some applications, the electrically insulating material includes an adhesive that is used to adhere the paper covering to itself along the band of overlap. In some applications, the electrically insulating material includes polyimide.

In some applications, the metallic foil is shaped such that at least a portion of the metallic foil is embedded within the smoking material.

In some applications, the metallic foil includes a plurality of regions, each of the regions having a respective, different electrical resistance profile, such that upon a given current being driven through the metallic foil each of the regions heats to a respective, different temperature.

In some applications, the capsule further includes a collapse-prevention element configured to facilitate electrical contact between the electrodes and the metallic foil, by preventing the capsule from collapsing.

In some applications, the capsule further includes an electrical-contact coating that coats the metallic foil at locations at which the electrodes are configured to contact the capsule.

In some applications, the metallic foil has a first configuration at locations at which the electrodes are configured to contact the metallic foil, and a second configuration along a region in which the metallic foil surrounds the smoking material that is between the locations at which the electrodes are configured to contact the metallic foil.

In some applications, the capsule further includes an inner lining that lines an inside of the metallic foil, the inner lining being configured to diffuse heat that is generated by the metallic foil.

In some applications, the smoking device includes one or more batteries, and an overall resistance to the current that is provided by the capsule is configured to substantially match an internal resistance of the one or more batteries of the smoking device.

In some applications, the paper covering defines openings via which the electrodes are configured to make electrical contact with the metallic foil.

In some applications, the paper covering is adhered to itself along a band of overlap, such as to form a cylindrical shape, and the metallic foil is treated along the band of overlap, in order to increase resistance of the metallic foil along the band of overlap.

In some applications, the capsule is shaped to define a cross-sectional shape having a ratio of more than 2:1 between a long side of the cross-sectional shape and a short side of the cross-sectional shape.

In some applications, at least a portion of the capsule is configured to be flattened by the smoking device prior to the one or more heating elements being heated by the smoking device. In some applications, the capsule has a circular cross-sectional shape and is configured to be flattened to define a non-circular cross-sectional shape. In some applications, the capsule is configured to be flattened such as to define a cross-sectional shape having a ratio of more than 2:1 between a long side of the cross-sectional shape and a short side of the cross-sectional shape.

In some applications, the capsule includes an elongate capsule having a length of between 15 mm and 150 mm. In some applications, the elongate capsule has a length of between 50 mm and 90 mm.

In some applications, the capsule is configured such that airflow through the capsule is substantially in an axial direction along a length of the capsule.

In some applications, the metallic foil is configured to be heated via resistive heating by the first electrode driving a current to the second electrode along a length of more than 5 mm in an axial direction along the metallic foil. In some applications, the capsule is configured such that airflow through the capsule is substantially in the axial direction along a length of the capsule. In some applications, the metallic foil is configured to be heated via resistive heating by the first electrode driving a current to the second electrode along a length of more than 15 mm in the axial direction along the metallic foil.

In some applications, the metallic foil has a thickness of between 1 micron and 20 microns. In some applications, the metallic foil has a thickness of between 3 microns and 10 microns.

There is further provided, in accordance with some applications of the present invention, apparatus for use with a smoking device that includes at least first and second electrodes, the apparatus including:
a capsule including:
a smoking material containing one or more active agents; and
metallic foil surrounding the smoking material, the metallic foil being configured to be heated via resistive heating by the electrodes driving a current into the metallic foil; and
a paper covering that covers the metallic foil,
the paper covering being adhered to itself along a band of overlap, such as to form a cylindrical shape, and the metallic foil being treated along the band of overlap, in order to increase resistance of the metallic foil along the band of overlap.

In some applications, the metallic foil defines slits along the band of overlap, in order to increase resistance of the metallic foil along the band of overlap.

In some applications, the metallic foil is shaped such that at least a portion of the metallic foil is embedded within the smoking material.

In some applications, the metallic foil includes a plurality of regions, each of the regions having a respective, different electrical resistance profile, such that upon a given current being driven through the metallic foil each of the regions heats to a respective, different temperature.

In some applications, the capsule further includes a collapse-prevention element configured to facilitate electrical contact between the electrodes and the metallic foil, by preventing the capsule from collapsing.

In some applications, the capsule further includes an electrical-contact coating that coats the metallic foil at locations at which the electrodes are configured to contact the capsule.

In some applications, the metallic foil has a first configuration at locations at which the electrodes are configured to contact the metallic foil, and a second configuration along a region in which the metallic foil surrounds the smoking material that is between the locations at which the electrodes are configured to contact the metallic foil.

In some applications, the capsule further includes an inner lining that lines an inside of the metallic foil, the inner lining being configured to diffuse heat that is generated by the metallic foil.

In some applications, the smoking device includes one or more batteries, and an overall resistance to the current that is provided by the capsule is configured to substantially match an internal resistance of the one or more batteries of the smoking device.

In some applications, the paper covering defines openings via which the electrodes are configured to make electrical contact with the metallic foil.

In some applications, the paper covering is adhered to itself along a band of overlap, such as to form a cylindrical shape, and an electrically insulating material is disposed along the band of overlap, to isolate an inner layer of the metallic foil from the electrodes.

In some applications, the capsule is shaped to define a cross-sectional shape having a ratio of more than 2:1 between a long side of the cross-sectional shape and a short side of the cross-sectional shape.

In some applications, at least a portion of the capsule is configured to be flattened by the smoking device prior to the one or more heating elements being heated by the smoking device. In some applications, the capsule has a circular cross-sectional shape and is configured to be flattened to define a non-circular cross-sectional shape. In some applications, the capsule is configured to be flattened such as to define a cross-sectional shape having a ratio of more than 2:1 between a long side of the cross-sectional shape and a short side of the cross-sectional shape.

In some applications, the capsule includes an elongate capsule having a length of between 15 mm and 150 mm. In some applications, the elongate capsule has a length of between 50 mm and 90 mm.

In some applications, the capsule is configured such that airflow through the capsule is substantially in an axial direction along a length of the capsule.

In some applications, the metallic foil is configured to be heated via resistive heating by the first electrode driving a current to the second electrode along a length of more than 5 mm in an axial direction along the metallic foil. In some applications, the capsule is configured such that airflow through the capsule is substantially in the axial direction along a length of the capsule. In some applications, the metallic foil is configured to be heated via resistive heating by the first electrode driving a current to the second electrode along a length of more than 15 mm in the axial direction along the metallic foil.

In some applications, the metallic foil has a thickness of between 1 micron and 20 microns. In some applications, the metallic foil has a thickness of between 3 microns and 10 microns.

There is therefore provided, in accordance with some applications of the present invention, apparatus for use with a cylindrically-shaped capsule that contains a smoking material containing one or more active agents, the apparatus including:

a smoking device configured to:

receive the cylindrically-shaped capsule that contains the smoking material;

flatten at least part of a portion of the capsule that contains the smoking material; and vaporize one or more of the active agents from within the smoking material by heating the smoking material while at least part of the portion of the capsule that contains the smoking material is flattened.

In some applications, the smoking device includes roller wheels that are configured to flatten at least part of the portion of the capsule that contains the smoking material upon the capsule being inserted into the smoking device. In some applications, the smoking device includes a funnel that is configured to flatten at least part of the portion of the capsule that contains the smoking material upon the capsule being inserted into the smoking device. In some applications, the smoking device includes mechanical elements that are configured to flatten at least part of the portion of the capsule that contains the smoking material by applying mechanical pressure to the capsule.

In some applications, the smoking device includes a control component configured to:

receive an indication from a user indicating whether they wish to smoke the active agents in a first mode or a second mode;

in response to receiving an indication that the user wishes to smoke the active agents in the first mode, heat the smoking material to a vaporization temperature of the one or more active agents for a predefined period of time; and in response to receiving an indication that the user wishes to smoke the active agents in the second mode, only heat the smoking material to the vaporization temperature while receiving an active input from the user that they wish for the smoking material to be heated.

In some applications, the control component is configured to preheat the smoking material to a temperature that is below the vaporization temperature of the one or more active agents, prior to receiving the indication from the user indicating whether they wish to smoke the active agents in the first mode or the second mode. In some applications, the control component is configured to preheat the smoking material to the temperature that is below the vaporization temperature of the one or more active agents automatically, in response to the capsule being inserted into the smoking device. In some applications, the control component is configured to preheat the smoking material to the temperature that is below the vaporization temperature of the one or more active agents, in response to an input from the user.

In some applications, the smoking device includes two or more electrodes that are configured to heat the smoking material by generating resistive heating within the capsule by driving a current through a portion of the capsule. In some applications, the electrodes are configured to move axially along a length of the capsule. In some applications, the smoking device includes a mechanism configured to bring the electrodes into pressurized contact with the capsule, in order to enhance electrical contact between the electrodes and the capsule.

In some applications, the capsule includes an elongate capsule, and during the heating of the smoking material, the smoking device is configured to house the capsule such that airflow through the capsule is substantially along a length of the elongate capsule, and a first one of the electrodes is configured to drive a current toward a second one of the electrodes along a length of more than 5 mm in an axial direction along a length of the capsule. In some applications, the first one of the electrodes is configured to drive the current toward the second one of the electrodes along a length of more than 15 mm in the axial direction along the length of the capsule.

In some applications, the smoking device is configured to receive a capsule that includes a metallic foil surrounding the smoking material, and the electrodes are configured to drive the current through the metallic foil. In some applications, the smoking device is configured to receive a capsule that includes a metallic foil surrounding the smoking material and a paper covering that covers the metallic foil, and the electrodes are needle shaped and are configured to make electrical contact with the metallic foil by piercing through the paper covering.

In some applications, the smoking device includes a coil that is configured to heat the smoking material by generating a magnetic field such as to heat the capsule via magnetic induction. In some applications, the coil is configured to be flattened while at least part of the portion of the capsule that contains the smoking material is disposed within the coil. In some applications, the coil is shaped to define a non-circular cross-sectional shape even before part of the portion of the capsule that contains the smoking material is introduced to within the coil, and the smoking device is configured to flatten the part of the portion of the capsule that contains the smoking material prior to the part of the portion of the capsule that contains the smoking material being introduced to within the coil.

In some applications, the smoking device is configured to receive a cylindrically-shaped elongate capsule having a length of between 15 mm and 150 mm. In some applications, the smoking device is configured to receive a cylindrically-shaped elongate capsule having a length of between 50 mm and 90 mm.

In some applications, the smoking device is configured to flatten the at least part of the portion of the capsule that contains the smoking material such that the part of the portion of the capsule that contains the smoking material defines a cross-sectional shape having a ratio of more than 2:1 between a long side of the cross-sectional shape and a short side of the cross-sectional shape. In some applications, the smoking device is configured to flatten the at least part of the portion of the capsule that contains the smoking material such that the part of the portion of the capsule that contains the smoking material defines a cross-sectional shape having a ratio of more than 3:1 between a long side of the cross-sectional shape and a short side of the cross-sectional shape. In some applications, the smoking device is configured to flatten the at least part of the portion of the capsule that contains the smoking material such that the part of the portion of the capsule that contains the smoking material defines a cross-sectional shape having a ratio of more than 4:1 between a long side of the cross-sectional shape and a short side of the cross-sectional shape. In some applications, the smoking device is configured to flatten the at least part of the portion of the capsule that contains the smoking material such that the part of the portion of the capsule that contains the smoking material defines a cross-sectional shape having a ratio of more than 6:1 between a long side of the cross-sectional shape and a short side of the cross-sectional shape.

There is further provided, in accordance with some applications of the present invention, apparatus for use with a cylindrically-shaped capsule that contains a smoking material containing one or more active agents, the apparatus including:

a smoking device configured to vaporize one or more of the active agents from within the smoking material by heating the smoking material, the smoking device including:

a cylindrically-shaped insertion port configured to receive the cylindrically-shaped capsule that contains the smoking material; and a non-cylindrical housing configured to house at least part of a portion of the capsule that contains the smoking material, while the smoking device heats the smoking material.

In some applications, the smoking device includes roller wheels that are configured to flatten at least part of the portion of the capsule that contains the smoking material upon the capsule being inserted into the smoking device. In some applications, the smoking device includes a funnel that is configured to flatten at least part of the portion of the capsule that contains the smoking material upon the capsule being inserted into the smoking device. In some applications, the smoking device includes mechanical elements that are configured to flatten at least part of the portion of the capsule that contains the smoking material by applying mechanical pressure to the capsule.

In some applications, the smoking device includes a control component configured to:

receive an indication from a user indicating whether they wish to smoke the active agents in a first mode or a second mode;

in response to receiving an indication that the user wishes to smoke the active agents in the first mode, heat the smoking material to a vaporization temperature of the one or more active agents for a predefined period of time; and in response to receiving an indication that the user wishes to smoke the active agents in the second mode, only heat the smoking material to the vaporization temperature while receiving an active input from the user that they wish for the smoking material to be heated.

In some applications, the control component is configured to preheat the smoking material to a temperature that is below the vaporization temperature of the one or more active agents, prior to receiving the indication from the user indicating whether they wish to smoke the active agents in the first mode or the second mode. In some applications, the control component is configured to preheat the smoking material to the temperature that is below the vaporization temperature of the one or more active agents automatically, in response to the capsule being inserted into the smoking device. In some applications, the control component is configured to preheat the smoking material to the temperature that is below the vaporization temperature of the one or more active agents, in response to an input from the user.

In some applications, the smoking device includes a coil that is configured to heat the smoking material by generating a magnetic field such as to heat the capsule via magnetic induction. In some applications, the coil is configured to be flattened while at least part of the portion of the capsule that contains the smoking material is disposed within the coil. In some applications, the coil is shaped to define a non-circular cross-sectional shape even before part of the portion of the capsule that contains the smoking material is introduced to within the coil, and the smoking device is configured to flatten the part of the portion of the capsule that contains the smoking material prior to the part of the portion of the capsule that contains the smoking material being introduced to within the coil.

In some applications, the non-cylindrical housing defines a cross-sectional shape having a ratio of more than 2:1 between a long side of the cross-sectional shape and a short side of the cross-sectional shape. In some applications, the non-cylindrical housing defines a cross-sectional shape having a ratio of more than 3:1 between a long side of the cross-sectional shape and a short side of the cross-sectional shape. In some applications, the non-cylindrical housing defines a cross-sectional shape having a ratio of more than 4:1 between a long side of the cross-sectional shape and a short side of the cross-sectional shape. In some applications, the non-cylindrical housing defines a cross-sectional shape having a ratio of more than 6:1 between a long side of the cross-sectional shape and a short side of the cross-sectional shape.

In some applications, the smoking device is configured to receive a cylindrically-shaped elongate capsule having a length of between 15 mm and 150 mm. In some applications, the smoking device is configured to receive a cylindrically-shaped elongate capsule having a length of between 50 mm and 90 mm.

In some applications, the smoking device includes two or more electrodes that are configured to heat the smoking material by generating resistive heating within the capsule by driving a current through a portion of the capsule. In some applications, the electrodes are configured to move axially along a length of the capsule. In some applications, the smoking device includes a mechanism configured to bring the electrodes into pressurized contact with the capsule, in order to enhance electrical contact between the electrodes and the capsule.

In some applications, the capsule includes an elongate capsule, during the heating of the smoking material, the smoking device is configured to house the capsule such that airflow through the capsule is substantially along a length of the elongate capsule, and a first one of the electrodes is configured to drive the current toward a second one of the electrodes along a length of more than 5 mm in an axial direction along a length of the capsule. In some applications, the first one of the electrodes is configured to drive the current toward the second one of the electrodes along a length of more than 15 mm in the axial direction along the length of the capsule.

In some applications, the smoking device is configured to receive a capsule that includes a metallic foil surrounding the smoking material, and the electrodes are configured to drive the current through the metallic foil. In some applications, the smoking device is configured to receive a capsule that includes a metallic foil surrounding the smoking material and a paper covering that covers the metallic foil and the electrodes are needle shaped and are configured to make electrical contact with the metallic foil by piercing through the paper covering.

There is further provided, in accordance with some applications of the present invention, apparatus for use with a capsule that contains a smoking material containing one or more active agents, the apparatus including:

a smoking device configured to vaporize one or more of the active agents from within the smoking material by heating the smoking material, the smoking device including:

two or more sensors, each of which is configured to detect a temperature of the capsule at the same location along a length of the capsule as each other.

In some applications, the sensors are configured to be placed on respective sides of the capsule. In some applications, the sensors include infrared temperature sensors. In some applications, the sensors include thermocouple sensors. In some applications, the sensors include contact sensors that are configured to contact the smoking material. In some applications, the sensors are configured to move axially along a length of the capsule.

In some applications, the smoking device includes a control component configured to:

receive an indication from a user indicating whether they wish to smoke the active agents in a first mode or a second mode;

in response to receiving an indication that the user wishes to smoke the active agents in the first mode, heat the smoking material to a vaporization temperature of the one or more active agents for a predefined period of time; and in response to receiving an indication that the user wishes to smoke the active agents in the second mode, only heat the smoking material to the vaporization temperature while receiving an active input from the user that they wish for the smoking material to be heated.

In some applications, the control component is configured to preheat the smoking material to a temperature that is below the vaporization temperature of the one or more active agents, prior to receiving the indication from the user indicating whether they wish to smoke the active agents in the first mode or the second mode. In some applications, the control component is configured to preheat the smoking material to the temperature that is below the vaporization temperature of the one or more active agents automatically, in response to the capsule being inserted into the smoking device. In some applications, the control component is configured to preheat the smoking material to the temperature that is below the vaporization temperature of the one or more active agents, in response to an input from the user.

In some applications, the apparatus further includes a control component configured to determine a temperature of the smoking material at the location along the length of the capsule based upon the temperatures detected by each of the sensors. In some applications, the control component is configured to determine an average temperature of the smoking material at the location along the length of the capsule based upon the temperatures detected by each of the sensors. In some applications, the control component is configured to determine a maximum temperature of the smoking material at the location along the length of the capsule based upon the temperatures detected by each of the sensors. In some applications, the control component is configured to determine a minimum temperature of the smoking material at the location along the length of the capsule based upon the temperatures detected by each of the sensors. In some applications, the control component is configured to determine a temperature range of the smoking material at the location along the length of the capsule based upon the temperatures detected by each of the sensors. In some applications, based upon the temperatures detected by each of the sensors, the control component is configured to determine that the temperature detected by a first one of the sensors is indicative of a fault with the first one of the sensors, and, in response thereto, the control component is configured to determine the temperature of the smoking material based upon the temperature detect by a second one of the sensors.

In some applications, the control component is configured to control heating of the smoking material in response to the determined temperature of the smoking material. In some applications, the control component is configured to control heating of the smoking material such as to maintain the smoking material within a predefined temperature range.

In some applications, the smoking device includes:

two or more electrodes that are configured to heat the smoking material by generating resistive heating within the capsule by driving a current through a portion of the capsule; and a control component that is configured to detect an amount of current that must be applied to the capsule in order to maintain the smoking material at a substantially constant temperature and to thereby detect that the user has puffed the smoking device.

In some applications, the control component is configured to determine a parameter of the puff. In some applications, the control component is configured to determine a length of the puff. In some applications, the control component is configured to determine a depth of the puff. In some applications, the control component is configured to determine an amount of one or more of the active agents that has been vaporized from the capsule by monitoring a number of puffs and parameters of the puffs that have been taken from the capsule.

There is further provided, in accordance with some applications of the present invention, apparatus for use with a capsule that contains a smoking material containing one or more active agents, the apparatus including:

a smoking device configured to vaporize one or more of the active agents from within the smoking material by heating the smoking material, the smoking device including:

one or more sensors configured to detect temperature of the smoking material within the capsule and configured to be moveable axially along a length of the capsule.

In some applications, the sensor includes an infrared temperature sensor. In some applications, the sensor includes a thermocouple sensor. In some applications, the sensor includes a contact sensor that is configured to contact the smoking material.

In some applications, the smoking device includes two or more electrodes that are configured to heat the smoking material by driving a current through the capsule, and the two or more electrodes are configured to configured to be moveable axially along the length of the capsule together with the one or more sensors. In some applications, the smoking device includes a motor and a rail and the motor is configured to move the one or more sensors axially along the length of the capsule by sliding the one or more sensors along the rail.

In some applications, the smoking device includes a control component configured to:

receive an indication from a user indicating whether they wish to smoke the active agents in a first mode or a second mode;

in response to receiving an indication that the user wishes to smoke the active agents in the first mode, heat the smoking material to a vaporization temperature of the one or more active agents for a predefined period of time; and in response to receiving an indication that the user wishes to smoke the active agents in the second mode, only heat the smoking material to the vaporization temperature while receiving an active input from the user that they wish for the smoking material to be heated.

In some applications, the control component is configured to preheat the smoking material to a temperature that is below the vaporization temperature of the one or more active agents, prior to receiving the indication from the user indicating whether they wish to smoke the active agents in the first mode or the second mode. In some applications, the control component is configured to preheat the smoking material to the temperature that is below the vaporization temperature of the one or more active agents automatically, in response to the capsule being inserted into the smoking device. In some applications, the control component is configured to preheat the smoking material to the temperature that is below the vaporization temperature of the one or more active agents, in response to an input from the user.

In some applications, the sensor includes two or more sensors, each of which is configured to detect a temperature of the capsule at the same location along a length of the capsule as each other, at a given time. In some applications, the sensors are configured to be placed on respective sides of the capsule. In some applications, the apparatus further includes a control component configured to determine a temperature of the smoking material at the location along the length of the capsule based upon the temperatures detected by the sensors. In some applications, the control component is configured to determine an average temperature of the smoking material at the location along the length of the capsule based upon the temperatures detected by each of the sensors. In some applications, the control component is configured to determine a maximum temperature of the smoking material at the location along the length of the capsule based upon the temperatures detected by each of the sensors. In some applications, the control component is configured to determine a minimum temperature of the smoking material at the location along the length of the capsule based upon the temperatures detected by each of the sensors. In some applications, the control component is configured to determine a temperature range of the smoking material at the location along the length of the capsule based upon the temperatures detected by each of the sensors. In some applications, based upon the temperatures detected by each of the sensors the control component is configured to determine that the temperature detected by a first one of the sensors is indicative of a fault with the first one of the sensors, and, in response thereto, the control component is configured to determine the temperature of the smoking material based upon the temperature detect by a second one of the sensors.

In some applications, the apparatus further includes a control component configured to determine a temperature of the smoking material based upon the temperature detected by the sensor. In some applications, the control component is configured to control heating of the smoking material in response to the determined temperature of the smoking material. In some applications, the control component is configured to control heating of the smoking material such as to maintain the smoking material within a predefined temperature range.

In some applications, the smoking device includes:

two or more electrodes that are configured to heat the smoking material by generating resistive heating within the capsule by driving a current through a portion of the capsule; and a control component that is configured to detect an amount of current that must be applied to the capsule in order to maintain the smoking material at a substantially constant temperature and to thereby detect that the user has puffed the smoking device.

In some applications, the control component is configured to determine a parameter of the puff. In some applications, the control component is configured to determine a length of the puff. In some applications, the control component is configured to determine a depth of the puff. In some applications, the control component is configured to determine an amount of one or more of the active agents that has been vaporized from the capsule by monitoring a number of puffs and parameters of the puffs that have been taken from the capsule.

There is further provided, in accordance with some applications of the present invention, apparatus for use with a capsule that contains a smoking material containing one or more active agents, the apparatus including:

a smoking device configured to vaporize one or more of the active agents from within the smoking material by heating the smoking material, the smoking device including a control component configured to:

receive an indication from a user indicating whether they wish to smoke the active agents in a first mode or a second mode;

in response to receiving an indication that the user wishes to smoke the active agents in the first mode, heat the smoking material to a vaporization temperature of the one or more active agents for a predefined period of time; and in response to receiving an indication that the user wishes to smoke the active agents in the second mode, heat the smoking material to the vaporization temperature only while receiving an active input from the user that they wish for the smoking material to be heated.

In some applications, the control component is configured, in response to receiving an indication that the user wishes to smoke the active agents in the first mode, to heat the smoking material to the vaporization temperature for a predefined period of time that is between 60 seconds and 600 seconds.

In some applications, the smoking device includes a button configured to be pressed by a user, and the control component is configured such that:

the user pressing the button for a duration that is less than a threshold duration, is interpreted by the control component that the user wishes to smoke the active agents in the second mode; and the user pressing the button for a duration that is more than the threshold duration, is interpreted by the control component that the user wishes to smoke the active agents in the first mode.

In some applications, the control component is configured to preheat the smoking material to a temperature that is below the vaporization temperature of the one or more active agents, prior to receiving the indication from the user indicating whether they wish to smoke the active agents in the first mode or the second mode. In some applications, the control component is configured to preheat the smoking material to the temperature that is below the vaporization temperature of the one or more active agents automatically, in response to the capsule being inserted into the smoking device. In some applications, the control component is configured to preheat the smoking material to the temperature that is below the vaporization temperature of the one or more active agents, in response to an input from the user.

In some applications, the smoking device includes a button configured to be pressed by a user, and the control component is configured such that:

the user pressing the button for a duration that is less than a threshold duration, is interpreted by the control component that the user wishes to smoke the active agents in the first mode; and the user pressing the button for a duration that is more than the threshold duration, is interpreted by the control component that the user wishes to smoke the active agents in the second mode.

In some applications, the threshold duration is between 0 and 2 seconds.

In some applications, the smoking device is configured such that during a smoking session, the user can switch from the first mode to the second mode by pressing the button for more than the threshold duration.

In some applications, the smoking device is configured such that during a smoking session, the user can switch from the second mode to the first mode by pressing the button for less than the threshold duration.

In some applications, the smoking device is configured to:

flatten at least part of a portion of the capsule that contains the smoking material; and vaporize one or more of the active agents from within the smoking material by heating the smoking material while at least part of the portion of the capsule that contains the smoking material is in a flattened configuration.

In some applications, the smoking device includes roller wheels that are configured to flatten at least part of the portion of the capsule that contains the smoking material upon the capsule being inserted into the smoking device. In some applications, the smoking device includes a funnel that is configured to flatten at least part of the portion of the capsule that contains the smoking material upon the capsule being inserted into the smoking device. In some applications, the smoking device includes mechanical elements that are configured to flatten at least part of the portion of the capsule that contains the smoking material by applying mechanical pressure to the capsule.

In some applications, the smoking device is configured to flatten the at least part of the portion of the capsule that contains the smoking material such that the part of the portion of the capsule that contains the smoking material defines a cross-sectional shape having a ratio of more than 2:1 between a long side of the cross-sectional shape and a short side of the cross-sectional shape. In some applications, the smoking device is configured to flatten the at least part of the portion of the capsule that contains the smoking material such that the part of the portion of the capsule that contains the smoking material defines a cross-sectional shape having a ratio of more than 3:1 between a long side of the cross-sectional shape and a short side of the cross-sectional shape. In some applications, the smoking device is configured to flatten the at least part of the portion of the capsule that contains the smoking material such that the part of the portion of the capsule that contains the smoking material defines a cross-sectional shape having a ratio of more than 4:1 between a long side of the cross-sectional shape and a short side of the cross-sectional shape. In some applications, the smoking device is configured to flatten the at least part of the portion of the capsule that contains the smoking material such that the part of the portion of the capsule that contains the smoking material defines a cross-sectional shape having a ratio of more than 6:1 between a long side of the cross-sectional shape and a short side of the cross-sectional shape.

In some applications, the smoking device includes two or more electrodes that are configured to heat the smoking material by generating resistive heating within the capsule by driving a current through a portion of the capsule. In some applications, the electrodes are configured to move axially along a length of the capsule. In some applications, the smoking device includes a mechanism configured to bring the electrodes into pressurized contact with the capsule, in order to enhance electrical contact between the electrodes and the capsule.

In some applications, the capsule includes an elongate capsule, during the heating of the smoking material, the smoking device is configured to house the capsule such that airflow through the capsule is substantially along a length of the elongate capsule, and a first one of the electrodes is configured to drive the current toward a second one of the electrodes along a length of more than 5 mm in an axial direction along a length of the capsule. In some applications, the first one of the electrodes is configured to drive the current toward the second one of the electrodes along a length of more than 15 mm in the axial direction along a length of the capsule.

In some applications, the smoking device is configured to receive a capsule that includes a metallic foil surrounding the smoking material, and the electrodes are configured to drive a current through the metallic foil. In some applications, the smoking device is configured to receive a capsule that includes a metallic foil surrounding the smoking material and a paper covering that covers the metallic foil and the electrodes are needle shaped and are configured to make electrical contact with the metallic foil by piercing through the paper covering.

In some applications, the smoking device includes a coil that is configured to heat the smoking material by generating a magnetic field such as to heat the capsule via magnetic induction. In some applications, the coil is configured to be flattened while at least part of the portion of the capsule that contains the smoking material is disposed within the coil. In some applications, the coil is shaped to define a non-circular cross-sectional shape even before part of the portion of the capsule that contains the smoking material is introduced to within the coil, and the smoking device is configured to flatten the part of the portion of the capsule that contains the smoking material prior to the part of the portion of the capsule that contains the smoking material being introduced to within the coil.

In some applications, the smoking device is configured to receive a cylindrically-shaped elongate capsule having a length of between 15 mm and 150 mm. In some applications, the smoking device is configured to receive a cylindrically-shaped elongate capsule having a length of between 50 mm and 90 mm.

There is further provided, in accordance with some applications of the present invention, apparatus for use with a capsule that contains a smoking material containing one or more active agents, the apparatus including:

a smoking device configured to vaporize one or more of the active agents from within the smoking material by heating the smoking material, the smoking device including:

roller wheels that are configured to change a shape of the capsule upon the capsule being inserted into the smoking device.

There is further provided, in accordance with some applications of the present invention, apparatus for use with a capsule that contains a smoking material containing one or more active agents, the apparatus including:

a smoking device configured to vaporize one or more of the active agents from within the smoking material by heating the smoking material, the smoking device including:

a funnel that is configured to change a shape of the capsule upon the capsule being inserted into the smoking device.

There is further provided, in accordance with some applications of the present invention, apparatus for use with a capsule that contains a smoking material containing one or more active agents, the apparatus including:

a smoking device configured to vaporize one or more of the active agents from within the smoking material by heating the smoking material, the smoking device including:

a control component configured to:

detect an amount of current that is required to maintain the smoking material at a given temperature;

thereby derive an indication of an amount of the one or more active agents that has been vaporized; and terminate heating of the smoking material in response to detecting an indication that more than a given amount of the one or more of the active agents has been vaporized.

There is further provided, in accordance with some applications of the present invention, apparatus for use with a capsule that contains a smoking material containing one or more active agents, the apparatus including:

a smoking device configured to vaporize one or more of the active agents from within the smoking material by heating the smoking material, the smoking device including:

an electrode configured to drive a current into the capsule at one or more locations on the capsule;

a sensor configured to detect an amount of resistance that is generated by the capsule at the one or more locations; and a control component configured to derive identifying information regarding the capsule based on the amount of resistance that is generated by the capsule at the one or more locations.

There is further provided, in accordance with some applications of the present invention, apparatus for use with a capsule that contains a smoking material containing one or more active agents, the apparatus including:

a smoking device configured to receive the capsule, the smoking device including: two or more electrodes that are configured to:

change a shape of the capsule upon the capsule being inserted into the smoking device, by exerting mechanical pressure upon the capsule; and vaporize one or more of the active agents from within the smoking material by heating the smoking material, by driving a current through a portion of the capsule.

In some applications, the electrodes are configured to move axially along a length of the capsule. In some applications, the smoking device includes a mechanism configured to bring the electrodes into pressurized contact with the capsule, in order to enhance electrical contact between the electrodes and the capsule.

In some applications, the smoking device includes a control component configured to:

receive an indication from a user indicating whether they wish to smoke the active agents in a first mode or a second mode;

in response to receiving an indication that the user wishes to smoke the active agents in the first mode, heat the smoking material to a vaporization temperature of the one or more active agents for a predefined period of time; and in response to receiving an indication that the user wishes to smoke the active agents in the second mode, only heat the smoking material to the vaporization temperature while receiving an active input from the user that they wish for the smoking material to be heated.

In some applications, the control component is configured to preheat the smoking material to a temperature that is below the vaporization temperature of the one or more active agents, prior to receiving the indication from the user indicating whether they wish to smoke the active agents in the first mode or the second mode. In some applications, the control component is configured to preheat the smoking material to the temperature that is below the vaporization temperature of the one or more active agents automatically, in response to the capsule being inserted into the smoking device. In some applications, the control component is configured to preheat the smoking material to the temperature that is below the vaporization temperature of the one or more active agents, in response to an input from the user.

In some applications, the smoking device is configured to receive a capsule that includes a metallic foil surrounding the smoking material, and the electrodes are configured to drive a current through the metallic foil. In some applications, the smoking device is configured to receive a capsule that includes a metallic foil surrounding the smoking material and a paper covering that covers the metallic foil and the electrodes are needle shaped and are configured to make electrical contact with the metallic foil by piercing through the paper covering.

In some applications, the smoking device is configured to receive an elongate capsule, during the heating of the smoking material, the smoking device is configured to house the capsule such that airflow through the capsule is substantially along a length of the elongate capsule, and a first one of the electrodes is configured to drive a current toward a second one of the electrodes along a length of more than 5 mm in an axial direction along a length of the capsule. In some applications, the first one of the electrodes is configured to drive the current toward the second one of the electrodes along a length of more than 15 mm in the axial direction along the length of the capsule.

In some applications, the smoking device is configured to receive a cylindrically-shaped elongate capsule having a length of between 15 mm and 150 mm. In some applications, the smoking device is configured to receive a cylindrically-shaped elongate capsule having a length of between 50 mm and 90 mm.

In some applications, the electrodes are configured to flatten at least a part of a portion of the capsule that contains the smoking material such that the part of the portion of the capsule that contains the smoking material defines a cross-sectional shape having a ratio of more than 2:1 between a long side of the cross-sectional shape and a short side of the cross-sectional shape. In some applications, the electrodes are configured to flatten at least a part of a portion of the capsule that contains the smoking material such that the part of the portion of the capsule that contains the smoking material defines a cross-sectional shape having a ratio of more than 3:1 between a long side of the cross-sectional shape and a short side of the cross-sectional shape. In some applications, the electrodes are configured to flatten at least a part of a portion of the capsule that contains the smoking material such that the part of the portion of the capsule that contains the smoking material defines a cross-sectional shape having a ratio of more than 4:1 between a long side of the cross-sectional shape and a short side of the cross-sectional shape. In some applications, the electrodes are configured to flatten at least a part of a portion of the capsule that contains the smoking material such that the part of the portion of the capsule that contains the smoking material defines a cross-sectional shape having a ratio of more than 6:1 between a long side of the cross-sectional shape and a short side of the cross-sectional shape.

There is further provided, in accordance with some applications of the present invention, apparatus for use with a capsule that contains a smoking material containing one or more active agents, the apparatus including:

a smoking device configured to receive the capsule, the smoking device including:

two or more electrodes that are configured to:

vaporize one or more of the active agents from within the smoking material by heating the smoking material, by driving a current into a portion of the capsule; and move axially along a length of the capsule.

In some applications, the smoking device is configured to receive a cylindrically-shaped capsule, and the smoking device includes a cylindrically-shaped insertion port configured to receive the cylindrically-shaped capsule and a non-cylindrical housing configured to house at least part of a portion of the capsule that contains the smoking material, while the smoking material is heated.

In some applications, the smoking device includes a mechanism configured to bring the electrodes into pressurized contact with the capsule, in order to enhance electrical contact between the electrodes and the capsule.

In some applications, the smoking device includes one or more sensors configured to detect temperature of the smoking material within the capsule, and the one or more sensors are configured to configured to be moveable axially along the length of the capsule together with the two or more electrodes.

In some applications, the smoking device includes a motor and a rail and the motor is configured to move the two or more electrodes axially along the length of the capsule by sliding the two or more electrodes along the rail.

In some applications, the smoking device includes a control component configured to:

receive an indication from a user indicating whether they wish to smoke the active agents in a first mode or a second mode;

in response to receiving an indication that the user wishes to smoke the active agents in the first mode, heat the smoking material to a vaporization temperature of the one or more active agents for a predefined period of time; and in response to receiving an indication that the user wishes to smoke the active agents in the second mode, only heat the smoking material to the vaporization temperature while receiving an active input from the user that they wish for the smoking material to be heated.

In some applications, the control component is configured to preheat the smoking material to a temperature that is below the vaporization temperature of the one or more active agents, prior to receiving the indication from the user indicating whether they wish to smoke the active agents in the first mode or the second mode. In some applications, the control component is configured to preheat the smoking material to the temperature that is below the vaporization temperature of the one or more active agents automatically, in response to the capsule being inserted into the smoking device. In some applications, the control component is configured to preheat the smoking material to the temperature that is below the vaporization temperature of the one or more active agents, in response to an input from the user.

In some applications, the smoking device is configured to receive a capsule that includes a metallic foil surrounding the smoking material, and the electrodes are configured to drive a current through the metallic foil. In some applications, the smoking device is configured to receive a capsule that includes a metallic foil surrounding the smoking material and a paper covering that covers the metallic foil and the electrodes are needle shaped and are configured to make electrical contact with the metallic foil by piercing through the paper covering.

In some applications, the smoking device is configured to receive an elongate capsule, during the heating of the smoking material, the smoking device is configured to house the capsule such that airflow through the capsule is substantially along a length of the elongate capsule, and a first one of the electrodes is configured to drive the current toward a second one of the electrodes along a length of more than 5 mm in an axial direction along a length of the capsule. In some applications, the first one of the electrodes is configured to drive the current toward the second one of the electrodes along a length of more than 15 mm in the axial direction along a length of the capsule.

In some applications, the smoking device is configured to receive a cylindrically-shaped elongate capsule having a length of between 15 mm and 150 mm. In some applications, the smoking device is configured to receive a cylindrically-shaped elongate capsule having a length of between 50 mm and 90 mm.

In some applications, the electrodes are configured to change a shape of the capsule upon the capsule being inserted into the smoking device, by exerting mechanical pressure upon the capsule. In some applications, the electrodes are configured to flatten at least a part of a portion of the capsule that contains the smoking material such that the part of the portion of the capsule that contains the smoking material defines a cross-sectional shape having a ratio of more than 2:1 between a long side of the cross-sectional shape and a short side of the cross-sectional shape. In some applications, the electrodes are configured to flatten at least a part of a portion of the capsule that contains the smoking material such that the part of the portion of the capsule that contains the smoking material defines a cross-sectional shape having a ratio of more than 3:1 between a long side of the cross-sectional shape and a short side of the cross-sectional shape. In some applications, the electrodes are configured to flatten at least a part of a portion of the capsule that contains the smoking material such that the part of the portion of the capsule that contains the smoking material defines a cross-sectional shape having a ratio of more than 4:1 between a long side of the cross-sectional shape and a short side of the cross-sectional shape. In some applications, the electrodes are configured to flatten at least a part of a portion of the capsule that contains the smoking material such that the part of the portion of the capsule that contains the smoking material defines a cross-sectional shape having a ratio of more than 6:1 between a long side of the cross-sectional shape and a short side of the cross-sectional shape.

In some applications, the smoking device is configured to flatten at least part of a portion of the capsule that contains the smoking material. In some applications, the smoking device includes roller wheels that are configured to flatten at least part of the portion of the capsule that contains the smoking material upon the capsule being inserted into the smoking device. In some applications, the smoking device includes a funnel that is configured to flatten at least part of the portion of the capsule that contains the smoking material upon the capsule being inserted into the smoking device. In some applications, the smoking device includes mechanical elements that are configured to flatten at least part of the portion of the capsule that contains the smoking material by applying mechanical pressure to the capsule.

There is further provided, in accordance with some applications of the present invention, apparatus for use with a capsule that contains a smoking material containing one or more active agents, the smoking material being covered with a metallic foil, the apparatus including:

a smoking device configured to receive the capsule, the smoking device including:
two or more electrodes that are configured to vaporize one or more of the active agents from within the smoking material by heating the smoking material, by driving a current into the metallic foil; and
a mechanism configured to bring the electrodes into pressurized contact with the capsule, in order to enhance electrical contact between the electrodes and the metallic foil of the capsule.

In some applications, the smoking device is configured to receive a cylindrically-shaped capsule, and the smoking device includes a cylindrically-shaped insertion port configured to receive the cylindrically-shaped capsule and a non-cylindrical housing configured to house at least part of a portion of the capsule that contains the smoking material, while the smoking material is heated.

In some applications, the electrodes are configured to move axially along a length of the capsule.

In some applications, the smoking device includes a control component configured to:
receive an indication from a user indicating whether they wish to smoke the active agents in a first mode or a second mode;
in response to receiving an indication that the user wishes to smoke the active agents in the first mode, heat the smoking material to a vaporization temperature of the one or more active agents for a predefined period of time; and
in response to receiving an indication that the user wishes to smoke the active agents in the second mode, only heat the smoking material to the vaporization temperature while receiving an active input from the user that they wish for the smoking material to be heated.

In some applications, the control component is configured to preheat the smoking material to a temperature that is below the vaporization temperature of the one or more active agents, prior to receiving the indication from the user indicating whether they wish to smoke the active agents in the first mode or the second mode. In some applications, the control component is configured to preheat the smoking material to the temperature that is below the vaporization temperature of the one or more active agents automatically, in response to the capsule being inserted into the smoking device. In some applications, the control component is configured to preheat the smoking material to the temperature that is below the vaporization temperature of the one or more active agents, in response to an input from the user.

In some applications, the smoking device is configured to receive a capsule that includes a metallic foil surrounding the smoking material, and the electrodes are configured to drive a current through the metallic foil. In some applications, the smoking device is configured to receive a capsule that includes a metallic foil surrounding the smoking material and a paper covering that covers the metallic foil and the electrodes are needle shaped and are configured to make electrical contact with the metallic foil by piercing through the paper covering.

In some applications, the smoking device is configured to receive an elongate capsule, during the heating of the smoking material, the smoking device is configured to house the capsule such that airflow through the capsule is substantially along a length of the elongate capsule, and a first one of the electrodes is configured to drive the current toward a second one of the electrodes along a length of more than 5 mm in an axial direction along a length of the capsule. In some applications, the first one of the electrodes is configured to drive the current toward the second one of the electrodes along a length of more than 15 mm in the axial direction along the length of the capsule.

In some applications, the smoking device is configured to receive a cylindrically-shaped elongate capsule having a length of between 15 mm and 150 mm. In some applications, the smoking device is configured to receive a cylindrically-shaped elongate capsule having a length of between 50 mm and 90 mm.

In some applications, the electrodes are configured to change a shape of the capsule upon the capsule being inserted into the smoking device, by exerting mechanical pressure upon the capsule. In some applications, the electrodes are configured to flatten at least a part of a portion of the capsule that contains the smoking material such that the part of the portion of the capsule that contains the smoking material defines a cross-sectional shape having a ratio of more than 2:1 between a long side of the cross-sectional shape and a short side of the cross-sectional shape. In some applications, the electrodes are configured to flatten at least a part of a portion of the capsule that contains the smoking material such that the part of the portion of the capsule that contains the smoking material defines a cross-sectional shape having a ratio of more than 3:1 between a long side of the cross-sectional shape and a short side of the cross-sectional shape. In some applications, the electrodes are configured to flatten at least a part of a portion of the capsule that contains the smoking material such that the part of the portion of the capsule that contains the smoking material defines a cross-sectional shape having a ratio of more than 4:1 between a long side of the cross-sectional shape and a short side of the cross-sectional shape. In some applications, the electrodes are configured to flatten at least a part of a portion of the capsule that contains the smoking material such that the part of the portion of the capsule that contains the smoking material defines a cross-sectional shape having a ratio of more than 6:1 between a long side of the cross-sectional shape and a short side of the cross-sectional shape.

In some applications, the smoking device is configured to flatten at least part of a portion of the capsule that contains the smoking material. In some applications, the smoking device includes roller wheels that are configured to flatten at least part of the portion of the capsule that contains the smoking material upon the capsule being inserted into the smoking device. In some applications, the smoking device includes a funnel that is configured to flatten at least part of the portion of the capsule that contains the smoking material upon the capsule being inserted into the smoking device.

In some applications, the smoking device includes mechanical elements that are configured to flatten at least part of the portion of the capsule that contains the smoking material by applying mechanical pressure to the capsule. In some applications, the mechanism configured to bring the electrodes into pressurized contact with the capsule includes one or more compression springs that are configured to generate a counterforce in response to being compressed.

In some applications:

the smoking device includes a button that is coupled to a gear track; and the smoking device is configured such that:

insertion of the capsule requires the button to be pressed, and pressing of the button causes compression of the compression springs, such that upon release of the button, the compression springs bring the electrodes into pressurized contact with the capsule.

There is further provided, in accordance with some applications of the present invention, apparatus for use with a capsule that contains a smoking material containing one or more active agents, the smoking material being covered with a metallic foil and a paper covering, the apparatus including:

a smoking device configured to receive the capsule, the smoking device including:

two or more electrodes that are configured to vaporize one or more of the active agents from within the smoking material by heating the smoking material, by driving a current into the metallic foil, the two or more electrodes being needle shaped and being configured to make electrical contact with the metallic foil by piercing through the paper covering.

In some applications, the smoking device is configured to receive a cylindrically-shaped capsule, and the smoking device includes a cylindrically-shaped insertion port configured to receive the cylindrically-shaped capsule and a non-cylindrical housing configured to house at least part of a portion of the capsule that contains the smoking material, while the smoking material is heated.

In some applications, the electrodes are configured to move axially along a length of the capsule.

In some applications, the smoking device includes a mechanism configured to bring the electrodes into pressurized contact with the capsule, in order to enhance electrical contact between the electrodes and the capsule.

In some applications, the smoking device includes a control component configured to:

receive an indication from a user indicating whether they wish to smoke the active agents in a first mode or a second mode;

in response to receiving an indication that the user wishes to smoke the active agents in the first mode, heat the smoking material to a vaporization temperature of the one or more active agents for a predefined period of time; and in response to receiving an indication that the user wishes to smoke the active agents in the second mode, only heat the smoking material to the vaporization temperature while receiving an active input from the user that they wish for the smoking material to be heated.

In some applications, the control component is configured to preheat the smoking material to a temperature that is below the vaporization temperature of the one or more active agents, prior to receiving the indication from the user indicating whether they wish to smoke the active agents in the first mode or the second mode. In some applications, the control component is configured to preheat the smoking material to the temperature that is below the vaporization temperature of the one or more active agents automatically, in response to the capsule being inserted into the smoking device. In some applications, the control component is configured to preheat the smoking material to the temperature that is below the vaporization temperature of the one or more active agents, in response to an input from the user.

In some applications, the smoking device is configured to receive an elongate capsule, during the heating of the smoking material, the smoking device is configured to house the capsule such that airflow through the capsule is substantially along a length of the elongate capsule, and a first one of the electrodes is configured to drive the current toward a second one of the electrodes along a length of more than 5 mm in an axial direction along a length of the capsule. In some applications, the first one of the electrodes is configured to drive the current toward the second one of the electrodes along a length of more than 15 mm in the axial direction along the length of the capsule.

In some applications, the smoking device is configured to receive a cylindrically-shaped elongate capsule having a length of between 15 mm and 150 mm. In some applications, the smoking device is configured to receive a cylindrically-shaped elongate capsule having a length of between 50 mm and 90 mm.

In some applications, the electrodes are configured to change a shape of the capsule upon the capsule being inserted into the smoking device, by exerting mechanical pressure upon the capsule. In some applications, the electrodes are configured to flatten at least a part of a portion of the capsule that contains the smoking material such that the part of the portion of the capsule that contains the smoking material defines a cross-sectional shape having a ratio of more than 2:1 between a long side of the cross-sectional shape and a short side of the cross-sectional shape. In some applications, the electrodes are configured to flatten at least a part of a portion of the capsule that contains the smoking material such that the part of the portion of the capsule that contains the smoking material defines a cross-sectional shape having a ratio of more than 3:1 between a long side of the cross-sectional shape and a short side of the cross-sectional shape. In some applications, the electrodes are configured to flatten at least a part of a portion of the capsule that contains the smoking material such that the part of the portion of the capsule that contains the smoking material defines a cross-sectional shape having a ratio of more than 4:1 between a long side of the cross-sectional shape and a short side of the cross-sectional shape. In some applications, the electrodes are configured to flatten at least a part of a portion of the capsule that contains the smoking material such that the part of the portion of the capsule that contains the smoking material defines a cross-sectional shape having a ratio of more than 6:1 between a long side of the cross-sectional shape and a short side of the cross-sectional shape.

In some applications, the smoking device is configured to flatten at least part of a portion of the capsule that contains the smoking material. In some applications, the smoking device includes roller wheels that are configured to flatten at least part of the portion of the capsule that contains the smoking material upon the capsule being inserted into the smoking device. In some applications, the smoking device includes a funnel that is configured to flatten at least part of the portion of the capsule that contains the smoking material upon the capsule being inserted into the smoking device. In some applications, the smoking device includes mechanical elements that are configured to flatten at least part of the portion of the capsule that contains the smoking material by applying mechanical pressure to the capsule.

There is further provided, in accordance with some applications of the present invention, apparatus for use with an elongate capsule that contains a smoking material containing one or more active agents, the smoking material being covered with a metallic foil, the apparatus including:

a smoking device including:

a receptacle configured to house the elongate capsule such that airflow through the capsule is substantially along a length of the elongate capsule;

first and second electrodes that are configured to vaporize one or more of the active agents from within the smoking material by heating the smoking material, by the first electrode driving a current toward the second electrode along a length of the metallic foil of more than 5 mm in an axial direction along a length of the capsule.

In some applications, the first and second electrodes are configured to vaporize one or more of the active agents from within the smoking material by heating the smoking material, by the first electrode driving the current toward the second electrode along a length of the metallic foil of more than 15 mm in the axial direction along the length of the capsule.

In some applications, the smoking device is configured to receive a cylindrically-shaped capsule, and the smoking device includes a cylindrically-shaped insertion port configured to receive the cylindrically-shaped capsule and a non-cylindrical housing configured to house at least part of a portion of the capsule that contains the smoking material, while the smoking material is heated.

In some applications, the smoking device includes a mechanism configured to bring the electrodes into pressurized contact with the capsule, in order to enhance electrical contact between the electrodes and the capsule.

In some applications, the electrodes are configured to move axially along a length of the capsule.

In some applications, the smoking device is configured to receive a capsule that includes the metallic foil surrounding the smoking material and a paper covering that covers the metallic foil, and the electrodes are needle shaped and are configured to make electrical contact with the metallic foil by piercing through the paper covering.

In some applications, the smoking device includes a control component configured to:

receive an indication from a user indicating whether they wish to smoke the active agents in a first mode or a second mode;

in response to receiving an indication that the user wishes to smoke the active agents in the first mode, heat the smoking material to a vaporization temperature of the one or more active agents for a predefined period of time; and in response to receiving an indication that the user wishes to smoke the active agents in the second mode, only heat the smoking material to the vaporization temperature while receiving an active input from the user that they wish for the smoking material to be heated.

In some applications, the control component is configured to preheat the smoking material to a temperature that is below the vaporization temperature of the one or more active agents, prior to receiving the indication from the user indicating whether they wish to smoke the active agents in the first mode or the second mode. In some applications, the control component is configured to preheat the smoking material to the temperature that is below the vaporization temperature of the one or more active agents automatically, in response to the capsule being inserted into the smoking device. In some applications, the control component is configured to preheat the smoking material to the temperature that is below the vaporization temperature of the one or more active agents, in response to an input from the user.

In some applications, the smoking device is configured to receive an elongate capsule having a length of between 15 mm and 150 mm. In some applications, the smoking device is configured to receive an elongate capsule having a length of between 50 mm and 90 mm.

In some applications, the electrodes are configured to change a shape of the capsule upon the capsule being inserted into the smoking device, by exerting mechanical pressure upon the capsule. In some applications, the electrodes are configured to flatten at least a part of a portion of the capsule that contains the smoking material such that the part of the portion of the capsule that contains the smoking material defines a cross-sectional shape having a ratio of more than 2:1 between a long side of the cross-sectional shape and a short side of the cross-sectional shape. In some applications, the electrodes are configured to flatten at least a part of a portion of the capsule that contains the smoking material such that the part of the portion of the capsule that contains the smoking material defines a cross-sectional shape having a ratio of more than 3:1 between a long side of the cross-sectional shape and a short side of the cross-sectional shape. In some applications, the electrodes are configured to flatten at least a part of a portion of the capsule that contains the smoking material such that the part of the portion of the capsule that contains the smoking material defines a cross-sectional shape having a ratio of more than 4:1 between a long side of the cross-sectional shape and a short side of the cross-sectional shape. In some applications, the electrodes are configured to flatten at least a part of a portion of the capsule that contains the smoking material such that the part of the portion of the capsule that contains the smoking material defines a cross-sectional shape having a ratio of more than 6:1 between a long side of the cross-sectional shape and a short side of the cross-sectional shape.

In some applications, the smoking device is configured to flatten at least part of a portion of the capsule that contains the smoking material. In some applications, the smoking device includes roller wheels that are configured to flatten at least part of the portion of the capsule that contains the smoking material upon the capsule being inserted into the smoking device. In some applications, the smoking device includes a funnel that is configured to flatten at least part of the portion of the capsule that contains the smoking material upon the capsule being inserted into the smoking device. In some applications, the smoking device includes mechanical elements that are configured to flatten at least part of the portion of the capsule that contains the smoking material by applying mechanical pressure to the capsule.

There is further provided, in accordance with some applications of the present invention, apparatus for use with a cylindrically-shaped capsule that contains a smoking material containing one or more active agents, the apparatus including:

a smoking device including:

one or more mechanical elements configured to flatten at least a portion of the capsule;

a coil receive at least the portion the capsule, when the portion of the capsule is in a flattened configuration; and a power source configured to vaporize one or more of the active agents from within the smoking material by heating the smoking material via magnetic induction, by driving a current into the coil.

In some applications, the smoking device includes roller wheels that are configured to flatten at least part of the portion of the capsule that contains the smoking material upon the capsule being inserted into the smoking device. In some applications, the smoking device includes a funnel that is configured to flatten at least part of the portion of the capsule that contains the smoking material upon the capsule being inserted into the smoking device.

In some applications, the smoking device includes a control component configured to:

receive an indication from a user indicating whether they wish to smoke the active agents in a first mode or a second mode;

in response to receiving an indication that the user wishes to smoke the active agents in the first mode, heat the smoking material to a vaporization temperature of the one or more active agents for a predefined period of time; and in response to receiving an indication that the user wishes to smoke the active agents in the second mode, only heat the smoking material to the vaporization temperature while receiving an active input from the user that they wish for the smoking material to be heated.

In some applications, the control component is configured to preheat the smoking material to a temperature that is below the vaporization temperature of the one or more active agents, prior to receiving the indication from the user indicating whether they wish to smoke the active agents in the first mode or the second mode. In some applications, the control component is configured to preheat the smoking material to the temperature that is below the vaporization temperature of the one or more active agents automatically, in response to the capsule being inserted into the smoking device. In some applications, the control component is configured to preheat the smoking material to the temperature that is below the vaporization temperature of the one or more active agents, in response to an input from the user.

In some applications, the coil has a non-circular cross-sectional shape having a ratio of more than 2:1 between a long side of the cross-sectional shape and a short side of the cross-sectional shape. In some applications, the coil has a non-circular cross-sectional shape having a ratio of more than 3:1 between a long side of the cross-sectional shape and a short side of the cross-sectional shape. In some applications, the coil has a non-circular cross-sectional shape having a ratio of more than 4:1 between a long side of the cross-sectional shape and a short side of the cross-sectional shape. In some applications, the coil has a non-circular cross-sectional shape having a ratio of more than 6:1 between a long side of the cross-sectional shape and a short side of the cross-sectional shape.

In some applications, the smoking device is configured to flatten the at least part of the portion of the capsule that contains the smoking material such that the part of the portion of the capsule that contains the smoking material defines a cross-sectional shape having a ratio of more than 2:1 between a long side of the cross-sectional shape and a short side of the cross-sectional shape. In some applications, the smoking device is configured to flatten the at least part of the portion of the capsule that contains the smoking material such that the part of the portion of the capsule that contains the smoking material defines a cross-sectional shape having a ratio of more than 3:1 between a long side of the cross-sectional shape and a short side of the cross-sectional shape. In some applications, the smoking device is configured to flatten the at least part of the portion of the capsule that contains the smoking material such that the part of the portion of the capsule that contains the smoking material defines a cross-sectional shape having a ratio of more than 4:1 between a long side of the cross-sectional shape and a short side of the cross-sectional shape. In some applications, the smoking device is configured to flatten the at least part of the portion of the capsule that contains the smoking material such that the part of the portion of the capsule that contains the smoking material defines a cross-sectional shape having a ratio of more than 6:1 between a long side of the cross-sectional shape and a short side of the cross-sectional shape.

In some applications, the smoking device is configured to receive a cylindrically-shaped elongate capsule having a length of between 15 mm and 150 mm. In some applications, the smoking device is configured to receive a cylindrically-shaped elongate capsule having a length of between 50 mm and 90 mm.

There is further provided, in accordance with some applications of the present invention, apparatus for use with a capsule that contains a smoking material containing one or more active agents, the apparatus including:

a smoking device including:

a coil configured to receive at least part of a portion of the capsule that contains the smoking material;

a mechanical element configured to flatten at least a portion the coil while the portion of the capsule is disposed within the coil, such as to flatten the portion of the capsule; and a power source configured to vaporize one or more of the active agents from within the smoking material by heating the smoking material via magnetic induction, by driving a current into the coil while the portion of the coil and the portion of the capsule are in flattened configurations.

In some applications, the smoking device includes roller wheels that are configured to flatten the portion the coil while the portion of the capsule is disposed within the coil.

In some applications, the smoking device includes a control component configured to:

receive an indication from a user indicating whether they wish to smoke the active agents in a first mode or a second mode;

in response to receiving an indication that the user wishes to smoke the active agents in the first mode, heat the smoking material to a vaporization temperature of the one or more active agents for a predefined period of time; and in response to receiving an indication that the user wishes to smoke the active agents in the second mode, only heat the smoking material to the vaporization temperature while receiving an active input from the user that they wish for the smoking material to be heated.

In some applications, the control component is configured to preheat the smoking material to a temperature that is below the vaporization temperature of the one or more active agents, prior to receiving the indication from the user indicating whether they wish to smoke the active agents in the first mode or the second mode. In some applications, the control component is configured to preheat the smoking material to the temperature that is below the vaporization temperature of the one or more active agents automatically, in response to the capsule being inserted into the smoking device. In some applications, the control component is configured to preheat the smoking material to the temperature that is below the vaporization temperature of the one or more active agents, in response to an input from the user.

In some applications, the smoking device is configured to flatten the at least part of the portion of the capsule that contains the smoking material such that the part of the portion of the capsule that contains the smoking material defines a cross-sectional shape having a ratio of more than 2:1 between a long side of the cross-sectional shape and a short side of the cross-sectional shape. In some applications, the smoking device is configured to flatten the at least part of the portion of the capsule that contains the smoking material such that the part of the portion of the capsule that contains the smoking material defines a cross-sectional shape having a ratio of more than 3:1 between a long side of the cross-sectional shape and a short side of the cross-sectional shape. In some applications, the smoking device is configured to flatten the at least part of the portion of the capsule that contains the smoking material such that the part of the portion of the capsule that contains the smoking material defines a cross-sectional shape having a ratio of more than 4:1 between a long side of the cross-sectional shape and a short side of the cross-sectional shape. In some applications, the smoking device is configured to flatten the at least part of the portion of the capsule that contains the smoking material such that the part of the portion of the capsule that contains the smoking material defines a cross-sectional shape having a ratio of more than 6:1 between a long side of the cross-sectional shape and a short side of the cross-sectional shape.

In some applications, the smoking device is configured to receive a cylindrically-shaped elongate capsule having a length of between 15 mm and 150 mm. In some applications, the smoking device is configured to receive a cylindrically-shaped elongate capsule having a length of between 50 mm and 90 mm.

There is further provided, in accordance with some applications of the present invention, apparatus for use with a capsule that contains a smoking material containing one or more active agents, the apparatus including:

a smoking device including:

a coil having a non-circular cross-sectional shape and configured to receive at least a portion the capsule; and a power source configured to vaporize one or more of the active agents from within the smoking material by heating the smoking material via magnetic induction, by driving a current into the coil, a magnetic flux density generated within the coil being greater than that generated by a coil having a similar perimeter and a circular shape.

In some applications, the smoking device includes a control component configured to:

receive an indication from a user indicating whether they wish to smoke the active agents in a first mode or a second mode;

in response to receiving an indication that the user wishes to smoke the active agents in the first mode, heat the smoking material to a vaporization temperature of the one or more active agents for a predefined period of time; and in response to receiving an indication that the user wishes to smoke the active agents in the second mode, only heat the smoking material to the vaporization temperature while receiving an active input from the user that they wish for the smoking material to be heated.

In some applications, the control component is configured to preheat the smoking material to a temperature that is below the vaporization temperature of the one or more active agents, prior to receiving the indication from the user indicating whether they wish to smoke the active agents in the first mode or the second mode. In some applications, the control component is configured to preheat the smoking material to the temperature that is below the vaporization temperature of the one or more active agents automatically, in response to the capsule being inserted into the smoking device. In some applications, the control component is configured to preheat the smoking material to the temperature that is below the vaporization temperature of the one or more active agents, in response to an input from the user.

In some applications, the coil has a non-circular cross-sectional shape having a ratio of more than 2:1 between a long side of the cross-sectional shape and a short side of the cross-sectional shape. In some applications, the coil has a non-circular cross-sectional shape having a ratio of more than 3:1 between a long side of the cross-sectional shape and a short side of the cross-sectional shape. In some applications, the coil has a non-circular cross-sectional shape having a ratio of more than 4:1 between a long side of the cross-sectional shape and a short side of the cross-sectional shape. In some applications, the coil has a non-circular cross-sectional shape having a ratio of more than 6:1 between a long side of the cross-sectional shape and a short side of the cross-sectional shape.

In some applications, the smoking device includes one or more mechanical elements configured to flatten at least part of a portion of the capsule that contains the smoking material. In some applications, the smoking device includes roller wheels that are configured to flatten at least part of the portion of the capsule that contains the smoking material upon the capsule being inserted into the smoking device. In some applications, the smoking device includes a funnel that is configured to flatten at least part of the portion of the capsule that contains the smoking material upon the capsule being inserted into the smoking device.

In some applications, the smoking device is configured to flatten the at least part of the portion of the capsule that contains the smoking material such that the part of the portion of the capsule that contains the smoking material defines a cross-sectional shape having a ratio of more than 2:1 between a long side of the cross-sectional shape and a short side of the cross-sectional shape. In some applications, the smoking device is configured to flatten the at least part of the portion of the capsule that contains the smoking material such that the part of the portion of the capsule that contains the smoking material defines a cross-sectional shape having a ratio of more than 3:1 between a long side of the cross-sectional shape and a short side of the cross-sectional shape. In some applications, the smoking device is configured to flatten the at least part of the portion of the capsule that contains the smoking material such that the part of the portion of the capsule that contains the smoking material defines a cross-sectional shape having a ratio of more than 4:1 between a long side of the cross-sectional shape and a short side of the cross-sectional shape. In some applications, the smoking device is configured to flatten the at least part of the portion of the capsule that contains the smoking material such that the part of the portion of the capsule that contains the smoking material defines a cross-sectional shape having a ratio of more than 6:1 between a long side of the cross-sectional shape and a short side of the cross-sectional shape.

In some applications, the smoking device is configured to receive a cylindrically-shaped elongate capsule having a length of between 15 mm and 150 mm. In some applications, the smoking device is configured to receive a cylindrically-shaped elongate capsule having a length of between 50 mm and 90 mm.

There is further provided, in accordance with some applications of the present invention, apparatus for use with a capsule that contains a smoking material containing one or more active agents, the apparatus including:

a smoking device including:

a material configured to form a magnetic circuit and defining a gap within the circuit, the gap being sized such as to receive a portion of the capsule;

a coil disposed around a portion of the magnetic circuit; and a power source configured to vaporize one or more of the active agents from within the smoking material by heating the smoking material via magnetic induction, by driving a current into the coil while portion of the capsule is disposed within the gap.

In some applications, the smoking device includes a control component configured to:

receive an indication from a user indicating whether they wish to smoke the active agents in a first mode or a second mode;

in response to receiving an indication that the user wishes to smoke the active agents in the first mode, heat the smoking material to a vaporization temperature of the one or more active agents for a predefined period of time; and in response to receiving an indication that the user wishes to smoke the active agents in the second mode, only heat the smoking material to the vaporization temperature while receiving an active input from the user that they wish for the smoking material to be heated.

In some applications, the control component is configured to preheat the smoking material to a temperature that is below the vaporization temperature of the one or more active agents, prior to receiving the indication from the user indicating whether they wish to smoke the active agents in the first mode or the second mode. In some applications, the control component is configured to preheat the smoking material to the temperature that is below the vaporization temperature of the one or more active agents automatically, in response to the capsule being inserted into the smoking device. In some applications, the control component is configured to preheat the smoking material to the temperature that is below the vaporization temperature of the one or more active agents, in response to an input from the user.

In some applications, the smoking device is configured to flatten the portion of the capsule, and the gap is sized such as to receive the portion of the capsule when the portion of the capsule is in a flattened configuration.

In some applications, magnetic permeability of the circuit is increased by virtue of the gap being sized such as to receive the portion of the capsule when the portion of the capsule is in a flattened configuration relative to if the gap were sized such as to receive the capsule in a non-flattened configuration.

In some applications, the smoking device includes roller wheels that are configured to flatten at least part of the portion of the capsule that contains the smoking material upon the capsule being inserted into the smoking device. In some applications, the smoking device includes a funnel that is configured to flatten at least part of the portion of the capsule that contains the smoking material upon the capsule being inserted into the smoking device. In some applications, the smoking device includes one or more mechanical elements that are configured to flatten at least part of the portion of the capsule that contains the smoking material upon the capsule being inserted into the smoking device.

In some applications, the smoking device is configured to flatten the at least part of the portion of the capsule that contains the smoking material such that the part of the portion of the capsule that contains the smoking material defines a cross-sectional shape having a ratio of more than 2:1 between a long side of the cross-sectional shape and a short side of the cross-sectional shape. In some applications, the smoking device is configured to flatten the at least part of the portion of the capsule that contains the smoking material such that the part of the portion of the capsule that contains the smoking material defines a cross-sectional shape having a ratio of more than 3:1 between a long side of the cross-sectional shape and a short side of the cross-sectional shape. In some applications, the smoking device is configured to flatten the at least part of the portion of the capsule that contains the smoking material such that the part of the portion of the capsule that contains the smoking material defines a cross-sectional shape having a ratio of more than 4:1 between a long side of the cross-sectional shape and a short side of the cross-sectional shape. In some applications, the smoking device is configured to flatten the at least part of the portion of the capsule that contains the smoking material such that the part of the portion of the capsule that contains the smoking material defines a cross-sectional shape having a ratio of more than 6:1 between a long side of the cross-sectional shape and a short side of the cross-sectional shape.

In some applications, the smoking device is configured to receive a cylindrically-shaped elongate capsule having a length of between 15 mm and 150 mm. In some applications, the smoking device is configured to receive a cylindrically-shaped elongate capsule having a length of between 50 mm and 90 mm.

The present invention will be more fully understood from the following detailed description of applications thereof, taken together with the drawings, in which:

BRIEF DESCRIPTION OF THE DRAWINGS

FIGS. 18A, 18B, and 18C are schematic illustrations of a capsule including a mouthpiece, in accordance with some applications of the present invention;

DETAILED DESCRIPTION OF EMBODIMENTS

Figure 1A:
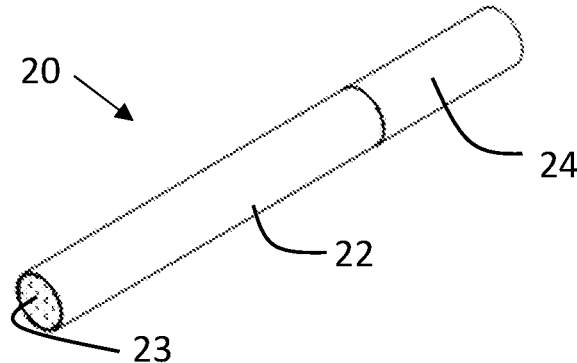
FIGS. 1A, 1B, 1C, and 1D are schematic illustrations of a capsule (FIGS. 1A-B), a smoking device (FIG. 1C), and the capsule inserted in the smoking device (FIG. 1D), in accordance with some applications of the present invention.
Figure 1B:
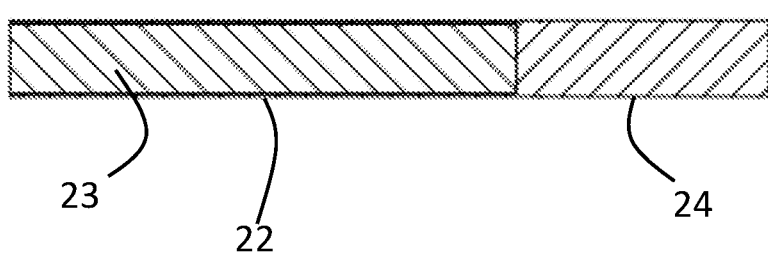
Figure 1C:
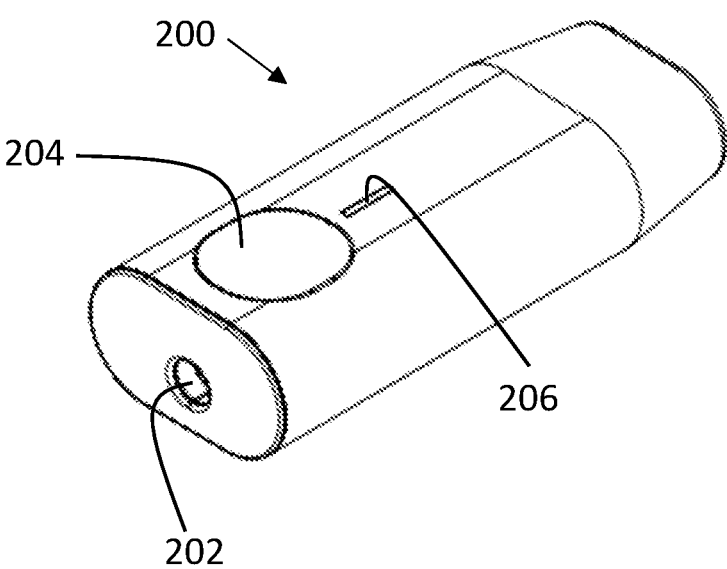
Figure 1D:
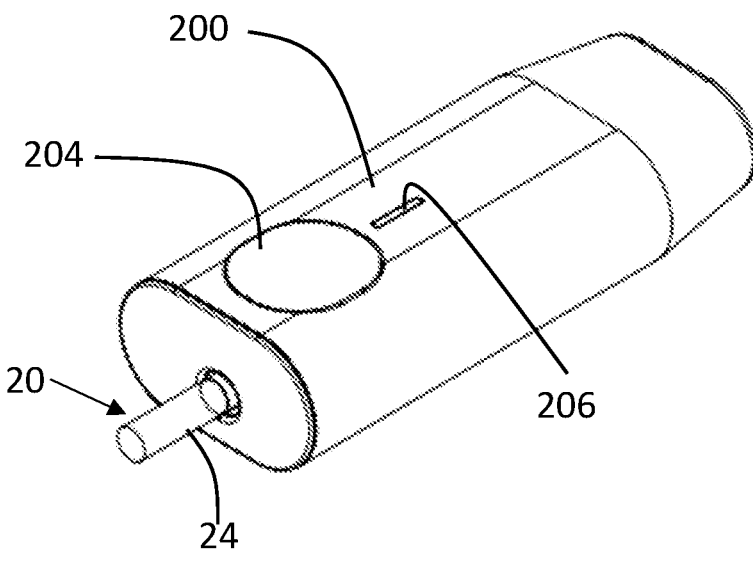

Reference is now made to FIGS. 1A, 1B, 1C, and 1D, which are schematic illustrations of a capsule 20 (FIGS. 1A-B), a smoking device 200 (FIG. 1C), and the capsule inserted in the smoking device (FIG. 1D), in accordance with some applications of the present invention. (It is noted that the term "smoking device" is used herein to describe device 200, since this terminology is used in the art. However, device 200 may also be referred to as a "vaping device.") Typically, the capsule is a disposable capsule that is configured to be used during a single smoking session, whereas the smoking device is configured to be reusable. Capsule 20 typically has the general structure (e.g., shape and/or size) of a traditional cigarette. Many users and manufacturers of such capsule and smoking devices have a preference for single-use capsules having the general structure of a traditional cigarette, due to (a) habitual preferences of the users, (b) habitual preferences of the manufacturers, (c) production lines of the manufacturers being best-equipped to manufacture such capsules relative to capsules that differ from traditional cigarettes, (d) single-use capsules being more hygienic than capsules that are designed for repeated use, and/or (e) additional reasons.

Typically, capsule 20 includes a first portion 22 that contains a smoking material 23 (that contains active agents) and a heating element (as described in further detail hereinbelow). Smoking material 23 is typically a plant material, such as tobacco and/or a cannabinoid-containing plant material (such as marijuana). For some applications, the smoking material is a non-plant material that contains active agents. (It is noted that, in some of the figures (e.g., FIGS. 6A-7D, 9A-B, and 10B-14), the smoking material is not shaded, for illustrative purposes. However, all of the figures showing a capsule should be interpreted to be showing a capsule that contains smoking material.) The capsule is typically inserted into a slot 202 within smoking device 200. Smoking device 200 is configured to heat the smoking material, such as to generate vapors containing active agents within the smoking material in a heat-not-burn manner. The user typically sucks the generated vapors out of a second portion 24 of the capsule that functions as a mouthpiece.

As described hereinabove in the Background, heat-not-burn smoking devices (also known as "smokeless" devices) are devices that heat a smoking material without burning (i.e., pyrolyzing) the smoking material. The user sucks in vaporized active agents that are generated. An important element in heat-not-burn smoking devices is that time that it takes to heat the smoking material and the uniformity of the heating. The time that it takes to heat up the smoking material is defined by the following equation:

$$t = Q*d/(K*A*\Delta T) \qquad \text{[Equation 1]}$$

where t is the time taken to heat the smoking material,

Q is the quantity of heat transferred to the smoking material, d is the distance from the location at which the heat is generated to the smoking material that is being heated, K is the constant that defines the heat conduction of the smoking material (which is relatively low for smoking materials as they are relatively non-conductive), and any other material between the heating element and the smoking material, A is the area of contact between the heating element and the smoking material, and T is temperature change that is applied at the heating element.

There are several challenges to heating up smoking material in a heat-not-burn process, including the following:

low heat conduction of the smoking material (i.e., a low value of K in Equation 1);

a limited temperature to which the heating element can be heated in order to avoid pyrolysis (i.e., burning) of the smoking material (i.e., a low value of $\Delta T$ in Equation 1);

many designs of heating-elements-capsule combinations providing a relatively small area of contact between the heating elements and the smoking material (i.e., a low value of A in Equation 1), particularly if the capsule is designed to have the general shape of a traditional cigarette;

in order to provide the appearance and feel of a traditional cigarette, there may be a heat-insulating material (e.g., paper) between the heating element and the smoking material (thereby further decreasing K in Equation 1), for example, if heating is applied by a heating element that is disposed within the smoking device outside the capsule;

the distance from the heating element to the smoking material that is located toward the radial center of the capsule is relatively large (i.e., a high value of d in Equation 1).

In accordance with some applications of the present invention, apparatus and methods are provided that (a) provide a relatively large area of contact between the heating element and the smoking material (i.e., A in Equation 1), and (b) provide a relatively small distance between the heating element and the smoking material even at the radial center of the capsule (i.e., d in Equation 1), while (c) providing the user with a capsule having the same general structure as a traditional cigarette.

Typically, the heating element is built-in to the capsule, such that it is in direct contact with smoking material 23. For some applications, at least some of the heating element is embedded within the smoking material, as described in further detail hereinbelow. For some applications, the heating element comprises a metal material (such as metallic foil, e.g., stainless steel foil, nickel-titanium foil, titanium foil, copper foil, aluminum foil, steel foil), which is typically disposed within the capsule and/or is typically in direct contact with the smoking material, and that is heated via electrical resistive heating, as described in further detail hereinbelow. Alternatively or additionally, the heating element comprises one or more magnetically-heated materials that are susceptible to being heated by a magnetic field (such as, magnetic materials and/or ferromagnetic materials), which are typically disposed within the capsule and/or are typically in direct contact with smoking material and that are heated via magnetic induction, as described in further detail hereinbelow.

Typically, the capsule is an elongate capsule. For some applications, the elongate capsule has a length of between 15 mm and 150 mm (e.g., between 50 mm and 90 mm). For some applications, the capsule has the same general structure as a traditional cigarette, but differs from the general structure of a cigarette in that the capsule is provided to the user with at least a portion of the capsule having a shape that is flattened relative to a traditional cigarette (e.g., such that it has an elliptical, rectangular, pill-shaped, or racetrack-shaped cross-sectional shape). Typically, by being flattened, the smoking material that is disposed toward the radial center of the capsule is disposed closer to the heating element than if the capsule had a circular cross section with a similar cross-sectional area, as described in further detail hereinbelow. Alternatively, the capsule is provided to the user with a circular cross-section shape, typically having a diameter of between 4 mm and 12 mm (e.g., between 5 and 8.5 mm). Typically, for such applications, although the capsule is provided to the user with the capsule having a circular cross-sectional shape, at least a portion of the capsule is flattened upon being inserted into the smoking device (e.g., such that it has an elliptical, rectangular, pill-shaped, or racetrack-shaped cross-sectional shape), such that the smoking material that was disposed toward the radial center of the capsule is disposed closer to the heating element than it would have been before being flattened, as described in further detail hereinbelow.

Figures 2A, 2B:
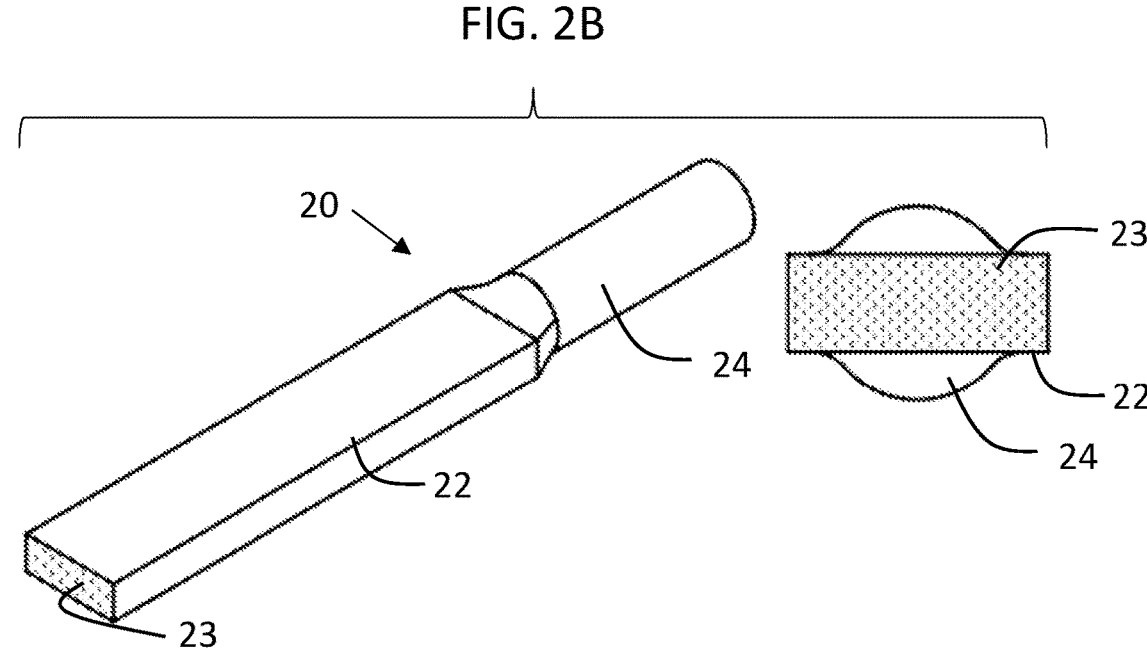
FIGS. 2A, 2B, 2C, and 2D are schematic illustrations of isometric views and end views of the capsule, with a portion of the capsule that contains smoking material and a heating element having a shape that is flattened relative to a traditional cigarette, such that it has an elliptical cross-sectional shape (FIG. 2A), a rectangular cross-sectional shape (FIG. 2B), a pill-shaped cross-sectional shape (FIG. 2C), or a racetrack-shaped cross-sectional shape (FIG. 2D), in accordance with some applications of the present invention.
Figures 2C, 2D:
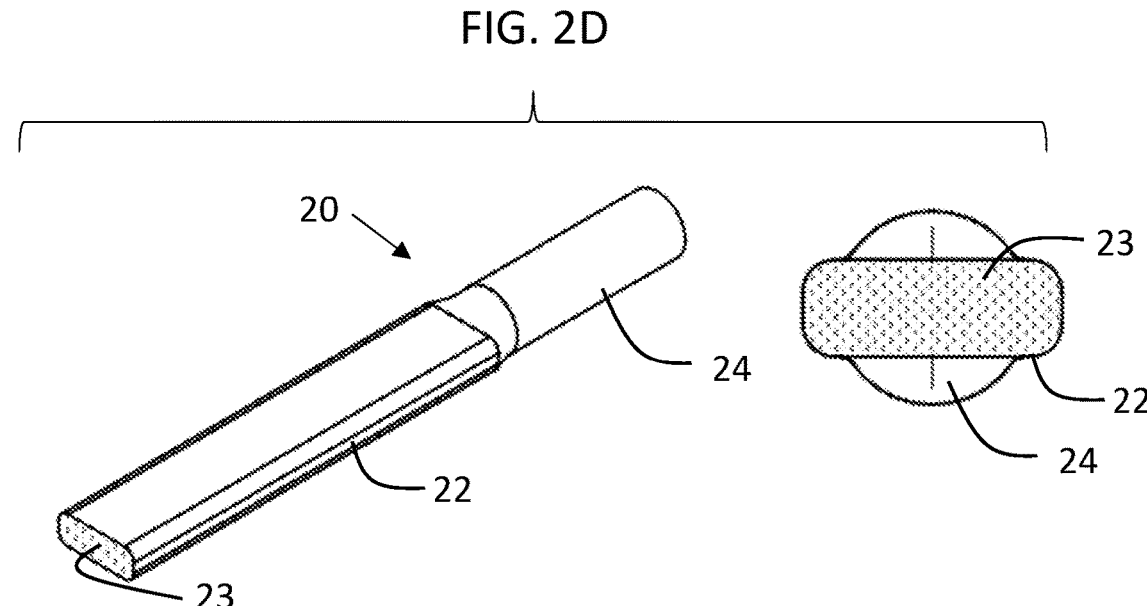

Reference is now made to FIGS. 2A, 2B, 2C, and 2D, which are schematic illustrations of isometric views and end views of capsule 20, with a portion 22 of the capsule that contains the smoking material and the heating element having a shape that is flattened relative to a traditional cigarette, such that it has an elliptical cross-sectional shape (FIG. 2A), a rectangular cross-sectional shape (FIG. 2B), a pill-shaped cross-sectional shape (FIG. 2C), or a racetrack-shaped cross-sectional shape (FIG. 2D). (Each of FIGS. 2A-D shows an isometric view and an end view of the capsule.) Typically, portion 24 of the capsule that serves as the mouthpiece has a circular cross-sectional shape. As described hereinabove, for some applications, the capsule is provided to the user with portion 22 of the capsule having a shape that is flattened relative to a traditional cigarette. Alternatively, the capsule is provided to the user with portion 22 of the capsule having a circular cross-sectional shape, but all or part of portion 22 of the capsule is flattened upon being inserted into the smoking device. For some applications, at least a part of portion 22 is flattened such that a ratio between the long side of the cross-sectional shape and the short side of the cross-sectional shape is greater than 2:1, 3:1, 4:1, or 6:1. Typically, the heating elements are disposed at least along the long sides of portion 22, such that the distance between the heating elements and the smoking material is less than if portion 22 had a circular cross-sectional shape with a similar perimeter.

Figure 3A:
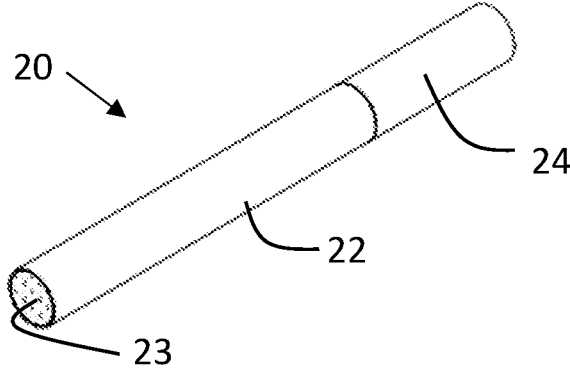
FIGS. 3A, 3B, and 3C are schematic illustrations of, respectively, a capsule having a circular cross-section, a capsule that has been flattened by having pressure applied to the capsule at discrete locations along its length, and a capsule that has been flattened along the entire length of the portion of the capsule that contains smoking material and a heating element, in accordance with some applications of the present invention.
Figure 3B:
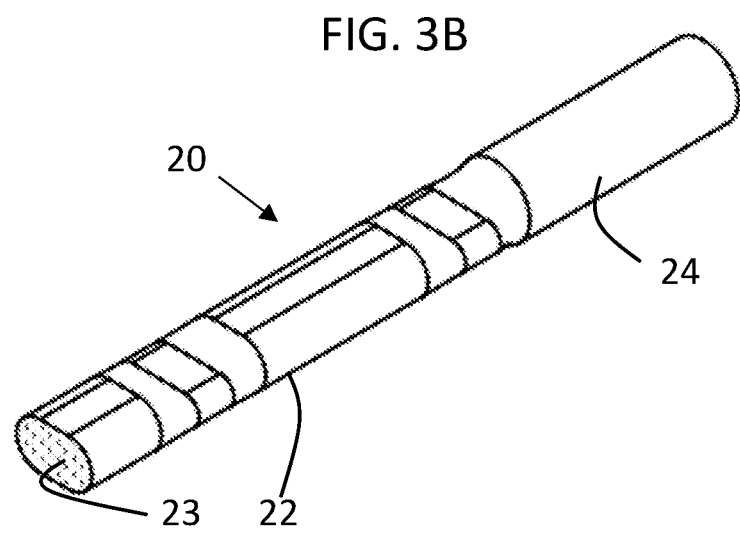
Figure 3C:
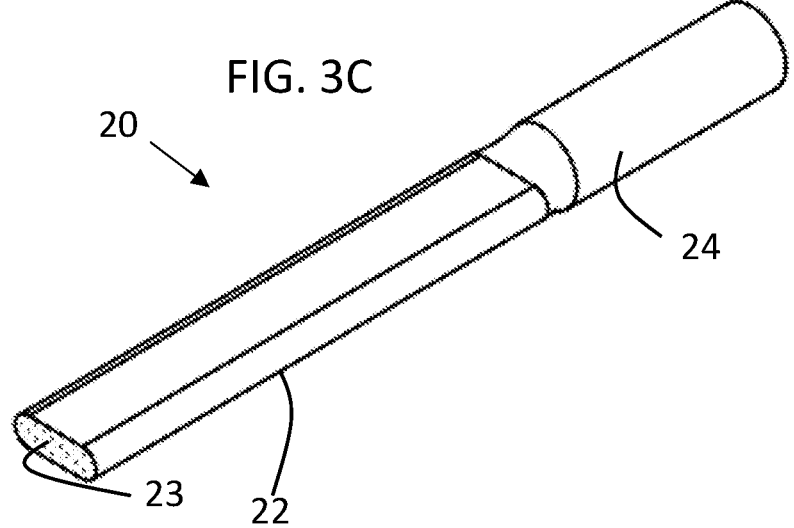

Reference is now made to FIGS. 3A, 3B, and 3C, which are schematic illustrations of respectively, a capsule having a circular cross-section, a capsule that has been flattened by having mechanical pressure applied to the capsule at discrete locations along its length, and a capsule that has been flattened along the entire length of portion 22, in accordance with some applications of the present invention. For some applications the capsule is flattened by smoking device 200. For some applications, smoking device 200 includes two or more electrodes that are configured (a) to heat a heating element that is disposed within the capsule via electrical resistive heating, and (b) to apply mechanical pressure to the capsule in order to flatten at least part of portion 22 of the capsule. For some applications, the electrodes apply mechanical pressure at discrete locations along its length (as indicated in FIG. 3B). For some applications, the electrodes apply mechanical pressure along the entire length of portion 22 (as indicated in FIG. 3C).

Figures 4A, 4B:
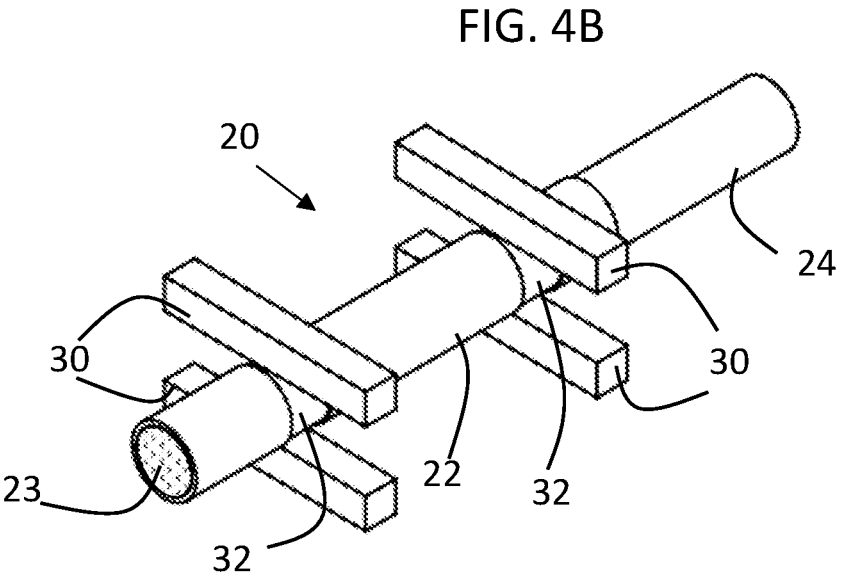
FIGS. 4A, 4B, and 4C are schematic illustrations of electrodes being placed in electrical contact with a heating element of a capsule, in accordance with some applications of the present invention.
Figures 4C, 4D:
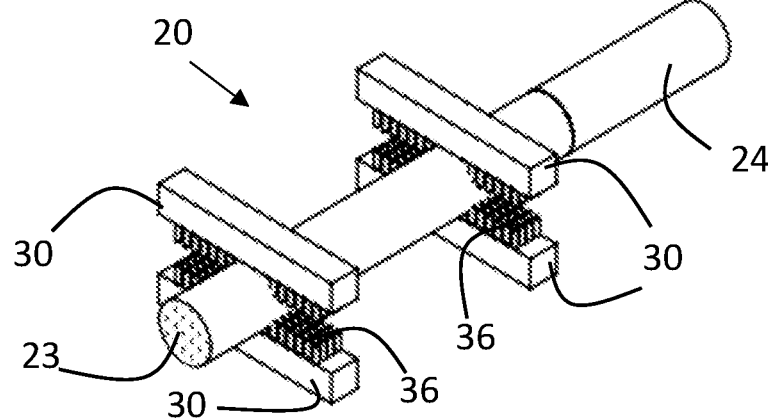
FIG. 4D is a schematic illustration of electrodes that include needle contacts that are configured to pierce a paper covering and directly contact a heating element of a capsule, in accordance with some applications of the present invention.

Reference is now made to FIGS. 4A, 4B, and 4C, which are schematic illustrations of electrodes 30 being placed in electrical contact with a heating element 32 of capsule 20, in accordance with some applications of the present invention. As described hereinabove, typically, the heating element is built-in to the capsule, such that it is in direct contact with smoking material. Also as described hereinabove, the capsule is typically configured to be disposable and for use in a single smoking session. Thus, problems associated with repeated use of heating elements, such as a build-up of dirt and/or impurities, as well as wear-and-tear due to repeated heating and/or mechanical interactions, are avoided. For some applications, the heating element comprises a metallic material, which is typically disposed within the capsule and/or is typically in direct contact with the smoking material, and that is heated via electrical resistive heating. For some applications, the heating element is a metallic foil (e.g., stainless steel foil, nickel-titanium foil, titanium foil, copper foil, aluminum foil, steel foil) that typically is in direct contact with, and surrounds, the smoking material within portion 22 of capsule 20. For some applications, the foil has a thickness of more than 1 micron (e.g., more than 3 microns) and/or less than 20 microns (e.g., less than 10 microns), for example, 1-20 microns, or 3-10 microns. Typically, a current is applied along the length of portion 22 (e.g. with a positive electrode at the first end and a negative electrode at the second end, or vice versa) and airflow is parallel to the direction of the current flow. For some applications, a current is applied along the metallic foil along a length of portion 22 that is greater than 5 mm, e.g., greater than 15 mm. Typically, the metallic foil is flexible such that it is configured to be flattened by mechanical flattening elements, as described in further detail hereinbelow.

As described hereinabove, it is typically desirable for capsule 20 to have the general structure of a traditional cigarette. Typically, the heating element extends along the entire length of the smoking-material-containing portion of the capsule. For some applications, the heating element only extends along a portion of the length and/or the circumference of the smoking-material-containing portion of the capsule, as described in further detail hereinbelow. For some applications, the capsule includes a paper covering 34, and the heating element 32 (which is typically as described hereinabove) is printed and/or is adhered to the paper covering. Typically, at the locations at which the electrodes contact the capsule, the heating element is exposed to the electrodes, such as to make direct electrical contact with the electrodes. For example, as shown in FIGS. 4A and 4B, at the locations at which the electrodes contact the capsule, the heating element is not covered with paper covering 34. As shown in FIG. 4C and as described hereinabove, for some applications, the electrodes apply mechanical pressure to portion 22 of the capsule, such as to flatten at least part of portion 22 of the capsule.

Referring to FIG. 4D, for some applications, the electrodes include needle contacts 36 that are configured to pierce the paper covering and directly contact the heating element.

For some applications, an electrically-conducting material is absorbed into the paper covering in order to facilitate electrical contact between the electrodes and the heating element. Alternatively or additionally, an electrically-conducting material passes through the paper from the heating element to contacts that directly contact the electrodes.

For some applications, the capsule includes a thermally-insulating material layer within at least a portion of the capsule, in order to reduce heat loss via the walls of the capsule.

Figure 5:
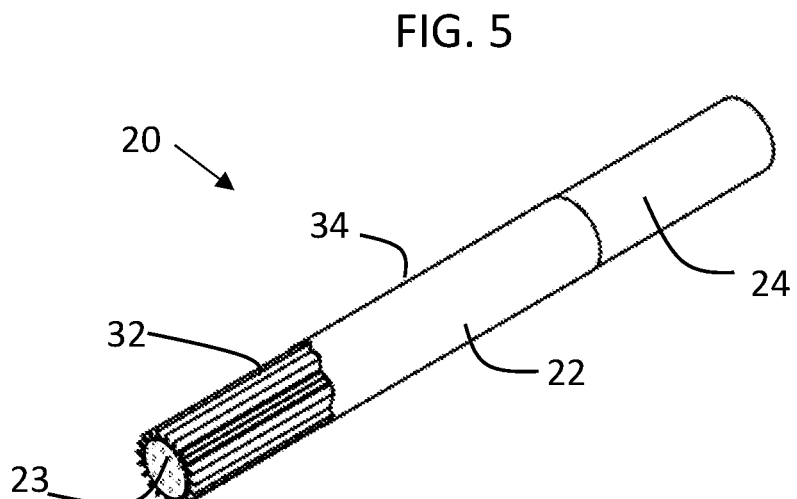
FIG. 5 is a schematic illustration of a heating element that includes folds, in accordance with some applications of the present invention.

Reference is now made to FIG. 5, which is a schematic illustration of a heating element that includes folds (e.g., zigzagging or undulating folds). Typically, by including folds, the area of contact between the heating element and the smoking material is increased relative to if it did not include folds. For some applications, by including folds, the heating element is shaped to define ribs that penetrate into the smoking material, thereby (a) increasing the arca of contact between the heating element and the smoking material, and/or (b) decreasing the maximum distance between the heating element and the smoking material. For some applications, a folded heating element as shown in FIG. 5 is combined with one or more of the techniques described with reference to FIGS. 4A-D.

Figures 6A, 6B:
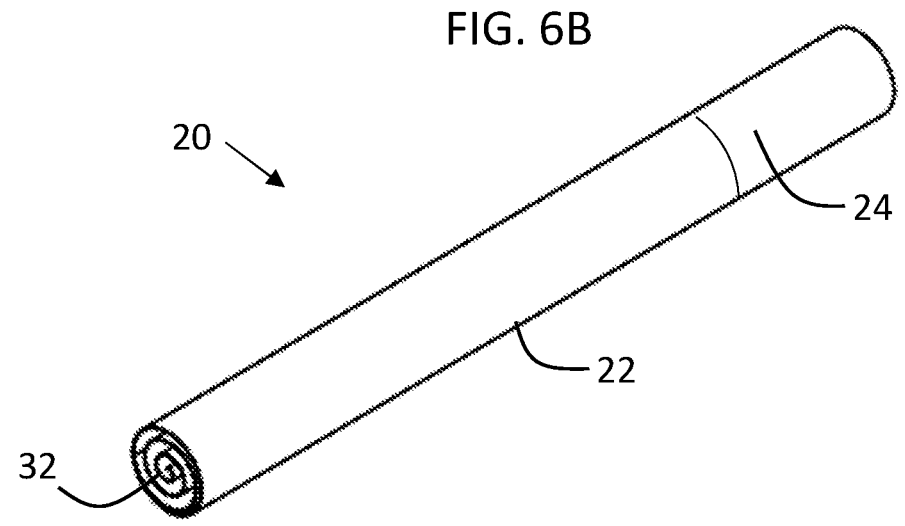
FIGS. 6A and 6B are schematic illustrations of a capsule that includes a heating element that penetrates into smoking material, in accordance with some applications of the present invention.

Reference is now made to FIGS. 6A and 6B, which are schematic illustrations of capsule 20, the capsule including a heating element 32 that penetrates into the smoking material. As described hereinabove, for some applications, the heating element is a metal foil (e.g., stainless steel foil, nickel-titanium foil, titanium foil, copper foil, aluminum foil, steel foil) that typically is in direct contact with, and surrounds, the smoking material within portion 22 of capsule 20. For some applications, the foil has a thickness of more than 1 micron (e.g., more than 3 microns) and/or less than 20 microns (e.g., less than 10 microns), for example, 1-20 microns, or 3-10 microns. Typically, a current is applied along the length of portion 22 (e.g. with a positive electrode at the first end and a negative electrode at the second end, or vice versa) and airflow is parallel to the direction of the current flow. For some applications, a current is applied along the metallic foil along a length of portion 22 in an axial direction along the metallic foil (i.e., along a direction that is parallel to the longitudinal axis of the capsule) that is greater than 5 mm, e.g., greater than 15 mm. For some applications, the foil is shaped and disposed within the capsule such that a flap 40 of the heating element penetrates into the smoking material, as shown in FIG. 6A. For some applications, the foil has a spiral shape that spiral through the smoking material, as shown in FIG. 6B. For some applications, by penetrating into the smoking material, the heating element (a) increases the area of contact between the heating element and the smoking material, and/or (b) decreases the maximum distance between the heating element and the smoking material.

Figures 7A, 7B, 7C, 7D:
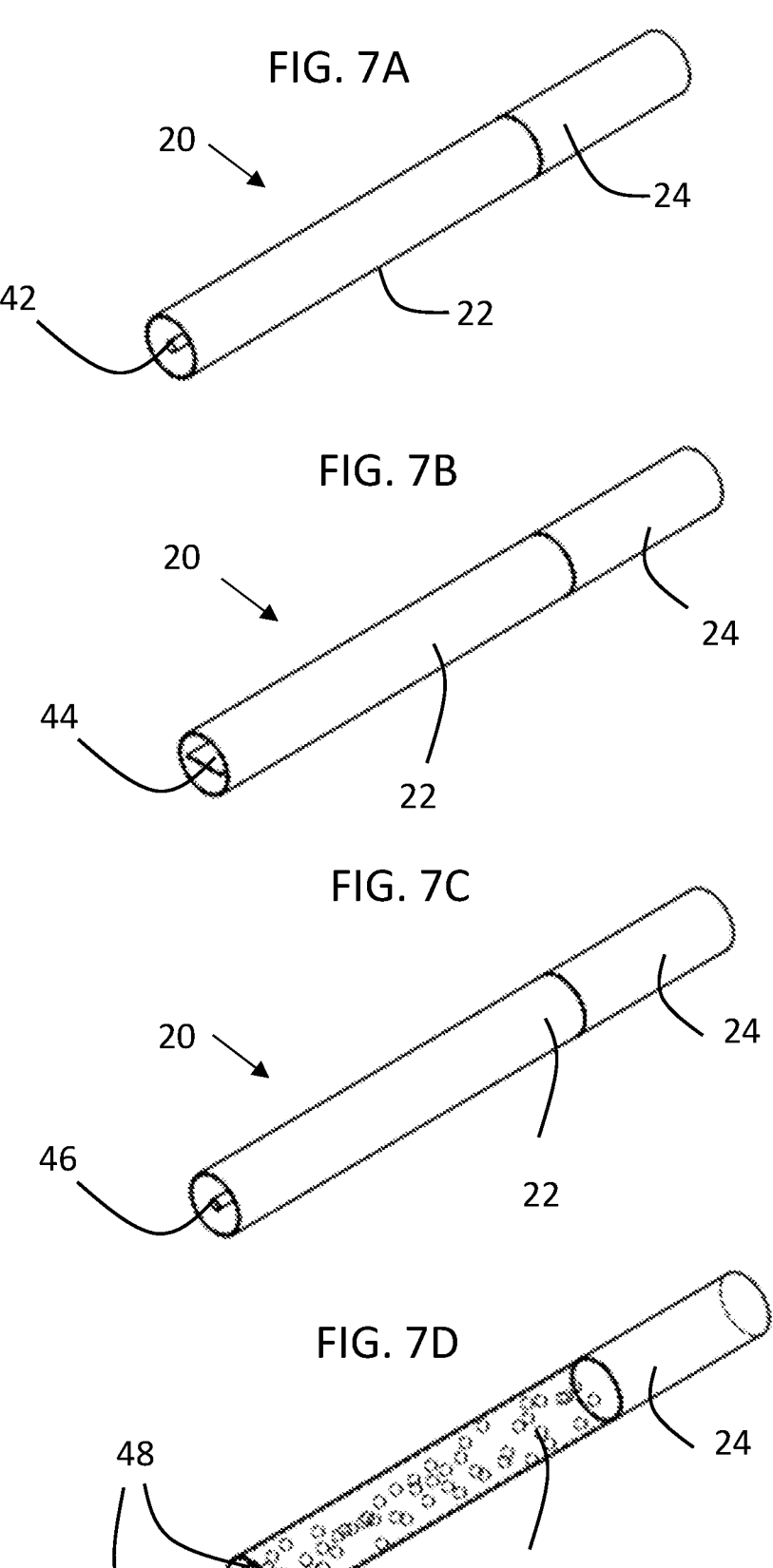
FIGS. 7A, 7B, 7C and 7D are schematic illustrations of a capsule that includes one or more magnetic heating elements, in accordance with some applications of the present invention.

Reference is now made to FIGS. 7A, 7B, 7C and 7D, which are schematic illustrations of capsule 20, the capsule including one or more magnetic heating elements, in accordance with some applications of the present invention. As described hereinabove, typically, the heating element is built-in to the capsule, such that it is in direct contact with smoking material. For some applications, at least some of the heating element is embedded within the smoking material. For some applications, the heating element comprises one or more magnetically-heated materials (i.e., materials that are susceptible to being heated by a magnetic field (such as, magnetic materials and/or ferromagnetic materials)), which are typically disposed within the capsule and/or are typically in direct contact with smoking material, and that are heated via magnetic induction. For some applications smoking device 200 includes a coil that is configured to generate an electromagnetic field, as described in further detail hereinbelow. The coil is configured to heat the magnetically-heated material within the capsule via magnetic induction. In accordance with some applications, the magnetically-heated material is configured as a magnetically-heated rod 42 that is disposed along the length of a portion of the capsule (as shown in FIG. 7A), a magnetically-heated strip 44 that is disposed along the length of a portion of the capsule (as shown in FIG. 7B), a magnetically-heated tube 46 that is disposed along a portion of the length of the capsule (shown in FIG. 7C), and/or a plurality of magnetically-heated particles 48 (e.g., balls or beads) that are dispersed within the smoking material (as shown in FIG. 7D). Alternatively or additionally, a magnetically-heated material is disposed around the smoking material (e.g., underneath a paper covering), in a similar manner to that described with reference to the metallic foil that is heated via electrical resistive heating. For some applications, there is no magnetically-heated material disposed around the smoking material. Typically for applications in which the capsule includes one or more magnetically-heated materials, the smoking material is covered with a covering material that does not attenuate with an electromagnetic field that is generated by the smoking device (e.g., by a coil of the smoking device). For some such applications, the smoking material is covered with a paper covering as described in further detail hereinbelow. For some applications, the smoking material is covered with a cover which is itself a magnetically-heated material (e.g., a metallic foil). Typically, at least part of portion 22 is configured to be flattened by the smoking device (or to be provided to the user in a flattened shape). Typically, the material with which the smoking material is covered is flexible, such as to allow portion 22 to be flattened.

Figure 8A:
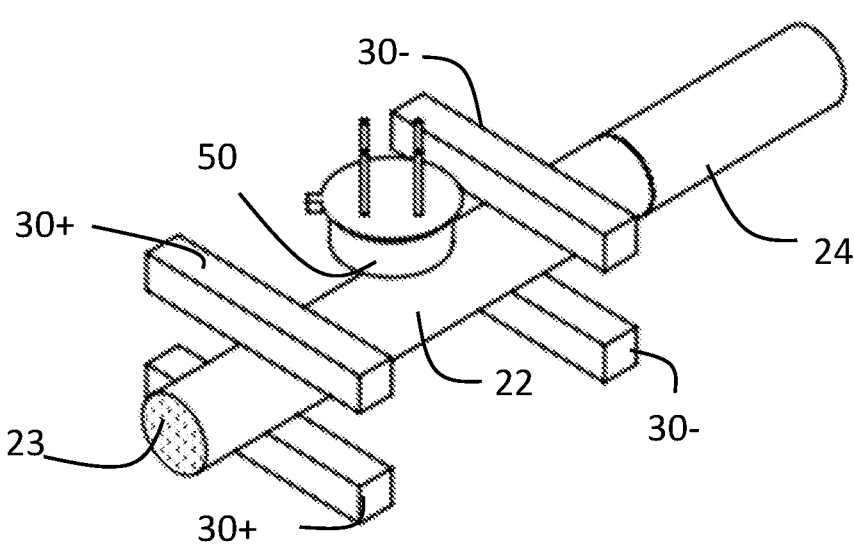
FIGS. 8A and 8B are schematic illustrations of one or more sensors for sensing the temperature of the smoking material within a capsule, in accordance with some applications of the present invention.
Figure 8B:
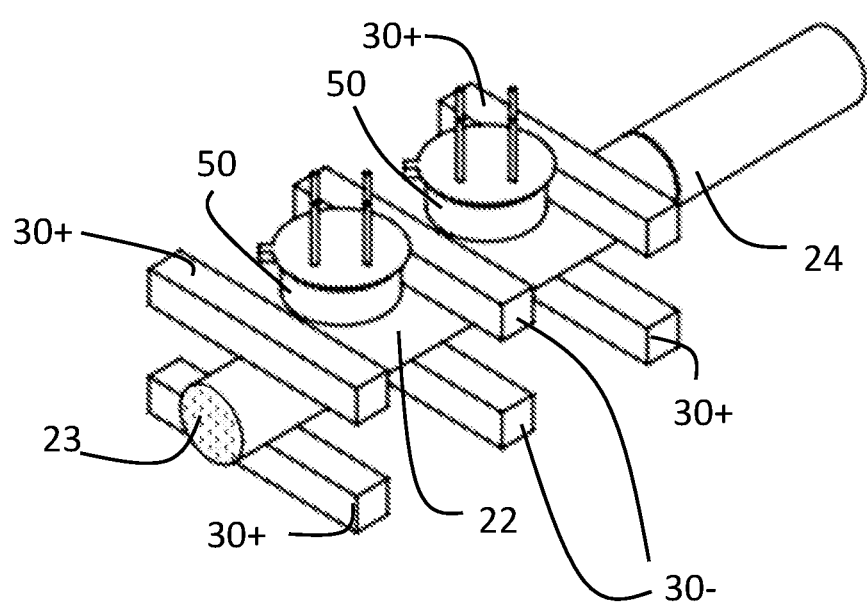

Reference is now made to FIGS. 8A and 8B, which are schematic illustrations of one or more sensors 50 for sensing the temperature of the smoking material within a capsule, in accordance with some applications of the present invention. FIGS. 8A and 8B show the sensors being used to sense the temperature of smoking material of a capsule that is being heated via electrical resistive heating of a heating element by electrodes 30. However, the sensors are typically also used with a capsule that is heated via magnetic induction, mutatis mutandis.

As described hereinabove, typically in order to heat smoking material via electrical resistive heating, a current is applied along the length of portion 22 of the capsule (e.g. with a positive electrode at the first end and a negative electrode at the second end, or vice versa) and airflow is parallel to the direction of the current flow. For some applications, the current is applied along the entire length of the heating element using a single pair of electrodes (or a respective single pair of electrodes along each side of the capsule), as shown in FIG. 8A. Alternatively, respective electrode pairs apply current along respective portions of the length of the heating element, as shown in FIG. 8B. (In FIGS. 8A and 8B, the electrodes are denoted to be positive and negative using reference numerals 30+ and 30– respectively, by way of example. The charges of the electrodes could be reversed.) For some applications, a current is applied along the metallic foil along a length of portion 22 in an axial direction along the metallic foil (i.e., along a direction that is parallel to the longitudinal axis of the capsule) that is greater than 5 mm, e.g., greater than 15 mm.

For some applications, control of each portion of the heating element may thereby be controlled separately. For some such applications, respective portions along the length of the heating element are heated to respective, different temperatures. For some such applications, respective materials are vaporized by the respective portions of the heating element. For example, one portion may contain smoking material, while another portion may include materials that provide flavor to the vapor. For some applications, the user selects a type of vapor according to their preferences and the respective portions along the length of the heating element are heated accordingly (e.g., according to different temperature profiles). Typically, for applications in which respective electrode pairs apply current along respective portions along the length of the heating element (as shown in FIG. 8B), a respective temperature sensor is configured to detect the temperature of portions of the smoking material that are disposed within respective portions along the length of the heating element.

Figure 8C:
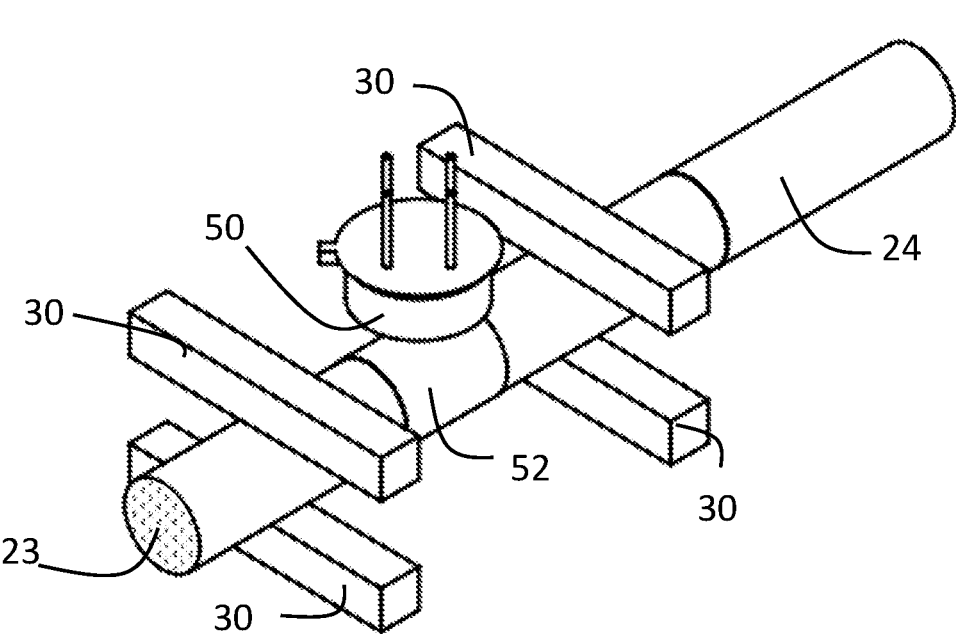
FIG. 8C is a schematic illustration of a capsule that includes a portion that is disposed in the vicinity of a temperature sensor, the portion being covered, coated, and/or treated such as to be non-reflective or to have a high emissivity value, in accordance with some applications of the present invention.

Reference is now made to FIG. 8C, which is a schematic illustration of a capsule that includes a portion 52 that is disposed in the vicinity of temperature sensor 50, portion 52 being covered, coated, and/or treated such as to be non-reflective or to have a high emissivity value (e.g., emissivity of at least 0.5, or at least 0.95), in accordance with some applications of the present invention. Typically, sensor 50 is configured to sense the temperature of the smoking material without extracting any heat from the smoking material. For some applications, sensor 50 is a contact sensor that contacts the smoking material in order to measure the temperature of the smoking material. For some applications, the temperature sensor is a thermal camera and/or a thermocouple sensor that senses the overall resistance of the capsule (or a portion thereof) and thereby derives the temperature of the capsule. For some applications, the sensor is an infrared temperature sensor that is configured to detect the temperature of the smoking material by detecting infrared thermal radiation from the smoking material (and typically without contacting the smoking material). As described hereinabove, typically capsule includes a heating element that is metallic and that surrounds the smoking material. Typically, the heating element comprises a reflective material. For some applications, in order to facilitate an accurate determination of the temperature of the smoking material using the infrared temperature sensor, the capsule is configured to be non-reflective, or to have a high emissivity value, at the location at which the sensor detects the temperature of the capsule. For example, the capsule is covered or coated with a non-reflective material, or with a material having a high emissivity value (e.g., emissivity of at least 0.5, or at least 0.95), at that location (e.g., polyimide tape, paper, or another thin material with high thermal conductivity and high emissivity). For some applications, the capsule is treated (e.g., via chemical treatment, sand-blasting, etching, coloring, knurling, and/or oxidation), such that the capsule is configured to be non-reflective, or to have a high emissivity value (e.g., emissivity of at least 0.5, or at least 0.95), at the location at which the sensor detects the temperature of the capsule.

Figure 8D:
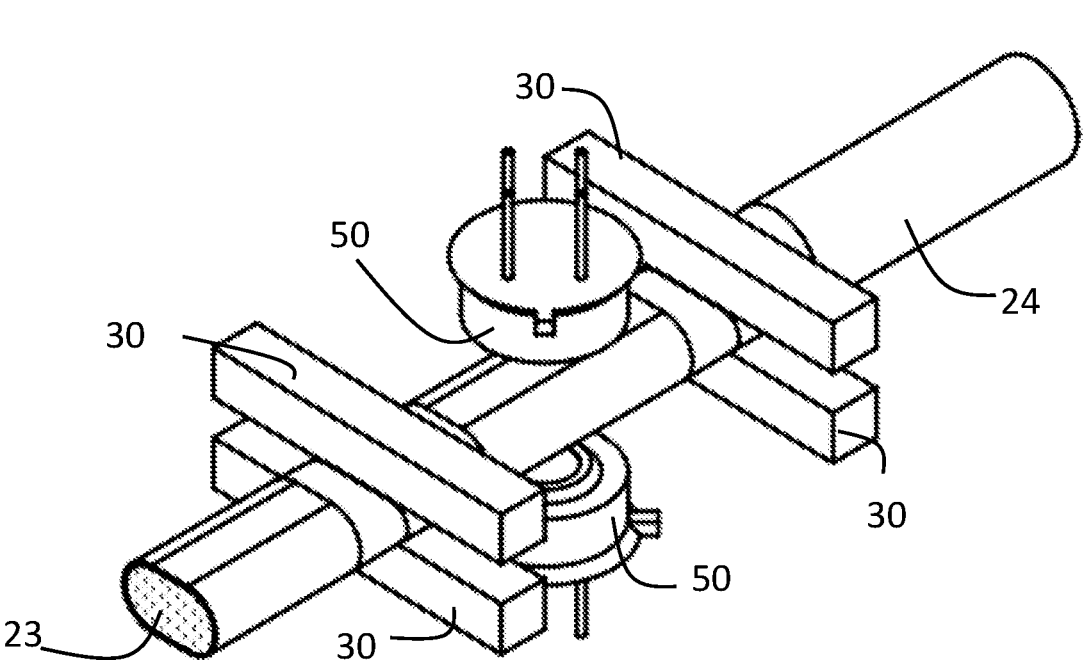
FIG. 8D is a schematic illustration of two or more sensors being used to detect the temperature of the smoking material within capsule at the same location along the length of the capsule as each other, in accordance with some applications of the present invention.

Reference is now made to FIG. 8D, which is a schematic illustration of two or more sensors 50 being used to detect temperature of the smoking material within capsule 20 at the same location along the length of the capsule as each other, in accordance with some applications of the present invention. For some applications, the sensors are placed on respective sides of the capsule. For some such applications, an average temperature of the smoking material is deter-mined based upon the temperatures detected by each of the sensors. For some applications, a temperature range across the smoking material is determined, a maximum temperature of the smoking material is determined, and/or a minimum temperature of the smoking material is determined, based on the temperatures detected by each of the sensors. For some applications, the temperature of the smoking material is detected using the temperature that is detected by only one of the sensors, for example, if the temperature detected by the other sensor (or another indication from the other sensor) indicates that the other sensor is faulty, is dirty, has come into contact with the capsule, is detecting the temperature from a region of overlap of the cover of the capsule, etc.

For some applications, the temperature detected by the sensors described with reference to any one of FIGS. 8A-D is used as feedback in response to which heating of the heating element is controlled. Typically, the heating of the heating element is controlled such as to maintain the smoking material within a predefined temperature range, at which the active agents within the smoking material are vaporized but the smoking material isn't pyrolyzed. For some applications, a control component 233 (e.g., a control chip and/or a control microprocessor, shown in FIGS. 29C and 29D) within the smoking device is configured to detect that a user has puffed the smoking device (and/or a parameter of the puff, such as length of puff and/or depth of puff) based on the temperature of the smoking material that is detected by the sensor. Typically, the sensor detects the amount of current that must be applied to the heating element in order to maintain the smoking material at a constant (or substantially constant) temperature and thereby detects that the user has puffed the smoking device (and/or determines a parameter of the puff, such as length of puff and/or depth of puff).

For some applications, upon insertion of a capsule into the smoking device (or in response to being activated in a different manner, e.g. by the push of a button), the smoking device preheats the capsule to below the vaporization temperature of the smoking material, as described in further detail hereinbelow with reference to FIG. 34. Subsequently, in response to detecting that the user has puffed from the smoking device (or in response to being activated in a different manner, e.g. by the push of a button), the control component heats the smoking material to its vaporization temperature. For some applications, during the use of a given capsule, the control component detects the number of puffs, the lengths of the puffs, and/or the depths of the puffs that the user has taken from the capsule. For some such applications, the control component prevents the capsule from being heated, in response to detecting an indication that more than a given amount of the active agent has been vaporized. In this manner, the smoking device is configured to provide a metered dose of an active agent to the user. Alternatively or additionally, in this manner, the smoking device is configured to prevent further use of a capsule once the further use is likely to cause unwanted flavors, pyrolysis of the smoking material, etc. For some applications, the smoking device is configured to receive an input indicating the type of capsule that is placed in the device (and/or is configured to detect this automatically, as described in further detail hereinbelow), and is configured to control the heating of the smoking material in the above-described manner in response thereto.

Figure 9A:
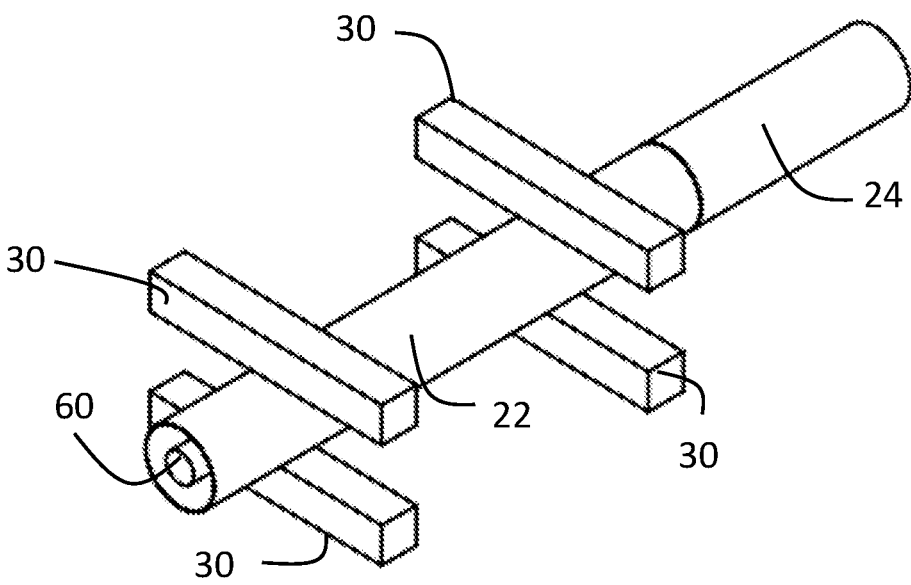
FIGS. 9A, 9B, and 9C are schematic illustrations of a capsule including a collapse-prevention element, in accordance with some applications of the present invention.
Figure 9B:
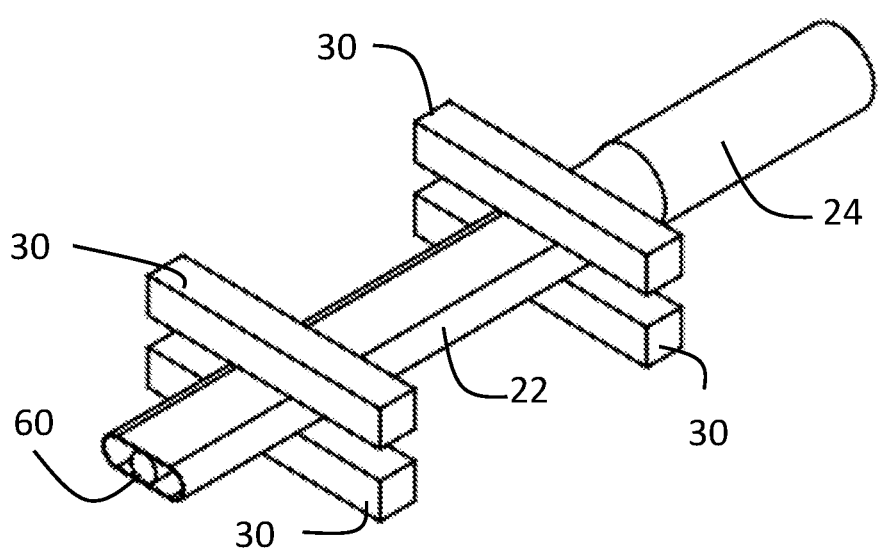
Figure 9C:
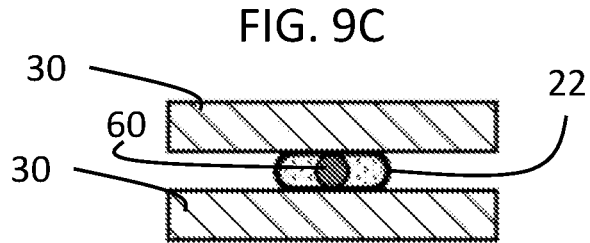

Reference is now made to FIGS. 9A, 9B, and 9C, which are schematic illustrations of capsule 20, the capsule including a collapse-prevention element 60, in accordance with some applications of the present invention. As shown in FIGS. 9A-C, the collapse-prevention element is shaped as a rod that extends axially along the longitudinal axis of portion 22 of the capsule. For some applications, the rod has a diameter of more than 0.5 (e.g., less than 2 mm) and/or less than 5 mm (e.g., less than 3 mm), e.g., 0.5-5 mm, or 2-3 mm. The collapse-prevention element is configured to prevent portion 22 of the capsule from collapsing when mechanical pressure is applied to portion 22 in order to flatten portion 22 of the capsule. It is noted that, in the absence of a collapse-prevention element, portion 22 of the capsule is susceptible to collapsing or becoming crushed, since the smoking material the heating element and the paper covering are typically all soft, non-rigid materials. By contrast, the rod is typically rigid and holds portion 22 of the capsule open at least to the diameter of the rod. Typically, the diameter of the rod defines the thickness of portion 22 when the capsule is in its flattened configuration. By defining the thickness of the portion 22 when the capsule is in its flattened configuration, the rod ensures that there is adequate airflow through portion 22. In addition, the rod ensures that there is good electrical contact between the electrodes and the heating element, by ensuring that the heating element is held in contact with the electrodes.

FIG. 9A shows the capsule before mechanical pressure has been applied to portion 22 by electrodes 30, and FIGS. 9B-C show the capsule after mechanical pressure has been applied to portion 22. As shown in FIGS. 9B-C, the rod holds open portion 22, such that the thickness of portion 22 when the capsule is in its flattened configuration is defined by the diameter of the rod.

It is noted that, for some applications, the rod does not extend along the entire length of portion 22 of the capsule. For example, the rod may only be disposed along a portion of the length of portion 22 within which the heating element is configured to contact the electrodes. For some applications, two or more rods are disposed within respective regions at which the heating element is configured to contact the electrodes, along the length of portion 22 of the capsule, as shown in FIG. 10A.

For some applications, the rod is a solid rod. As described above, typically the rod is rigid. For some applications, the rod is flexible, but it has a greater rigidity than the smoking material. Typically, the rod is made of a material that can withstand being heated to the temperatures to which the smoking material is heated. In accordance with respective applications, the rod is made of wood, metal, and/or a polymeric material, such as polyether ether ketone (PEEK). For some applications, the rod is made of a natural or smoking material, such as wood, tobacco, and/or hemp. For some applications, the rod is configured to diffuse one or more chemicals, such as flavoring, pharmaceuticals, and/or a vapor-generating chemical, such as glycerol. For some applications, the rod includes a phase-change material that is configured to prevent the temperature of the smoking material from exceeding the phase-change temperature of the phase-change material. Typically, the phase-change material is selected such as to prevent the temperature of the smoking material from exceeding a temperature at which the smoking material pyrolyzes. For some applications, the phase-change material is selected such as to maintain the temperature of the smoking material within an optimal range for vaporization and/or taste. For some applications the rod is configured to absorb chemicals that are generated by pyrolysis of the smoking material and/or other material within the capsule, such as nitric oxide and/or carbon monoxide. As noted above, the collapse-prevention element is not necessarily a rod, and the scope of the present disclosure includes collapse-prevention elements having different structure as would be apparent to a person of ordinary skill in the art, and as described hereinbelow. Typically, the configurations of the rod that are described above are applicable to any type of collapse-prevention element, mutatis mutandis.

Figure 10A:
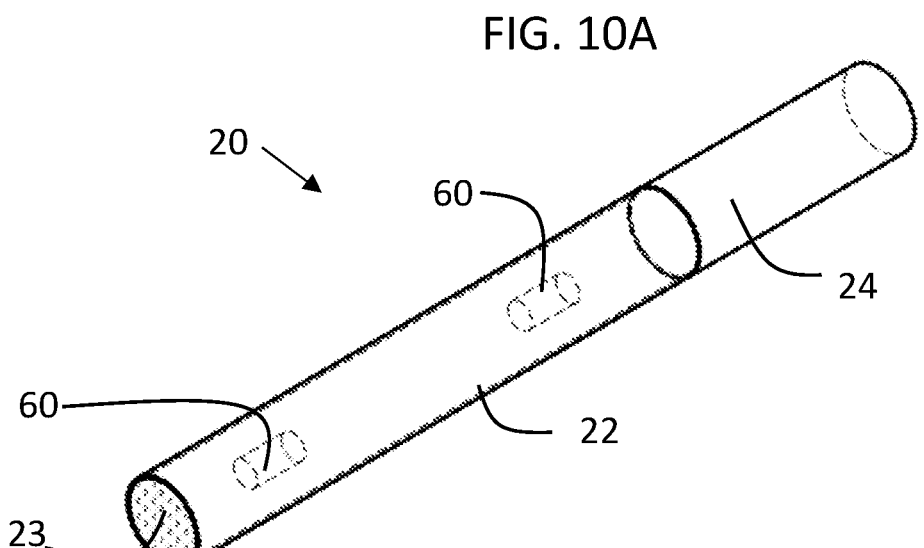
FIGS. 10A and 10B are schematic illustrations of a capsule including a collapse-prevention element, in accordance with some alternative applications of the present invention.
Figure 10B:
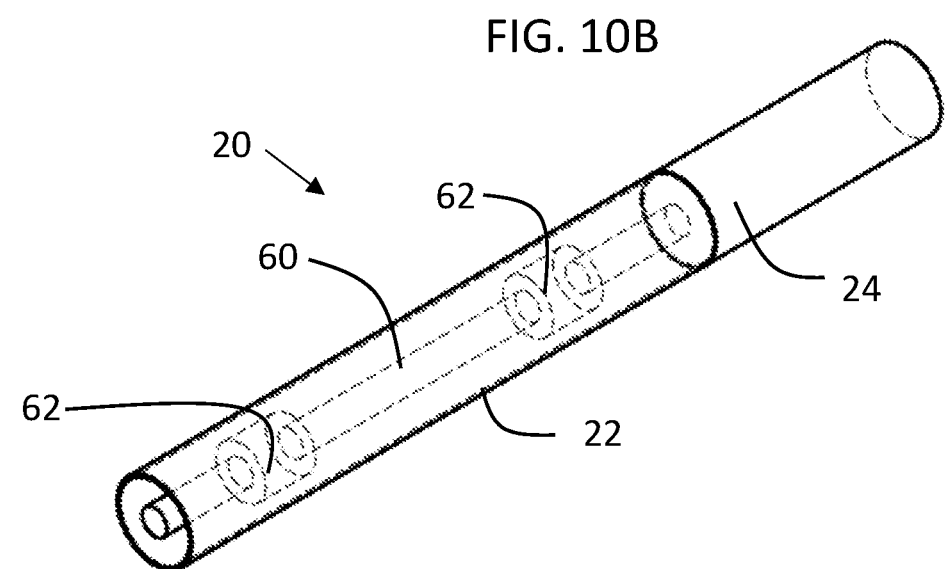

Reference is now made to FIGS. 10A and 10B, which are schematic illustrations of capsule 20, the capsule including a collapse-prevention element 60, in accordance with some applications of the present invention. With reference to FIG. 10A, and as described hereinabove, for some applications, the collapse-prevention element includes two or more rods are disposed within respective regions at which the heating element is configured to contact the electrodes, along the length of portion 22 of the capsule. With reference to FIG. 10B, for some applications, the rod has a non-uniform diameter. For example, as shown, at the location at which the electrodes are configured to come into contact with the capsule, the rod includes radially-protruding portions 62 having a greater diameter (typically, in order to ensure good electrical contact between the heating element and the electrodes), whereas at other locations, the rod has a smaller diameter.

Figure 11A:
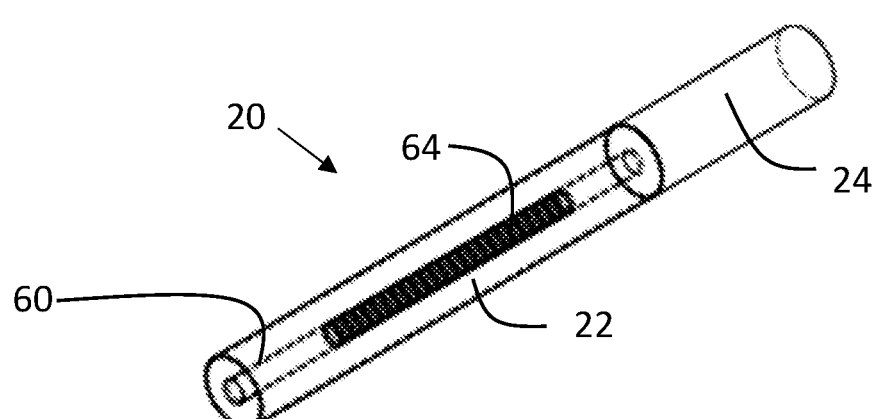
FIGS. 11A and 11B are schematic illustrations of a capsule including a collapse-prevention element, in accordance with some additional applications of the present invention.
Figure 11B:
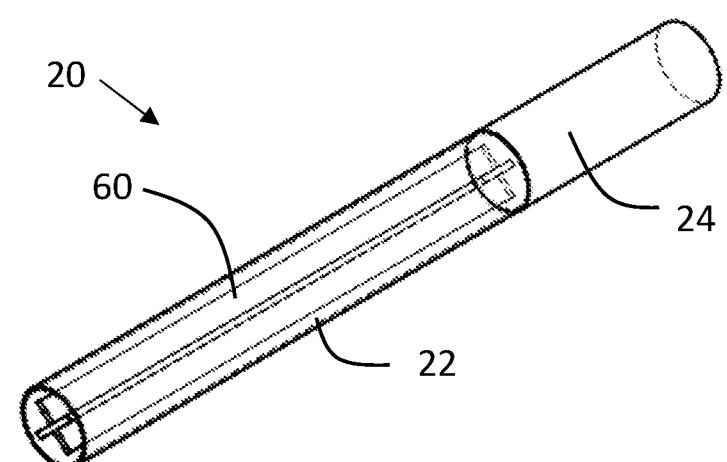
Figure 12:
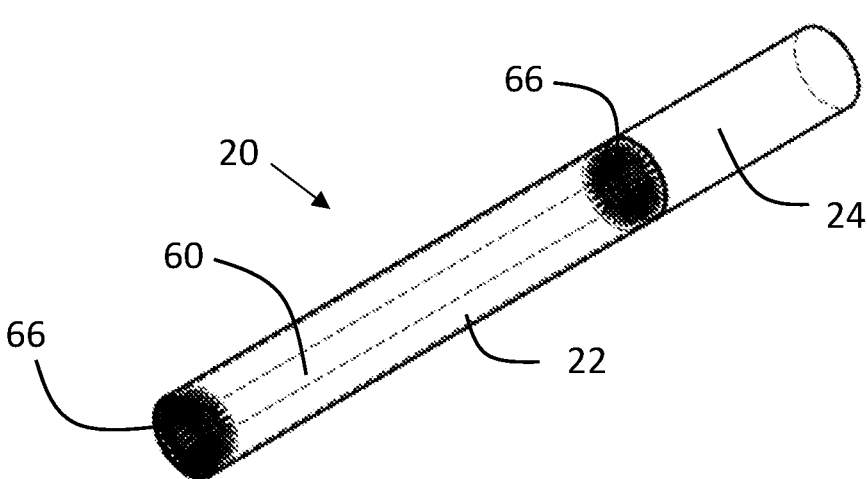
FIG. 12 is a schematic illustration of a capsule including a collapse-prevention element, in accordance with some additional applications of the present invention.

Reference is now made to FIGS. 11A and 11B, which are schematic illustrations of capsule 20, the capsule including a collapse-prevention element 60, in accordance with some applications of the present invention. For some applications, collapse-prevention element is a tube that contains chemicals (such as flavoring, pharmaceuticals, and/or a vapor-generating chemical (such as glycerol) in liquid, solid, gaseous, and/or gel form) that are released from the tube during heating of the smoking material. For example, the tube may be fenestrated (as shown in FIG. 11A), or it may include a membrane or slits, via which the chemicals are released. For some applications, the collapse-prevention element 60 is a tube that serves one or more additional functions. For example, along at least a portion of its length it may be hollow and it may define openings (such as holes or slits) that are configured to collect the vaporized active agents and direct them toward the mouthpiece. As shown in FIG. 11B, for some applications, the collapse-prevention element has a cross-shaped cross-sectional shape, such that (a) the collapse-prevention element holds open portion 22 of the capsule to a great enough thickness, but (b) the collapse-prevention element does not occupy as much of the volume of portion 22 as it would if it were to have a different shape, thereby leaving a greater volume within portion 22 to be occupied by the smoking material. Reference is now made to FIG. 12, which is a schematic illustration of capsule 20, the capsule including a collapse-prevention element 60, in accordance with some applications of the present invention. For some applications, disc-shaped or cylindrical structures 66 are disposed at one or both of the ends of the collapse-prevention element, as shown in FIG. 12. For some applications, structures 66 are configured to center the collapse-prevention element within portion 22 of the capsule. For some applications, structures 66 are configured to perform additional functions, such as to hold the collapse-prevention element in place, to prevent the smoking material from falling out of the capsule, and/or to hold the smoking material in place while allowing sufficient airflow through the capsule.

Figure 13:
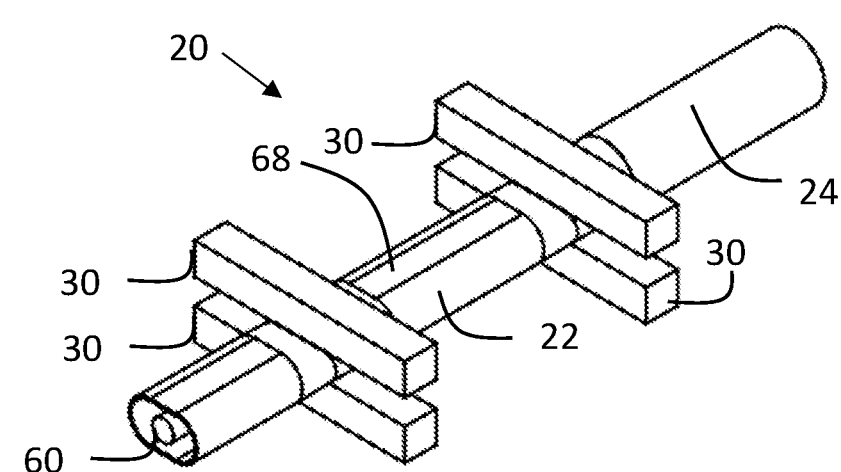
FIG. 13 is a schematic illustration of a capsule including a collapse-prevention element, in accordance with some further applications of the present invention.

Reference is now made to FIG. 13, which is a schematic illustration of capsule 20, the capsule including a collapse-prevention element 60, in accordance with some applications of the present invention. For some applications, the collapse-prevention element is configured to act as a heating element that is configured to be heated by the electrodes via electrical resistive heating. For example, when the electrodes flatten portion 22 of the capsule, the electrodes may be configured to become electrically connected to a conductive portion of the collapse-prevention element. For example, the mechanical pressure of the electrodes may be configured to bring an electrical contact 68 of portion 22 of the capsule (which is described hereinabove) into contact with a metallic coating that is disposed on the collapse-prevention element.

Figure 14:
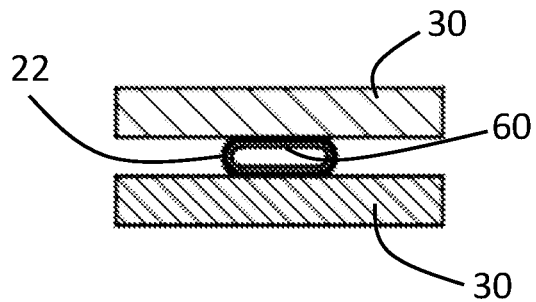
FIG. 14 is a schematic illustration of a capsule including a collapse-prevention element, in accordance with some additional applications of the present invention.

Reference is now made to FIG. 14, which is a schematic illustration of capsule 20, the capsule including a collapse-prevention element 60, in accordance with some applications of the present invention. For some applications the collapse-prevention element is a tube, e.g., a hollow, flexible tube, as shown in FIG. 14. The smoking material is disposed inside the tube and the tube typically adds rigidity to portion 22, thereby preventing it from collapsing when mechanical pressure is applied to portion 22 in order to flatten portion 22 of the capsule. Typically, the tube thereby ensures that there is adequate airflow through portion 22 and that there is good electrical contact between the electrodes and the heating element, by ensuring that the heating element is held in contact with the electrodes.

Figure 15A:
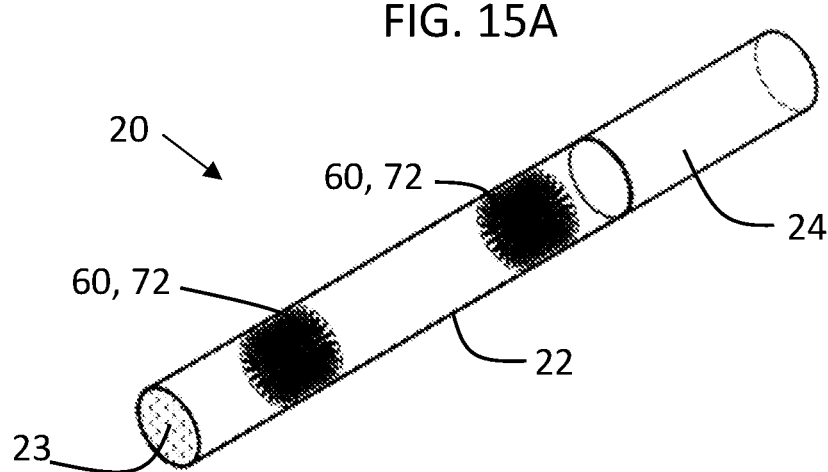
FIGS. 15A and 15B are schematic illustrations of a capsule including a collapse-prevention element, in accordance with some further applications of the present invention.
Figure 15B:
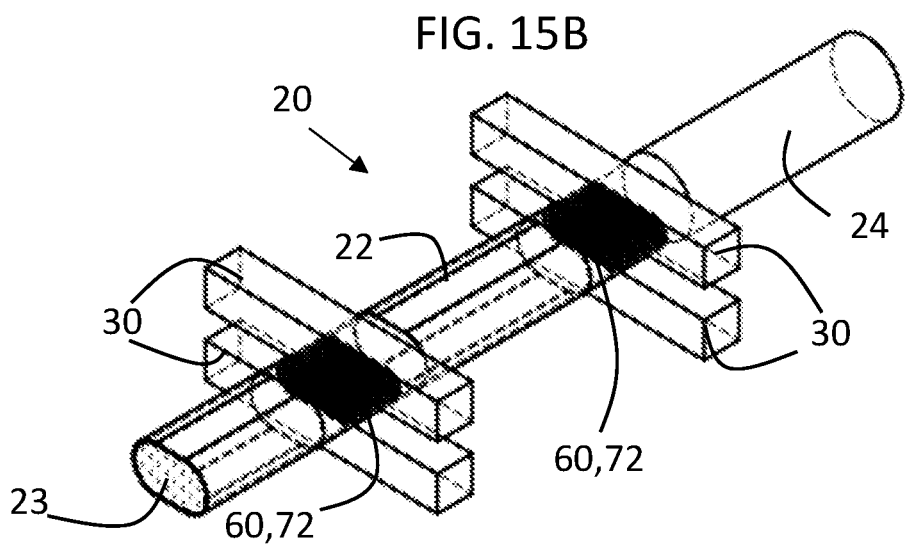

Reference is now made to FIGS. 15A and 15B, which are schematic illustrations of capsule 20, the capsule including a collapse-prevention element 60, in accordance with some applications of the present invention. FIG. 15A shows capsule 20 in a non-compressed configuration and FIG. 15B shows the capsule in a compressed configuration with mechanical pressure having been applied to the capsule by electrodes 30 (or a different mechanical flattening element), in order to flatten the capsule. For some applications, the collapse-prevention element is a spongy, or foam, disc-shaped or cylindrical element 72 that is disposed at one or both ends of portion 22 of the capsule. For some applications, the shape and/or material of element 72 is similar to that of a cigarette filter. Typically, element 72 is configured to allow airflow therethrough and is configured to maintain a given minimum thickness even when mechanical pressure is applied to element 72. Element 72 thereby ensures that there is adequate airflow through portion 22 and that there is good electrical contact between the electrodes and the heating element, by ensuring that the heating element is held in contact with the electrodes. For some applications, a cylindrical element is disposed at each end of portion 22, with a predefined quantity of smoking material disposed between the two cylindrical elements. For some applications, since there is a predefined quantity of smoking material disposed between the two cylindrical elements, the capsule is configured to provide a metered dose of an active agent to the user. For some such applications, the smoking device is configured to detect tampering with the capsule, to ensure that the dose that is being provided to the user has not been tampered with.

Figure 16A:
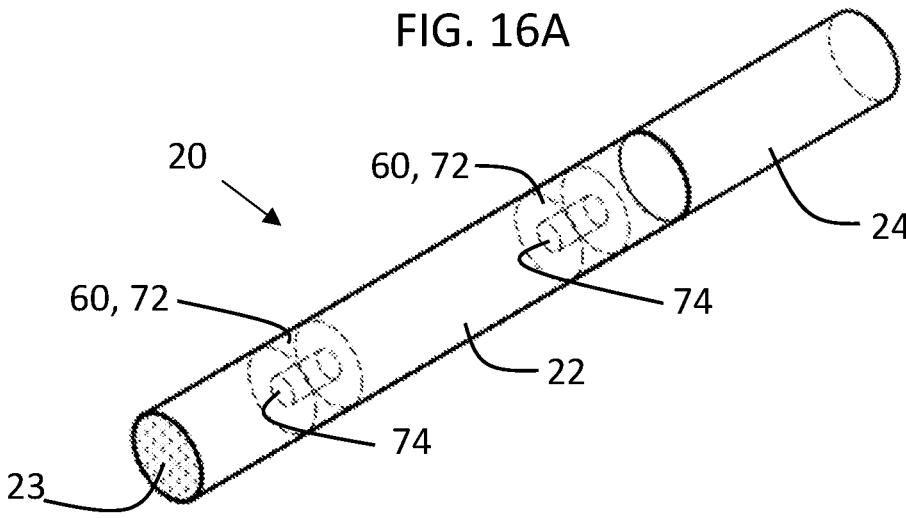
FIGS. 16A and 16B are schematic illustrations of a capsule including a collapse-prevention element, in accordance with some additional applications of the present invention.
Figure 16B:
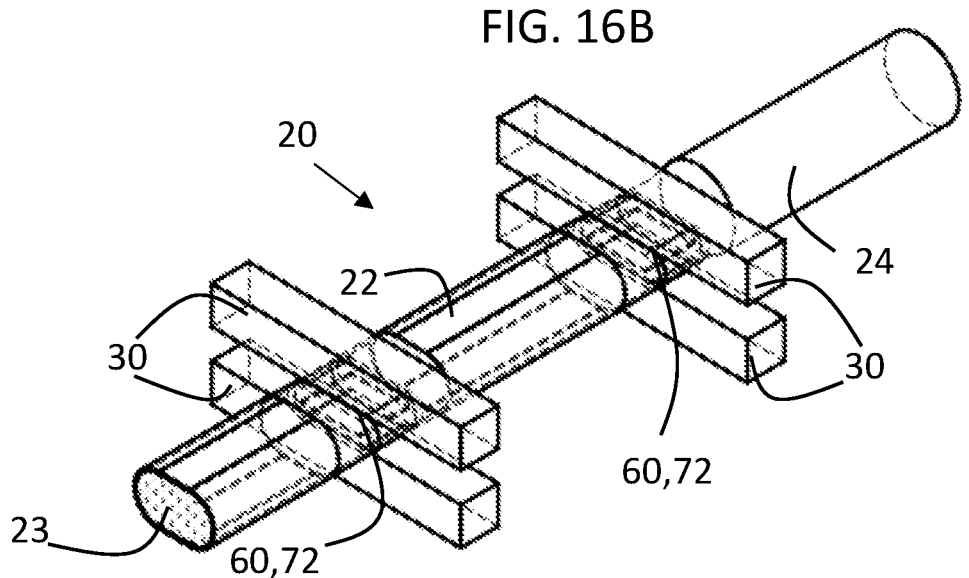

Reference is now made to FIGS. 16A and 16B, which are schematic illustrations of capsule 20, the capsule including a collapse-prevention element 60, in accordance with some applications of the present invention. As described with reference to FIGS. 15A and 15B, for some applications, the collapse-prevention element is a spongy or foam disc-shaped or cylindrical element 72 that is disposed at one or both ends of portion 22 of the capsule. For some applications, the shape and/or material of element 72 is similar to that of a cigarette filter. For some applications, element 72 defines a lumen 74 therethrough. The lumen is typically configured to allow airflow through element 72 even when element 72 has been compressed.

Figure 17:
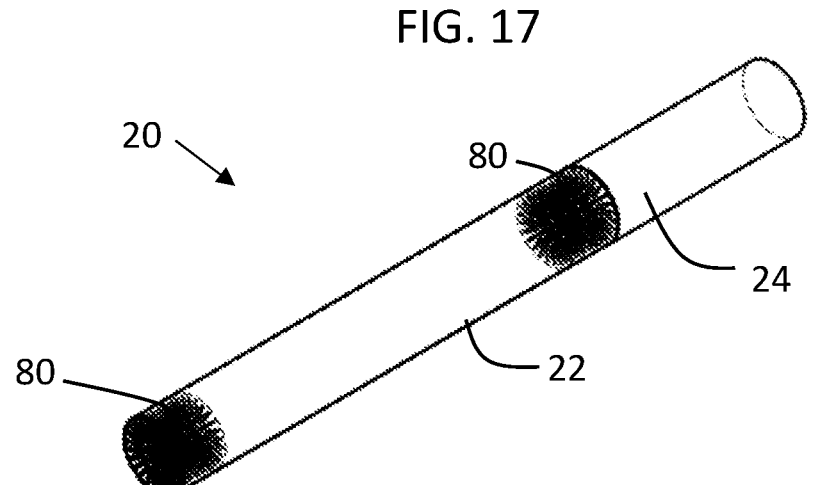
FIG. 17 is a schematic illustration of a capsule including one or more stoppers, in accordance with some applications of the present invention.

Reference is now made to FIG. 17, which is a schematic illustration of capsule 20, the capsule including one or more stoppers 80, in accordance with some applications of the present invention. For some applications, the stoppers are spongy or foam, disc-shaped or cylindrical elements that are disposed at one or both ends of portion 22 of the capsule. For some applications, the shape and/or material of each of the stoppers is similar to that of a cigarette filter. Typically, the stoppers are configured to prevent the smoking material from being dislodged from within the capsule (which can result in the smoking material itself entering the user's mouth and/or can lower the efficiency of the device). The stoppers are typically configured to allow airflow through the capsule while preventing the smoking material from becoming dislodged. For some applications, the stoppers include holes that are configured to allow airflow through the stoppers. For some applications, at least one of the stoppers is configured to adjust the airflow resistance of the capsule. for example, to make it similar to the airflow resistance of a traditional combustion cigarette.

Reference is now made to FIGS. 18A, 18B, and 18C, which are schematic illustrations of capsule 20 including a mouthpiece 90, in accordance with some applications of the present invention. As described hereinabove, typically portion 24 of the capsule defines mouthpiece 90. Typically, the user sucks the vapors from the capsule via the mouthpiece. Typically, the mouthpiece is configured to prevent at least some of the heat from the heated portion of the capsule from reaching the user's mouth. For some applications, the mouthpiece includes flavoring agents. For some applications, the mouthpiece filters the vapors. For some applications, the mouthpiece cools the vapors. With reference to FIG. 18A, for some applications, the mouthpiece includes a spongy or foam disc-shaped or cylindrical element 92 that is typically similar to that of a cigarette filter, and which is covered with paper 94. With reference to FIG. 18B, for some applications, the mouthpiece comprises a tube 96 that has spokes 98 (e.g., plastic spoke or metal spokes) that are configured to cool the vapors. With reference to FIG. 18C, for some applications, the mouthpiece comprises a hollow tube 100 that defines a lumen 102 that is configured to allow airflow therethrough.

Figure 19A:
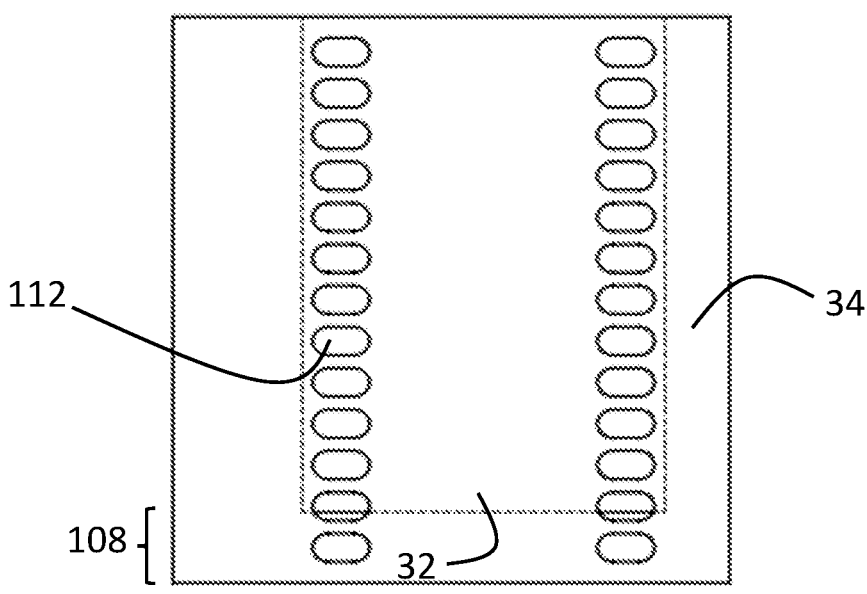
FIGS. 19A and 19B are schematic illustrations of a paper covering and heating element of a capsule, in accordance with some applications of the present invention.
Figure 19B:
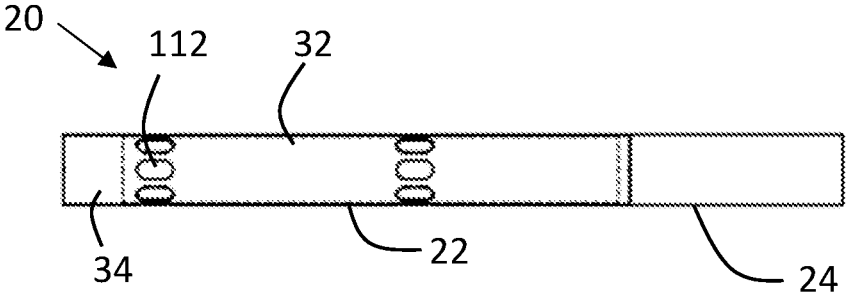

Reference is now made to FIGS. 19A and 19B, which are schematic illustrations of the paper covering 34 and heating element 32 of capsule 20, in accordance with some applications of the present invention. FIG. 19A shows the paper covering and metallic foil (acting as heating element 32) in a flattened configuration before smoking material has been inserted and the paper covering has formed a cylindrical housing for the smoking material. FIG. 19B shows the paper covering and the foil as configured after smoking material has been inserted and the paper covering has formed a cylindrical housing for the smoking material.

As described hereinabove, for some applications, the heating element comprises a metallic material, which is typically disposed within the capsule and/or is typically in direct contact with the smoking material, and that is heated via electrical resistive heating. For some applications, the heating element is a metal foil (e.g., stainless steel foil, nickel-titanium foil, titanium foil, copper foil, aluminum foil, steel foil) that typically is in direct contact with, and surrounds, the smoking material within portion 22 of capsule 20. For some applications, the foil has a thickness of more than 1 micron (e.g., more than 3 microns) and/or less than 20 microns (e.g., less than 10 microns), for example, 1-20 microns, or 3-10 microns. Typically, a current is applied along the length of portion 22 (e.g. with a positive electrode at the first end and a negative electrode at the second end, or vice versa) and airflow is parallel to the direction of the current flow. For some applications, a current is applied along the metallic foil along a length of portion 22 in an axial direction along the metallic foil (i.e., along a direction that is parallel to the longitudinal axis of the capsule) that is greater than 5 mm, e.g., greater than 15 mm. Typically, it is desirable for capsule 20 to have the general structure of a traditional cigarette. For some applications, the heating element extends along the entire length of the smoking-material-containing portion of the capsule. Alternatively, the heating element only extends along a portion of the length and/or the circumference of the smoking-material-containing portion of the capsule. For some applications, the heating element 32 (which is typically as described hereinabove) is printed and/or is adhered to the paper covering. Typically, at the locations at which the electrodes contact the capsule, the heating element is exposed to the electrodes, such as to make direct electrical contact with the electrodes.

As shown in FIGS. 19A-B, for some applications, the foil is adhered to the paper covering along only part of the length of portion 22 of the capsule. For some applications, the foil is not adhered to the paper covering around the full circumference of portion 22. For some applications, in order to form a cylindrical shape, there is a band 108 of overlap of the paper covering, in order to stick the paper covering to itself and form a closed cylinder. For some such applications, there is no foil within the band of overlap. For some applications, the paper covering defines openings 112 (e.g., holes or slits), in order to provide direct electrical contact between the electrodes and the foil.

Figure 20A:
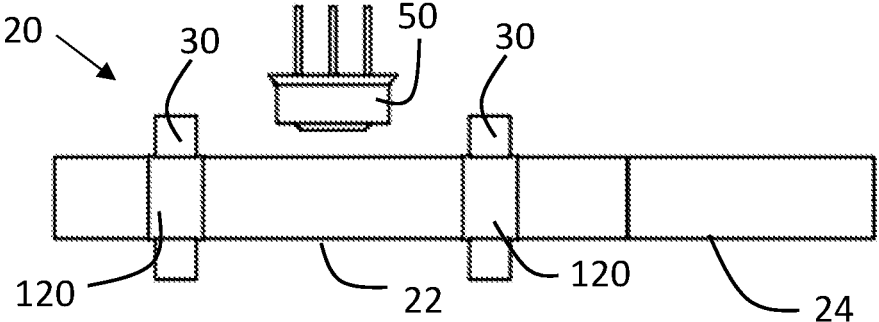
FIGS. 20A, 20B, and 20C are schematic illustrations of a capsule including an electrical contact coating at a region at which the capsule is configured to contact electrodes, in accordance with some applications of the present invention.
Figure 20B:
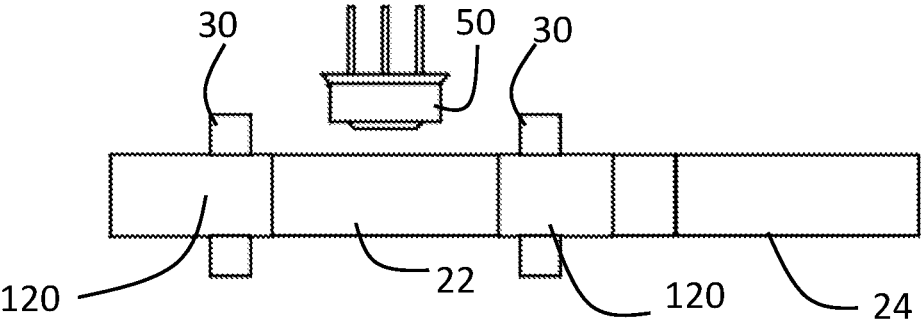
Figure 20C:
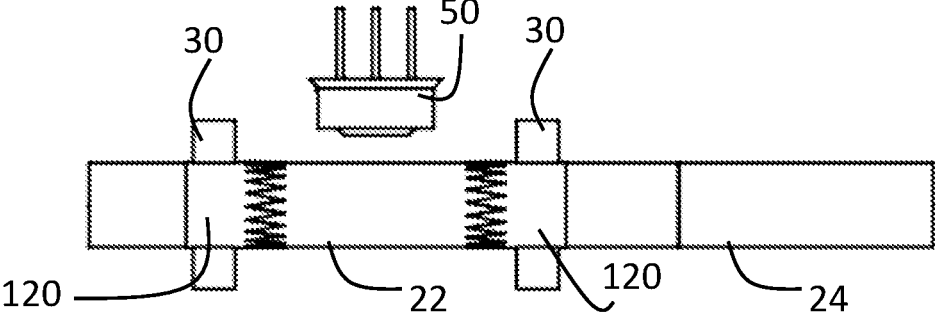

Reference is now made to FIGS. 20A, 20B, and 20C, which are schematic illustrations of capsule 20, the capsule including an electrical contact coating 120 at a region at which the capsule is configured to contact electrodes 30, in accordance with some applications of the present invention. For some applications, at a region at which the capsule is configured to contact electrodes 30, the capsule is coated with coating 120, which is configured to enhance the electrical contact between the electrode and the heating element. For example, the coating may be a gold or a copper coating, and may be an inner and/or an outer coating. For some applications, the coating has a lower resistance than that of metallic foil 32. Typically the coating extends until a region at which it is desirable for the heating element to be heating via electrical resistive heating. For some applications, the overall resistance of coating as well as that of the heating element is configured to provide a desired overall resistance, by configuring the materials, the thickness, and/or treatments that are applied to the coatings and/or to the heating element, as described in further detail hereinbelow. For example, the overall resistance may be configured to control the amount of heat that is generated, and/or to draw current from batteries of the smoking device in an efficient manner. For some applications, the overall resistance is set such as to substantially match the internal resistance of the (one or more) batteries of the smoking device, such that current is drawn from batteries of the smoking device in an efficient manner.

For some applications, the coating is configured to prevent the generation of hotspots at the region at which the capsule is configured to contact electrodes 30. For example, if there is suboptimal contact between an electrode and the heating element this can lead to the generation of a hotspot at the region at which the capsule is configured to contact electrodes 30, which can cause pyrolysis of the smoking material at the hotspot, and/or can lead to inadequate heating of the heating element. Typically, coating 120 is configured to prevent such hotspots from occurring.

For some applications, the coating is applied in a ring shape, as shown in FIGS. 20A and 20B. Alternatively, the coating is applied in a different shape. For example, the coating may have a zigzagged edge on the side at which the coating contacts the metallic foil (as shown in FIG. 20C), in order to conduct electrical current to the heating element in a uniform manner.

For some applications, the coating extends around the full circumference of the capsule, such that the coating diffuses the current, which is applied to the capsule by electrodes, uniformly around the circumference of the capsule. For some such applications, the smoking device includes only a single pair of electrodes disposed on one side of the capsule, rather than having a plurality of pairs of electrodes that are disposed at respective circumferential locations around capsule. For some such applications, the smoking device includes a pair of electrodes disposed on one side of the capsule and a pair of mechanical elements that are configured to apply mechanical pressure to the capsule on the other side of the capsule.

For some applications, the capsule has a structure as shown in FIGS. 19A-B, with the metallic foil being exposed via openings in the paper covering, and coating 120 is disposed outside the paper covering over the regions of the paper covering that define the openings. Thus, the coating electrically couples the electrodes to the metallic foil via the openings in the paper covering.

Figure 21A:
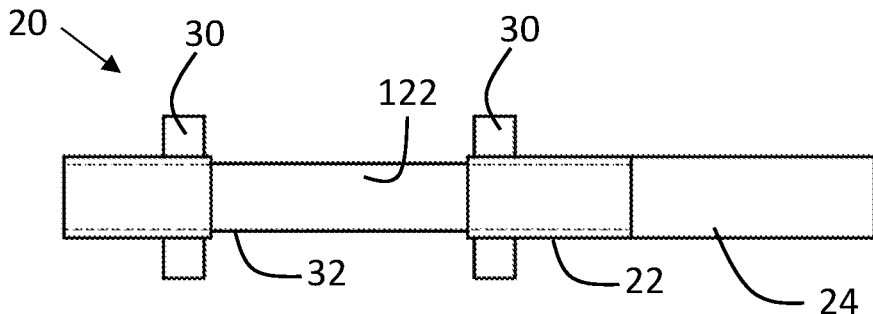
FIGS. 21A, 21B, and 21C are schematic illustrations of a the capsule including a region that surrounds the smoking material, at which a foil heating element has greater resistance than the resistance of the foil at the region at which the capsule is configured to contact electrodes, in accordance with some applications of the present invention.
Figure 21B:
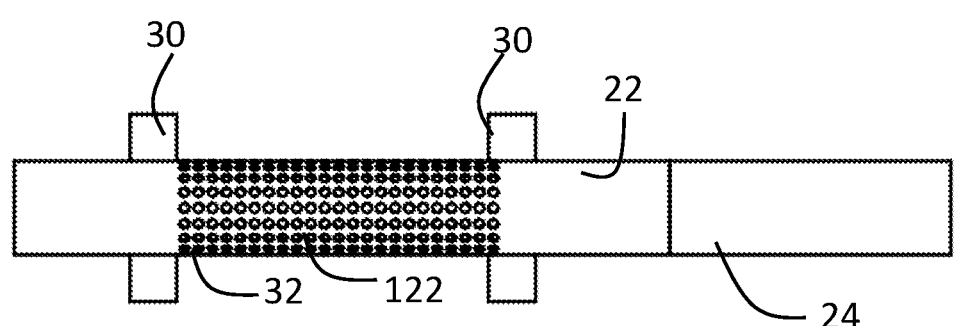
Figure 21C:
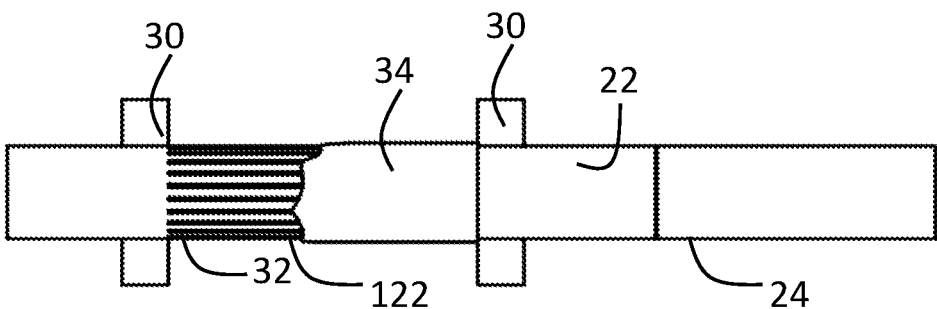

Reference is now made to FIGS. 21A, 21B, and 21C, which are schematic illustrations of capsule 20, the capsule including a region 122 that surrounds the smoking material, at which the metallic foil heating element has greater resistance than the resistance of the foil at the region at which the capsule is configured to contact electrodes 30, in accordance with some applications of the present invention. For some applications (as an alternative or in addition to coating the capsule at the region at which the capsule is configured to contact electrodes 30, as described with reference to FIGS. 20A-C), at the region at which the capsule is configured to contact electrodes 30, the foil is made thick enough to provide good electrical contact with the electrodes as well as relatively low resistance. However, within region 122, the foil has different characteristics in order to increase its resistance such as to lead to adequate resistive heating to heat the smoking material. For example, within region 122, the foil may be thinner than at the region at which the capsule is configured to contact electrodes 30, in order to increase its resistance within region 122, as shown in FIG. 21A. Alternatively or additionally, within region 122, the foil may be etched (e.g., to create openings (e.g., holes or slits) in the foil), in order to increase its resistance within region 122, as shown in FIG. 21B. Further alternatively or additionally, within region 122, the foil may have openings (e.g., holes or slits) cut from it, in order to increase its resistance within region 122, as shown in FIG. 21C. Typically, even at locations at which the foil defines openings (e.g., holes or slits), paper covering 34 does not define openings, as indicated in FIG. 21C. In this manner, the paper covering cover blocks radial airflow into the capsule, such that there is no (or minimal) radial airflow into the capsule, and substantially all of the airflow is along the axial direction. Alternatively, the openings within the foil are not covered, such as to allow radial airflow into the capsule.

For some applications, the metallic foil heating element is configured to provide a desired overall resistance, by configuring the materials, the thicknesses, and/or treatments that are applied to the foil. For example, the overall resistance may be configured to control the amount of heat that is generated, and/or to draw current from batteries of the smoking device in an efficient manner. For some applications, the overall resistance is set such as to match the internal resistance of the (one or more) batteries of the smoking device, such that current is drawn from batteries of the smoking device in an efficient manner.

Figure 22A:
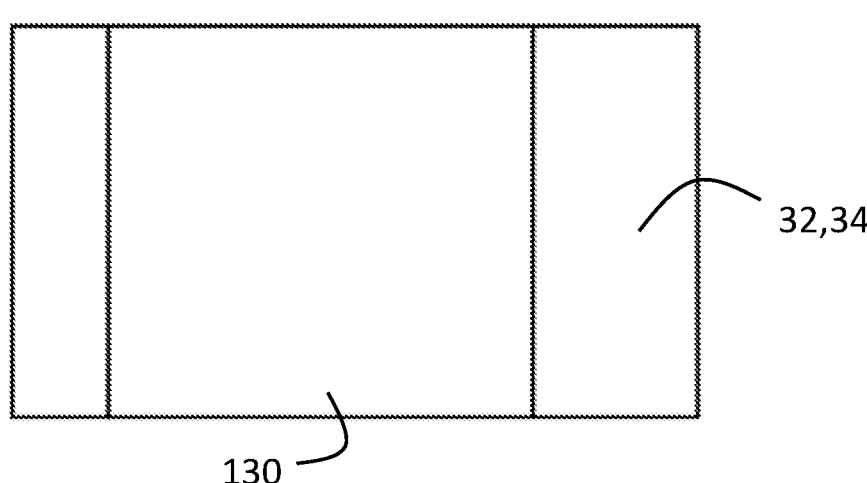
FIGS. 22A, 22B, 22C and 22D are schematic illustrations of a covering material of a capsule that includes an inner lining, in accordance with some applications of the present invention.
Figure 22B:
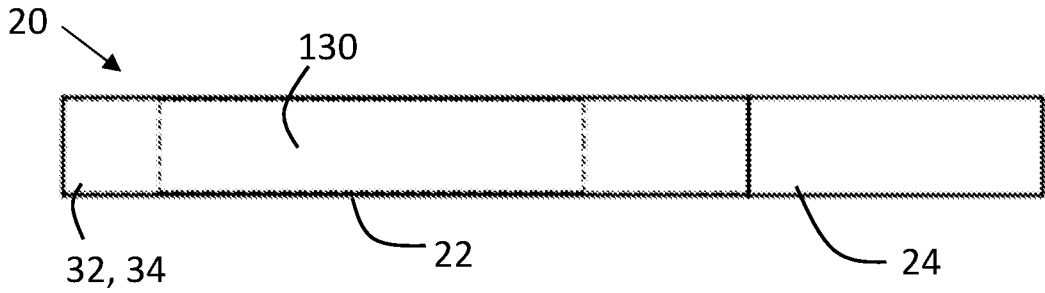
Figure 22C:
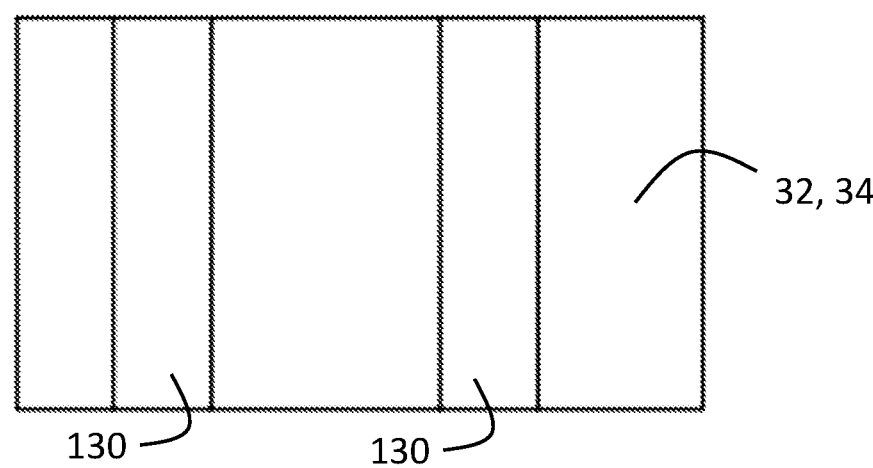
Figure 22D:
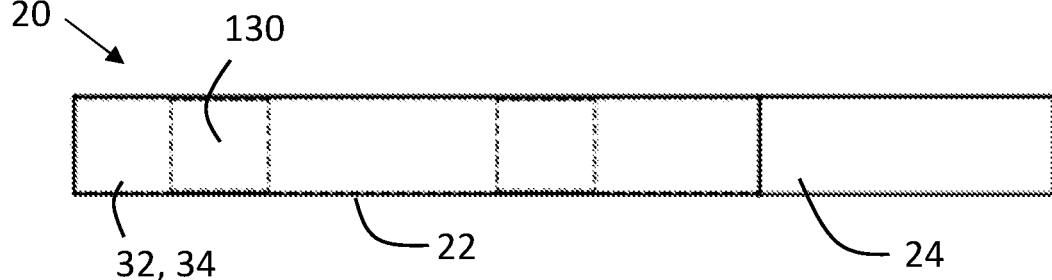

Reference is now made to FIGS. 22A, 22B, 22C and 22D, which are schematic illustrations of a covering material of capsule 20 (e.g., paper covering 34 and/or heating element 32), the covering material including an inner lining 130, in accordance with some applications of the present invention. Typically, the inner lining is flexible and is configured to diffuse heat that is generated by the heating element. For example, the inner lining may include polyimide. Typically, the inner lining acts as a barrier between the heating element and the smoking material, such that if heat isn't evenly generated across the heating element and/or if there are hotspots, the inner lining diffuses the heat across the smoking material. For some applications, the inner lining extends along a length of the capsule within which the smoking material is disposed, e.g., as shown in FIGS. 22A-B. For some applications, the inner lining is configured to add to the mechanical strength of the capsule, for example to prevent the capsule from tearing as a result of mechanical pressure that is applied to the capsule by electrodes 30. For some such applications, the inner lining is disposed at regions of the capsule that are configured to be compressed by the electrodes, as shown in FIGS. 22C-D.

For some applications, the inner lining is configured to diffuse one or more chemicals, such as flavoring, pharmaceuticals, and/or a vapor-generating chemical, such as glycerol. For some applications, the inner lining includes a phase-change material that is configured to prevent the temperature of the smoking material from exceeding the phase-change temperature of the phase-change material. Typically, the phase-change material is selected such as to prevent the temperature of the smoking material from exceeding a temperature at which the smoking material pyrolyzes. For some applications, the phase-change material is selected such as to maintain the temperature of the smoking material within an optimal range for vaporization and/or taste. For some applications the inner lining is configured to absorb chemicals that are generated by pyrolysis of the smoking material and/or other material within the capsule, such as nitric oxide and/or carbon monoxide.

Figure 23A:
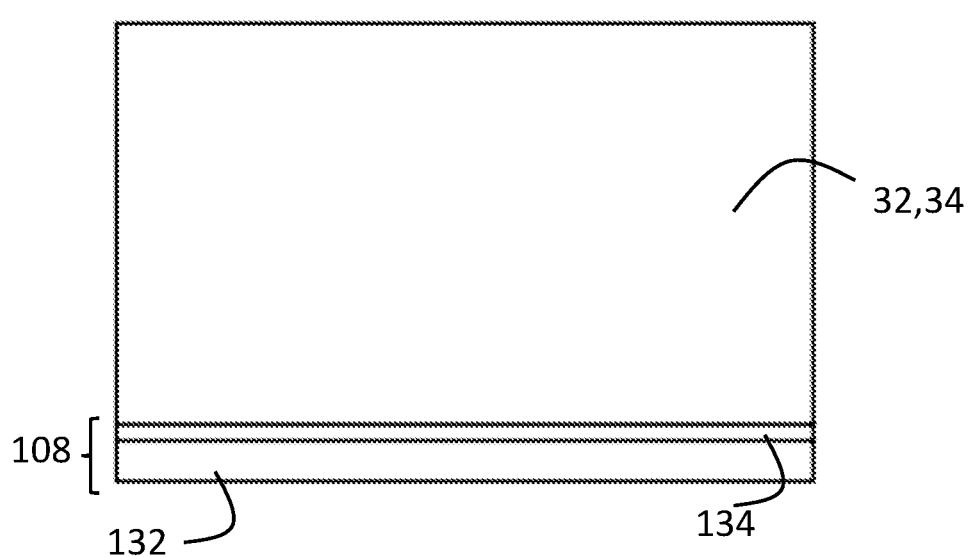
FIGS. 23A, 23B, 23C, 23D, 23E, and 23F are schematic illustrations of a covering material of a capsule that includes adhesive and/or additional material at a band of overlap of the covering material, in accordance with some applications of the present invention.
Figure 23B:
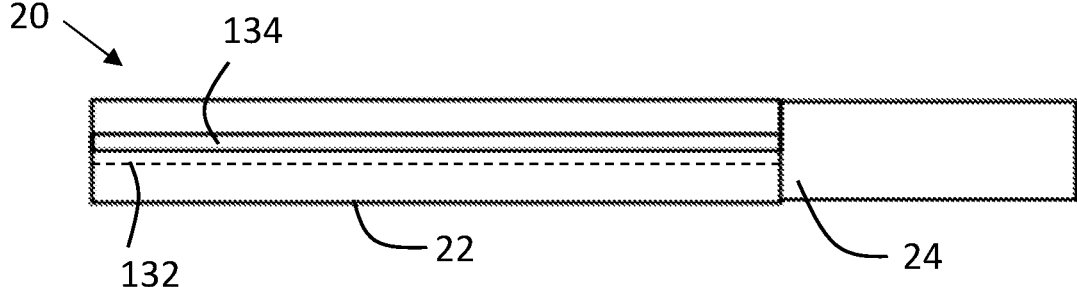
Figures 23C, 23D:
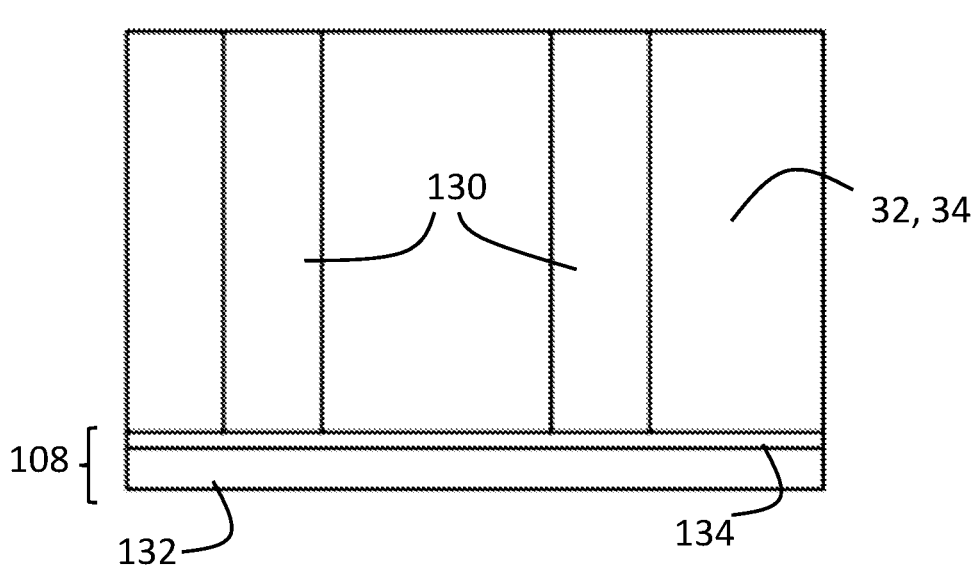

Reference is now made to FIGS. 23A, 23B, 23C, and 23D, which are schematic illustrations of a covering material of capsule 20 (e.g., paper covering 34 and/or heating element 32), the covering material including adhesive 132 and/or additional material at band 108 of overlap of the covering material, in accordance with some applications of the present invention. For some applications, the covering material is adhered to itself at the band of overlap in order to form a cylindrical shape that encases the smoking material (and/or additional elements, as described herein). For example, the adhesive may be liquid adhesive and/or double-sided adhesive. For some applications, the covering material is treated at the band of overlap in order to adhere it to itself (e.g., a UV treatment, or welding). For some applications, the covering material is treated so as to form a cylindrical shape even without having a band of overlap, e.g., via extrusion. For some applications, at least a portion of the covering material includes inner lining 130 as shown in FIGS. 23C and 23D, with the inner lining typically being as described above.

For some applications, at the band of overlap, the metallic foil and/or other conducting elements (e.g., conductive coatings) may be doubled, which can generate hotspots. For some applications, in order to prevent this, an adhesive is used that is an electrical insulator, such that the electrodes only apply current to the outer layer of the conducting elements, but the inner layer is electrically isolated from the electrodes. For some applications, an additional insulating material 134 (e.g., liquid polyimide) is added along at least a portion of the band of overlap.

Figure 23E:
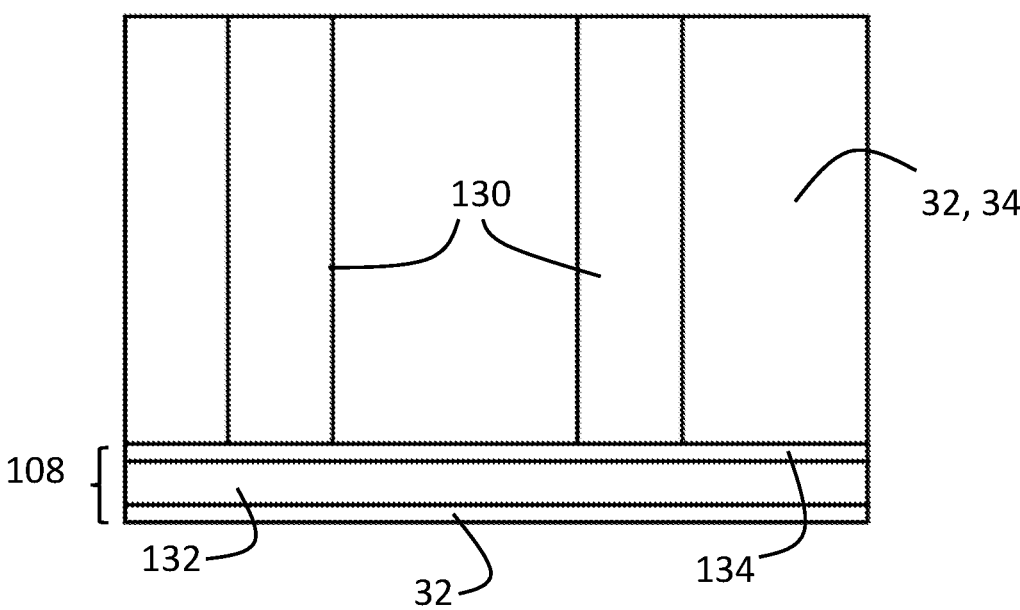
Figure 23F:
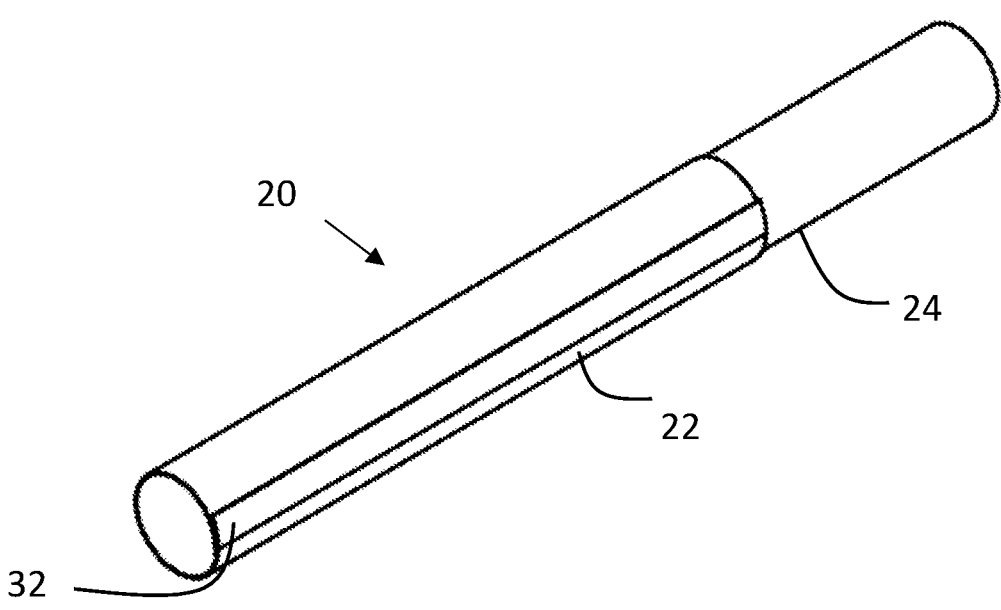

Reference is now made to FIGS. 23E and 23F, which are schematic illustrations of a covering material of capsule 20 (e.g., paper covering 34 and/or heating element 32), the covering material including adhesive 132 and/or additional material at band 108 of overlap of the covering material, in accordance with some applications of the present invention. The configuration of the covering material shown in FIGS. 23E-F is generally similar to that shown in FIGS. 23C-D, except that in the configuration shown in FIGS. 23E-F, there is a small band of heating element 32 (i.e., the metallic foil) which is configured to overlap with an inner layer of the heating element, when the covering material is made to overlap with itself such as to form a cylindrical shape. By being configured in this manner, even if one of the electrode pairs of the smoking device coincides with band 108 of overlap of the covering material, the electrodes still pass a current into the metallic foil at that circumferential location. Typically, in such cases, the electrode pair will drive the current into the outer layer of the metallic foil, which will then transfer the current to the inner layer of the metallic foil.

Figure 24A:
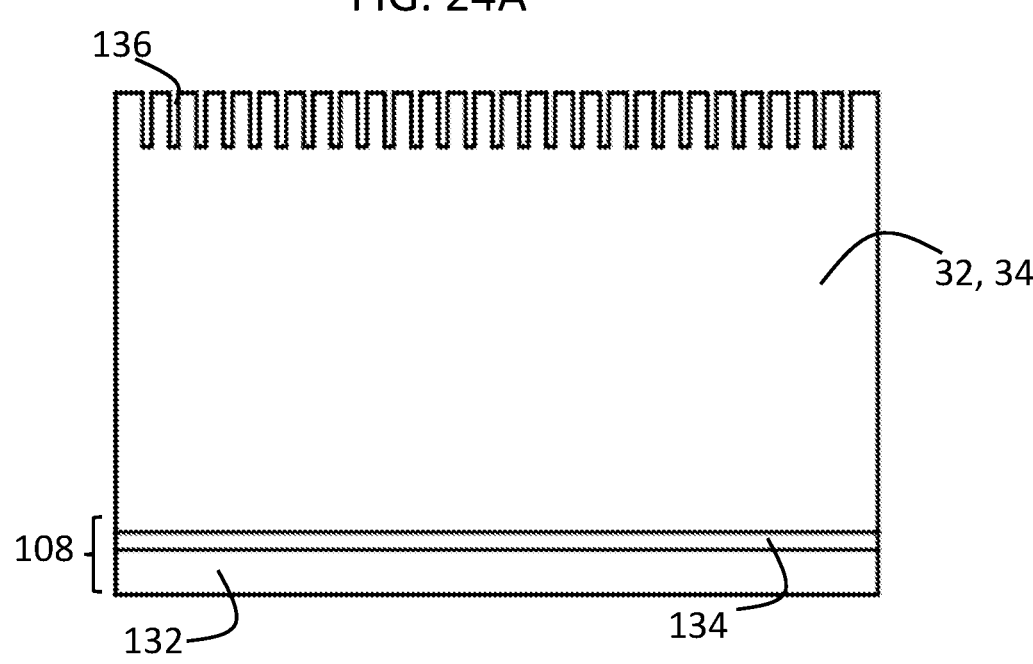
FIGS. 24A and 24B are schematic illustrations of a covering material of a capsule with slits formed in conducting elements at a band of overlap of the covering material, in accordance with some applications of the present invention.
Figure 24B:
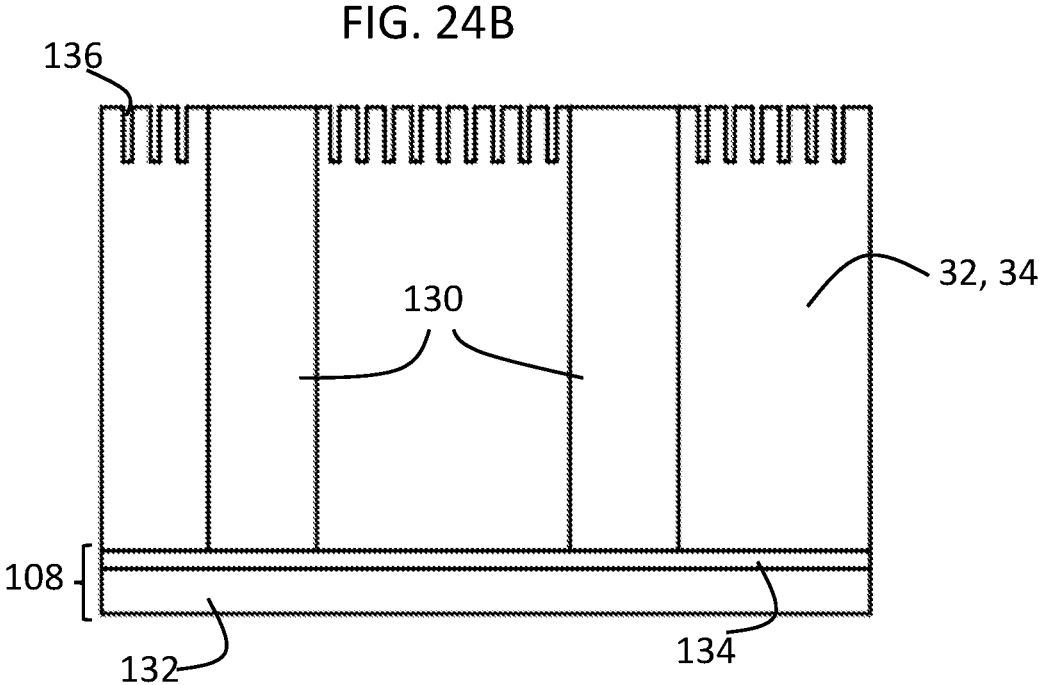

Reference is now made to FIGS. 24A and 24B, which are schematic illustrations of a covering material of capsule 20 (e.g., paper covering 34 and/or heating element 32), one or more slits 136 being formed in conducting elements (e.g., heating element 32) at band 108 of overlap of the covering material, in accordance with some applications of the present invention. For some applications, at the band of overlap, the metallic foil that typically comprises the heating element and/or other conducting elements (e.g., conductive coatings) may be doubled, which can generate hotspots. For some applications, along at least a portion of the band of overlap, slits 136 are made in the conducting elements in the circumferential direction, in order to increase resistance along the portion of the band of overlap. For some applications, at least a portion of the covering material includes inner lining 130 as shown in FIG. 24B, with the inner lining typically being as described above.

Referring again to FIGS. 19A-24B (which describe various outer coatings, inner linings, and apparatus and methods for forming a cylindrically-shaped capsule), it is noted that the scope of the present disclosure includes any one of the following capsule designs. In some applications, paper covering 34 covers at least a portion of the capsule. In some applications, the paper covering is adhered to itself along a band of overlap, such as to form a cylindrical shape, thereby making the capsule airtight (and thereby ensuring airflow in the axial direction of the cylindrical capsule).

For some applications, metallic foil (acting as heating element 32) is adhered to the inside of the paper covering. For some applications, the metallic foil overlaps with itself, as described hereinabove. For some applications, the extent of overlap of the paper covering and that of the metallic foil are not the same as each other. For some applications, the metallic foil does not overlap with itself at all. Typically, for such applications, the metallic foil still encompasses the full circumference of the capsule, by the two sides of the metallic foil contacting each other (but without overlapping with each other), such that a uniform resistance is provided by the metallic foil around the circumference of the capsule. For some such applications, the metallic foil is adhered to only a portion of the circumference of the paper covering, such that the paper covering overlaps with itself but the metallic foil does not (e.g., as shown in FIG. 19A). Typically, even in such cases, the paper covering is adhered to itself along the band of overlap, such as to form a cylindrical shape, thereby making the capsule airtight. For some applications, an inner lining (e.g., a strip of polyimide running along the length of portion 22 of the capsule) is used to hold the two sides of the metallic foil in place and to seal the capsule and make the airtight. For some applications, an inner lining is disposed along portions of the capsule at which the electrodes contact the metallic foil, in order to seal the capsule at these portions. For some applications, there is overlap between outer coatings or cover (e.g., the paper covering) and an inner lining, in order to ensure that the capsule is fully sealed.

Figures 25A, 25B, 25C:
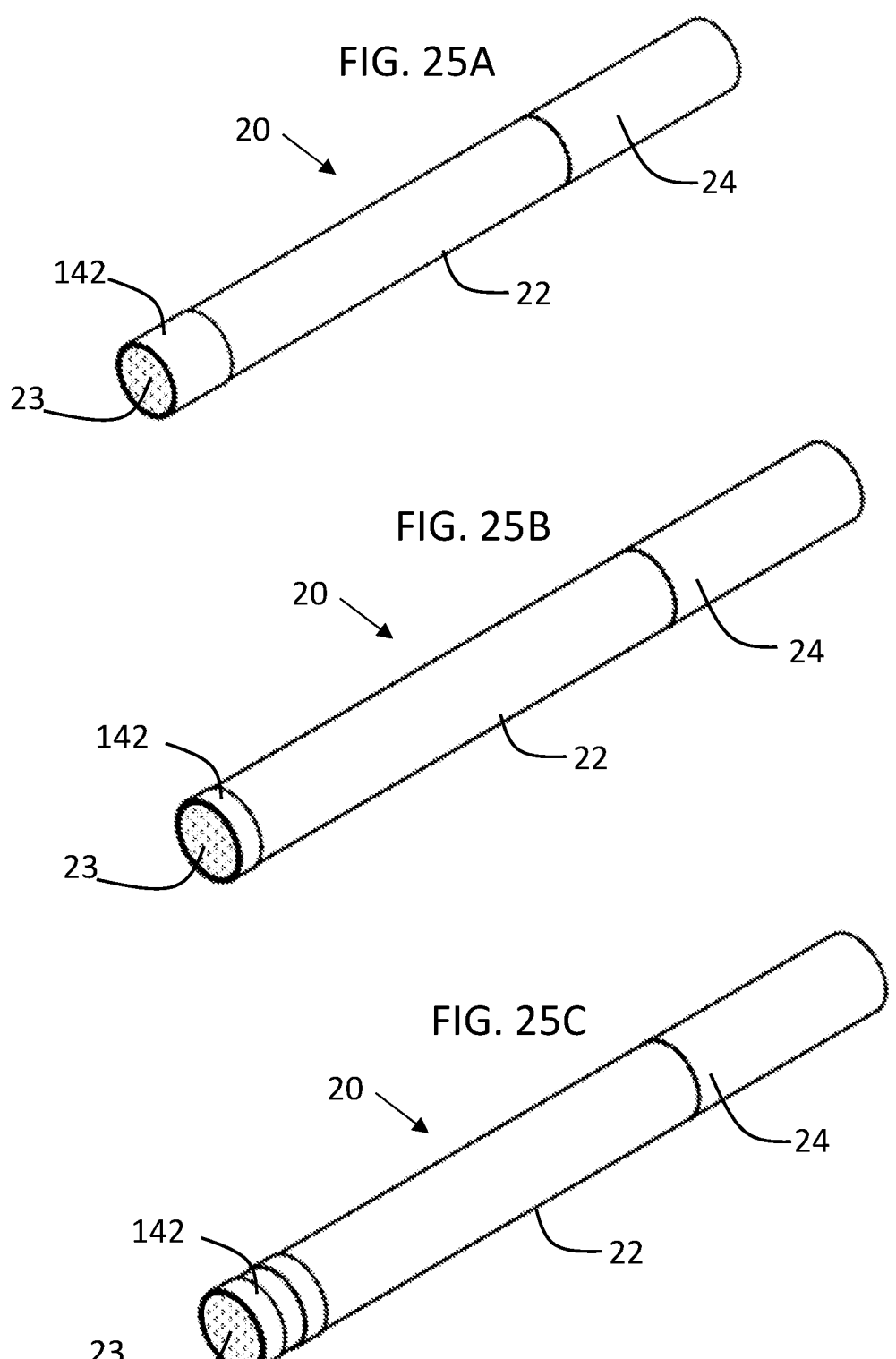
FIGS. 25A, 25B, and 25C are schematic illustrations of a capsule that includes one or more identifying features, in accordance with some applications of the present invention.

Reference is now made to FIGS. 25A, 25B, and 25C, which are schematic illustrations of capsule 20, the capsule including one or more identifying features 142, in accordance with some applications of the present invention. For some applications, smoking device 200 is configured to identify which type of capsule has been inserted and to operate in response to the type of capsule, for example, by heating the capsule to the vaporization temperature of the smoking material or according to a temperature profile that is suitable for the smoking material, controlling the amount of active agents that is vaporized, providing an output to the user regarding the category of capsule, etc. For some applications the identifying feature is a colored marking and the smoking device is configured to detect the color of the marking when the capsule is placed in the smoking device and/or during insertion of the capsule in the smoking device. For some applications, the identifying feature is a barcode, QR code, and/or a different type of patterned marking. For some applications, the identifying feature is a portion of the capsule that is configured to emit thermal radiation as the capsule is being heated. Typically, the smoking device includes an optical camera (e.g., a black-and-white camera) and/or a thermal camera that is configured to identify the aforementioned features. For some applications, the identifying feature is the resistance or a profile of resistance of the capsule. For example, the paper covering and/or a different insulating material may cover the metallic foil in a manner that defines a pattern of resistance that is identified by the smoking device. For some applications, the smoking device includes a sensor (such as an NFC antenna) that is configured to identify a package of capsules from which the capsule is sourced.

It is noted that although some applications of the present disclosure are described as being applied to a capsule that is provided to a user in a flattened configuration and/or is flattened by the smoking device, the scope of the present disclosure includes applying any one of the features of capsule 20 that are described herein to a cylindrical capsule that is configured to remain cylindrical even upon being inserted into the smoking device, mutatis mutandis. For example, any one of the features described with respect to the structure of the capsule, components of the capsule, coverings of the capsule, inner linings of the capsule, identifying features of the capsule, etc., are applicable to a cylindrical capsule that is configured to remain cylindrical even upon being inserted into the smoking device, mutatis mutandis.

Figure 26:
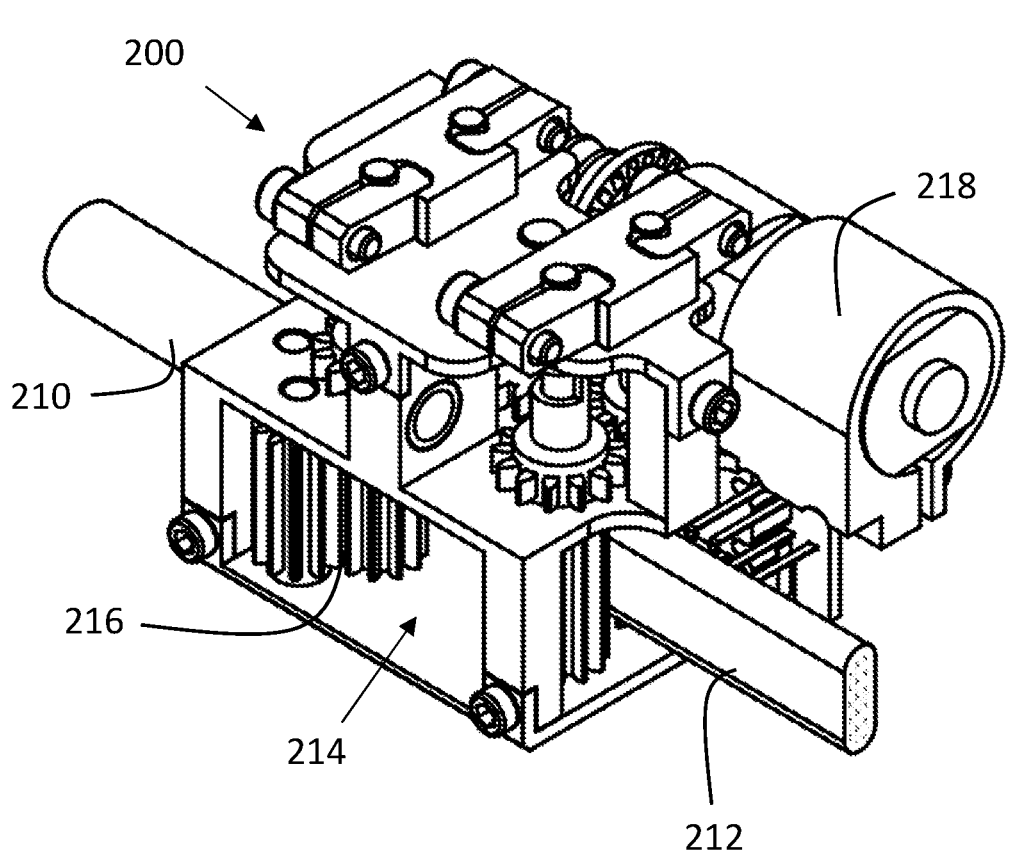
FIG. 26 is a schematic illustration of a smoking device with its cover removed (for illustrative purposes), in accordance with some applications of the present invention.

Reference is again made to FIGS. 1C and 1D, which show smoking device 200, which is configured for use with capsule 20. Reference is also made to FIG. 26, which is a schematic illustration of smoking device 200 with its cover removed (for illustrative purposes), in accordance with some applications of the present invention. Typically, the smoking device includes a button 204 and an indicator light 206 (shown in FIGS. 1C and 1D), e.g., a LED light. For some applications, the smoking device includes additional user interface components, e.g., a vibrating component. Typically, the smoking device includes a power source 237, e.g., one or more batteries (shown in FIGS. 29C and 29D), which are typically rechargeable via a charging port that is built into the device. Typically, the smoking device includes a control component 233 (e.g., a microprocessor and/or a microchip, shown in FIGS. 29C and 29D) that is configured to control heating of the capsule, identify the capsule, detect insertion of the capsule, detect puffs of the user (and/or lengths and/or depths of puffs), detect the temperature of the smoking material, and control heating of the smoking material in response thereto, as described in detail hereinabove. For some applications, the smoking device includes one or more sensors, such as an infrared temperature sensor, a thermal camera, a temperature sensor (such as a contact temperature sensor that measures the temperature of the smoking material by contacting the smoking material), and/or thermocouple sensor. For some applications, the smoking device is configured to detect electrical resistance of the capsule.

As described hereinabove, for some applications, the smoking device includes a plurality of temperature sensors, e.g., a plurality of infrared temperature sensors. For some applications, the smoking device is configured to detect puffs, lengths of puffs, and/or depths of puffs of the user and to control the heating of the smoking material or perform other functions responsively thereto. For some applications, the smoking device is configured to identify the capsule and to perform function responsively thereto. For some applications, the smoking device includes a sensor configured to detect patterns or colors, an optical camera (e.g., a black-and-white camera), a thermal camera, a sensor configured to detect resistance or conduction of given portions of the capsule. For some applications, the smoking device includes s sensor (such as an NFC antenna) that is configured to identify a package of capsules from which the capsule has been taken.

In accordance with respective applications, the smoking device is configured to flatten capsule 20, or is not configured to change the shape of capsule 20. For some applications, the smoking device is configured to heat the capsule via electrical resistive heating. Alternatively or additionally, the smoking device is configured to heat the capsule via magnetic induction heating. FIG. 26 shows an example of smoking device that is configured to flatten capsules. As shown, the capsule is configured to be inserted via a cylindrical insertion port 210, but portion 22 of the capsule (or a portion thereof) is housed within a non-cylindrical housing 212 (e.g., a housing having an elliptical, rectangular, pill-shaped, or racetrack-shaped cross-sectional shape) during heating of the smoking material, as described hereinabove. For some applications, the smoking device includes one or more mechanical elements 214 (e.g., gear wheels 216 and a motor 218, as shown) that are configured flatten the capsule. For some applications, the mechanical elements are configured to flatten the capsule by applying mechanical pressure to the sides of the capsule while the capsule is stationary. For some applications, the mechanical elements are configured to flatten the capsule by applying mechanical pressure to the sides of the capsule as the capsule moves from insertion port 210 into housing 212. For some applications, the smoking device includes a funnel, and is configured to flatten the capsule by passing the capsule through the funnel as the capsule moves from insertion port 210 into housing 212.

Figure 27A:
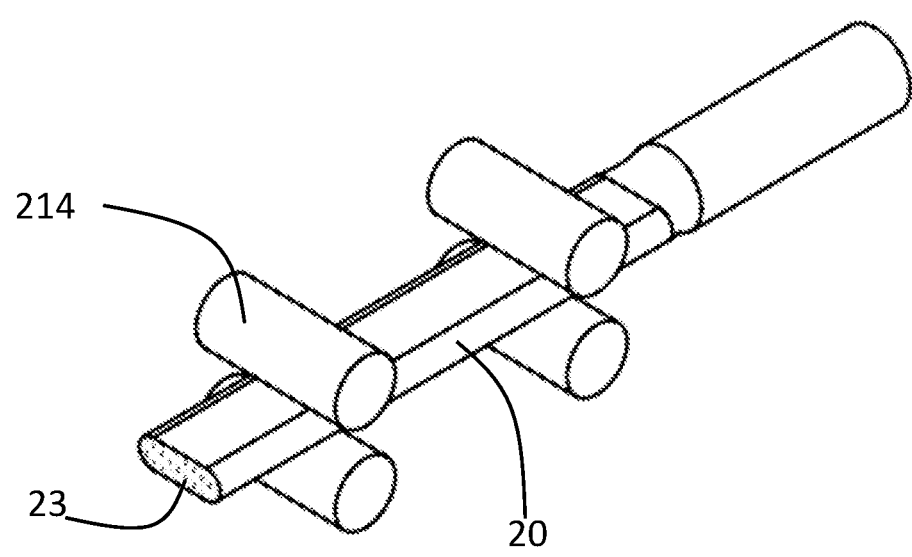
FIGS. 27A, 27B, 27C, 27D, 27E, and 27F are schematic illustrations of mechanical elements for flattening a portion of a capsule, in accordance with some applications of the present invention.
Figure 27B:
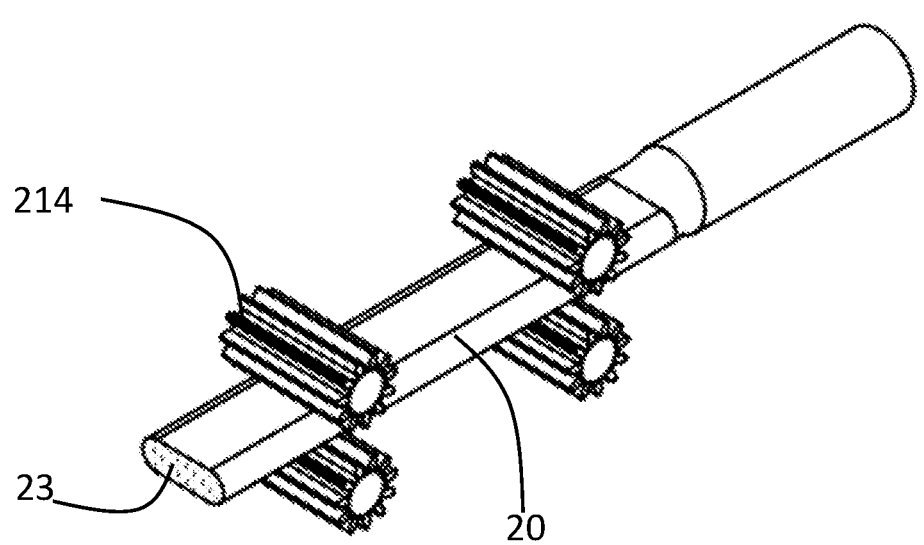
Figure 27C:
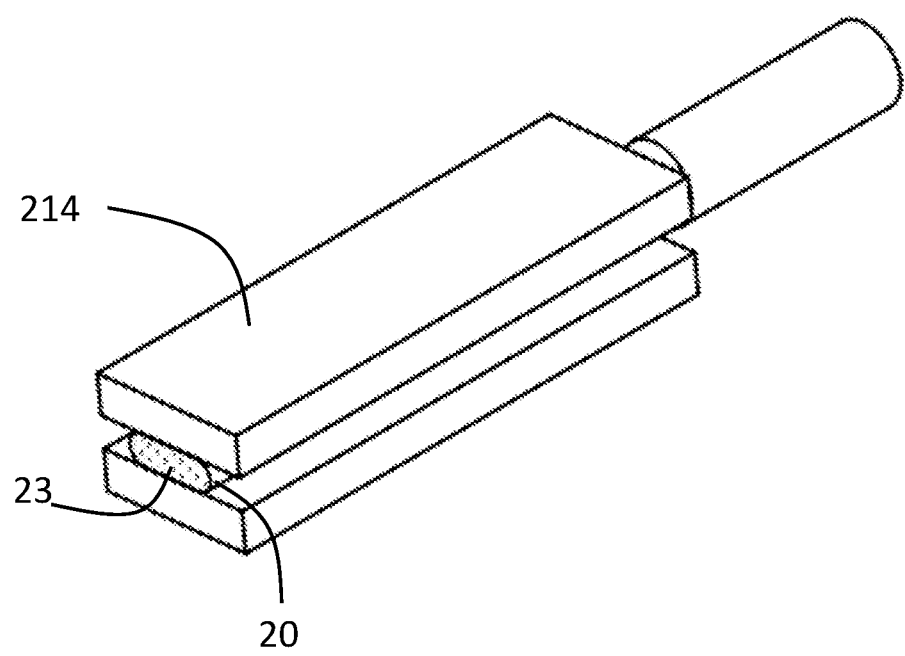
Figure 27D:
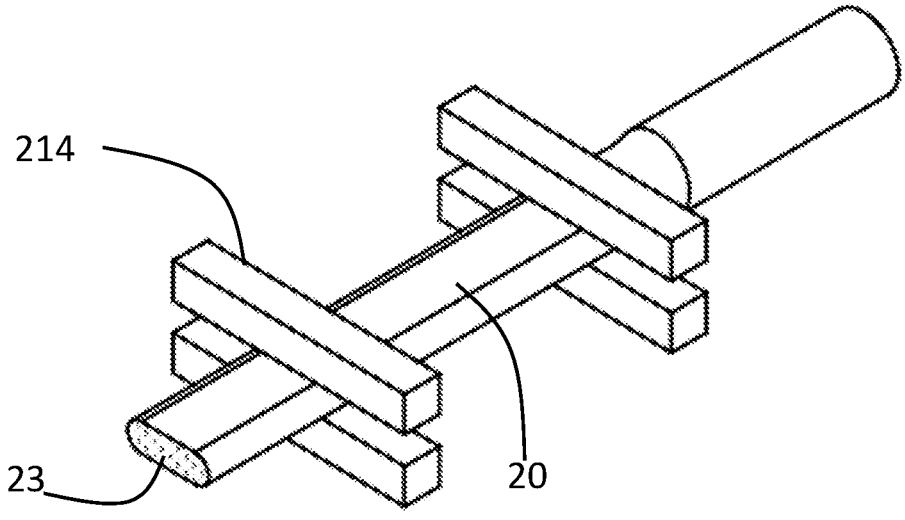
Figure 27E:
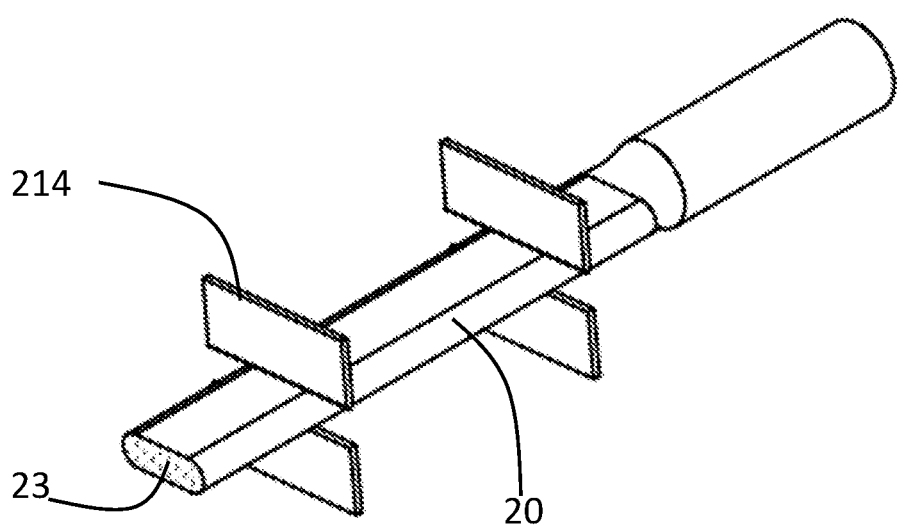

Reference is now made to FIGS. 27A, 27B, 27C, 27D, 27E, and 27F, which are schematic illustrations of mechanical elements 214 for flattening a portion of capsule 20, in accordance with some applications of the present invention. In accordance with respective embodiments, the mechanical elements may include one or more of wheels (FIG. 27A), gear wheels (27B), plates that are configured to apply even mechanical pressure along at least part of portion 22 of the capsule (FIG. 27C), cuboid elements that are configured to apply even mechanical pressure at discrete locations along of portion 22 of the capsule (FIG. 27D), and/or blade like elements (FIG. 27E). For some applications, the mechanical elements also function as electrodes and heat the smoking material via resistive heating of a heating element inside the capsule, as described in detail hereinabove. Thus, the electrodes serve a dual function of heating the smoking material via resistive heating of a heating element inside the capsule and of flattening a portion of the capsule via mechanical pressure.

For some applications, an area of contact between mechanical elements 214 and the capsule is minimized in order to reduce the loss of thermal energy from the capsule via this contact area. For some applications, thermally-insulating material is disposed between the mechanical elements and the capsule over at least a portion of the area of contact, in order to reduce the loss of thermal energy from the capsule via this contact.

Figure 27F:
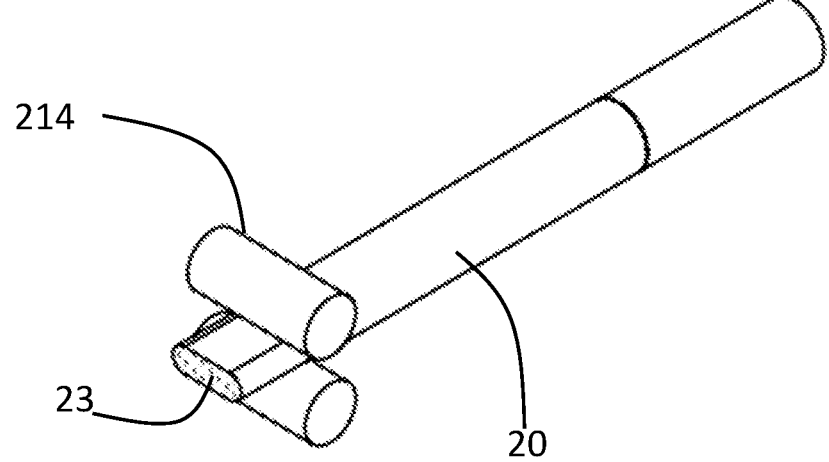

For some applications, mechanical elements (such as roller wheels, as shown in FIG. 27F) are used to flatten at least a part of portion 22 of the capsule, by rolling over the capsule as the capsule is being inserted into the smoking device. For some applications, the roller wheels assist in the axial insertion of the capsule.

Figure 28:
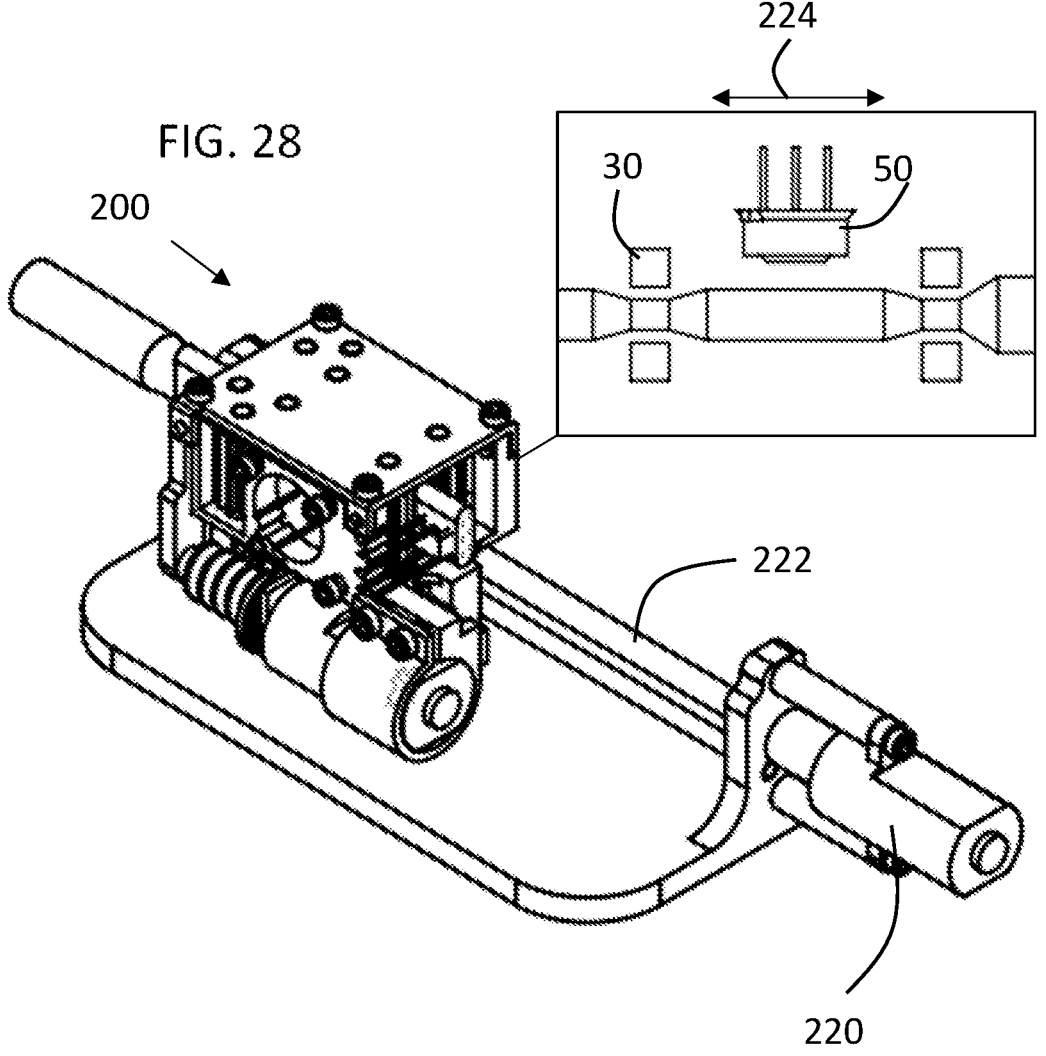
FIG. 28 is a schematic illustration of a smoking device that includes electrodes and/or mechanical elements that are configured to move axially relative to a capsule, in accordance with some applications of the present invention.

Reference is now made to FIG. 28, which is a schematic illustration of smoking device 200, the smoking device including electrodes 30 and/or mechanical elements 214 that are configured to move axially relative to capsule 20, in accordance with some applications of the present invention. For some applications, the smoking device includes a motor 220 which is configured to slide electrodes 30 and/or mechanical elements axially along a rail 222 relative to capsule 20. For some applications, the mechanical elements 214 flatten the capsule as they move over the capsule. For some applications, as the electrodes move, sensor 50 is moved with them, as indicated by arrow 224. The scope of the present disclosure includes electrodes that are configured to move axially relative to the capsule (e.g., using a generally similar mechanism to that shown in FIG. 28), one or more sensors that are configured to move configured to move axially relative to the capsule (e.g., using a generally similar mechanism to that shown in FIG. 28), or both one or more sensors and electrodes that are configured to move axially relative to the capsule (e.g., using a generally similar mechanism to that shown in FIG. 28). For some applications, the one or more sensors and electrodes are configured to move axially relative to the capsule together with each other (e.g., using a generally similar mechanism to that shown in FIG. 28).

Figure 29A:
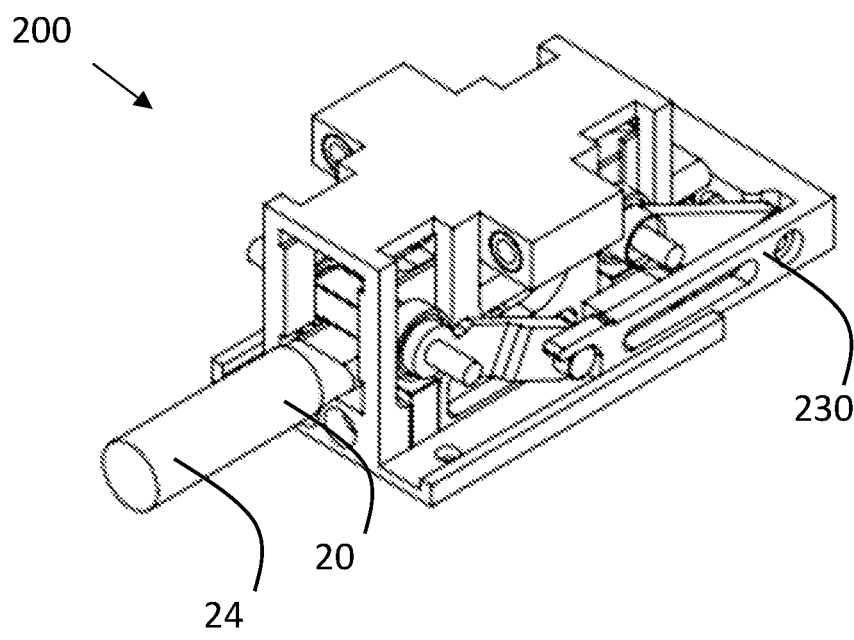
FIGS. 29A and 29B are schematic illustrations of a smoking device that includes a mechanism that is configured to bring electrodes and/or mechanical elements into pressurized contact with a capsule, in accordance with some applications of the present invention.
Figure 29B:
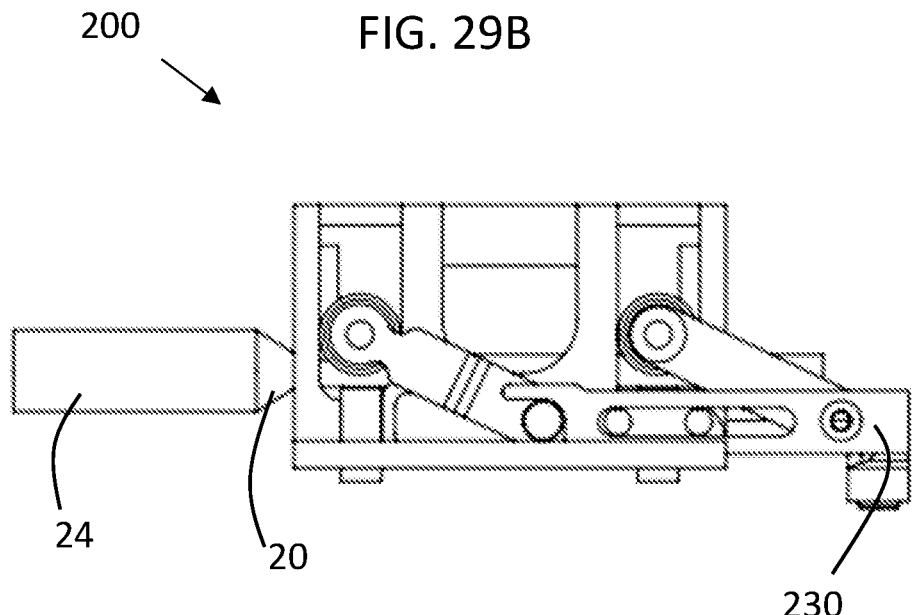

Reference is now made to FIGS. 29A and 29B, which are schematic illustrations of smoking device 200, the smoking device including a mechanism 230 that is configured to bring electrodes 30 and/or mechanical elements 214 into pressurized contact with capsule 20, in accordance with some applications of the present invention. For some applications, the mechanism is configured to bring electrodes 30 into pressurized contact with capsule 20, in order to enhance electrical contact between the electrodes and the heating element of the capsule. Alternatively or additionally, mechanism 230 is configured to bring mechanical elements 214 into pressurized contact with capsule 20 in order to flatten a portion of the capsule. As noted above, for some applications, the electrodes function as the mechanical elements.

Figure 29C:
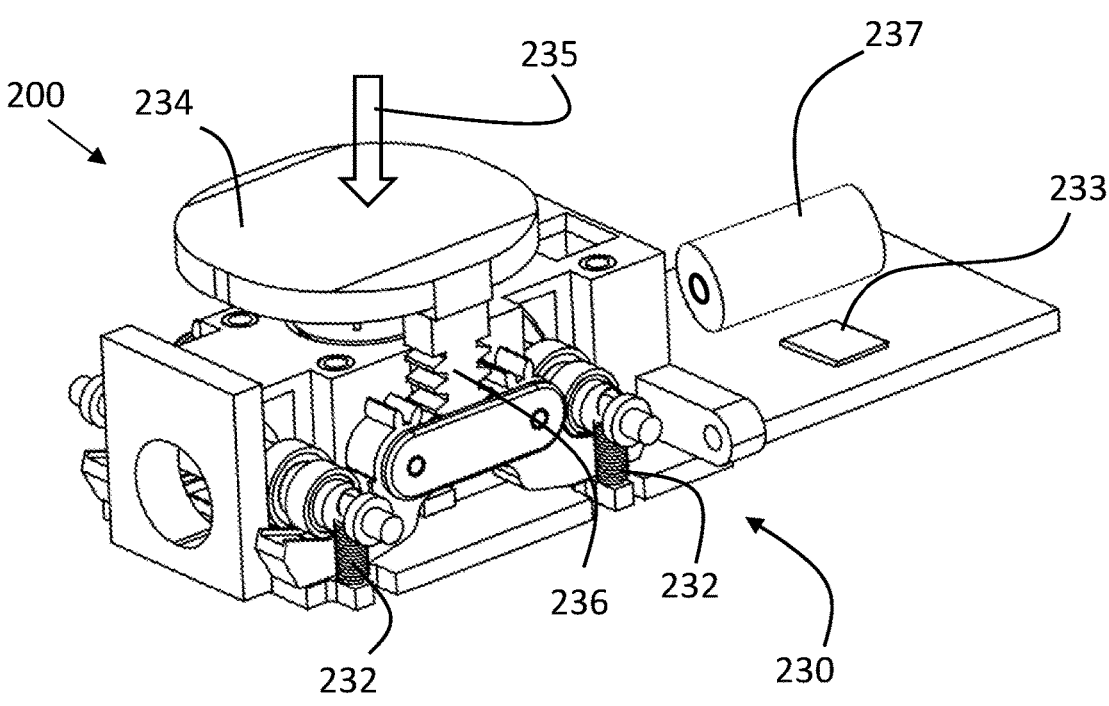
FIGS. 29C and 29D are schematic illustrations of a smoking device that includes a mechanism that is configured to bring electrodes and/or mechanical elements into pressurized contact with a capsule, in accordance with some further applications of the present invention.
Figure 29D:
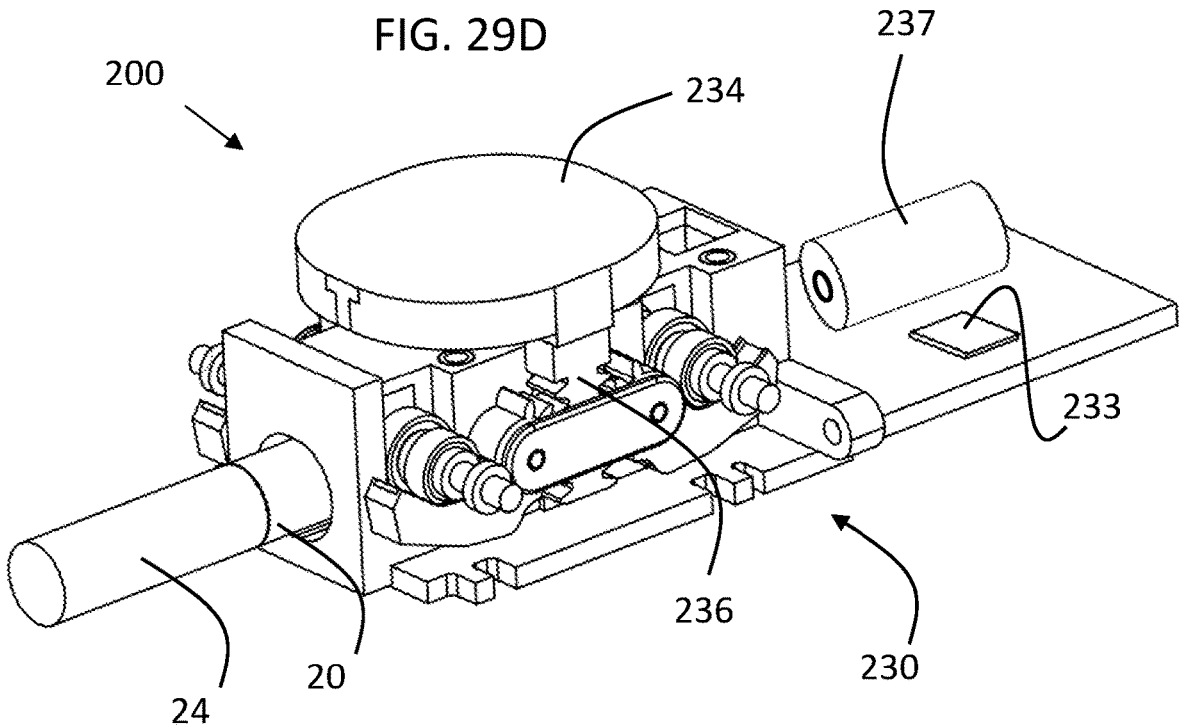

Reference is now made to FIGS. 29C and 29D, which are schematic illustrations of smoking device 200, the smoking device including a mechanism 230 that is configured to bring electrodes 30 and/or mechanical elements 214 into pressurized contact with capsule 20, in accordance with some applications of the present invention. For some applications, the mechanism is configured to bring electrodes 30 into pressurized contact with capsule 20, in order to enhance electrical contact between the electrodes and the heating element of the capsule. Alternatively or additionally, mechanism 230 is configured to bring mechanical elements 214 into pressurized contact with capsule 20 in order to flatten a portion of the capsule. As noted above, for some applications, the electrodes function as the mechanical elements. For some applications, mechanism 230 includes one or more compression springs 232 that are configured to generate a counterforce in response to being compressed. For some such applications, smoking device 200 includes a button 234 that is coupled to a gear track 236. Typically, the smoking device is configured such that insertion of capsule 20 requires button 234 to be pressed (as indicated by arrow 235 in FIG. 29C). Further typically, the pressing of the button causes compression of the compression springs, such that upon release of the button, the compression springs bring the electrodes into pressurized contact with the capsule (i.e., the configuration shown in FIG. 29D). It is noted that the compression springs are not visible in FIG. 29D.

Typically, the smoking device includes a control component 233 (e.g., a control chip and/or a control microprocessor) and a power source 237 (e.g., one or more batteries), both of which are shown in FIGS. 29C and 29D. For some applications, the one or more batteries are chargeable and the smoking device includes a charging port for charging the one or more batteries.

Figure 30A:
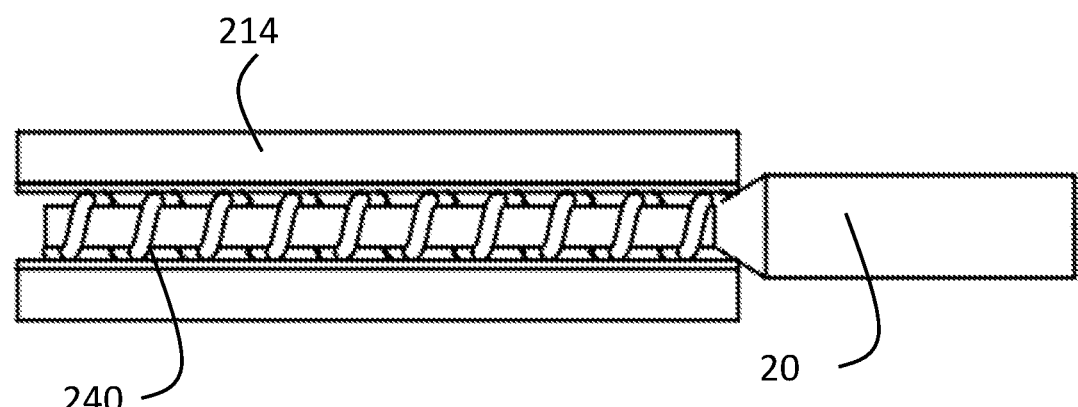
FIGS. 30A and 30B are schematic illustrations of a coil of a smoking device that is configured to be flattened by mechanical elements, in accordance with some applications of the present invention.
Figure 30B:
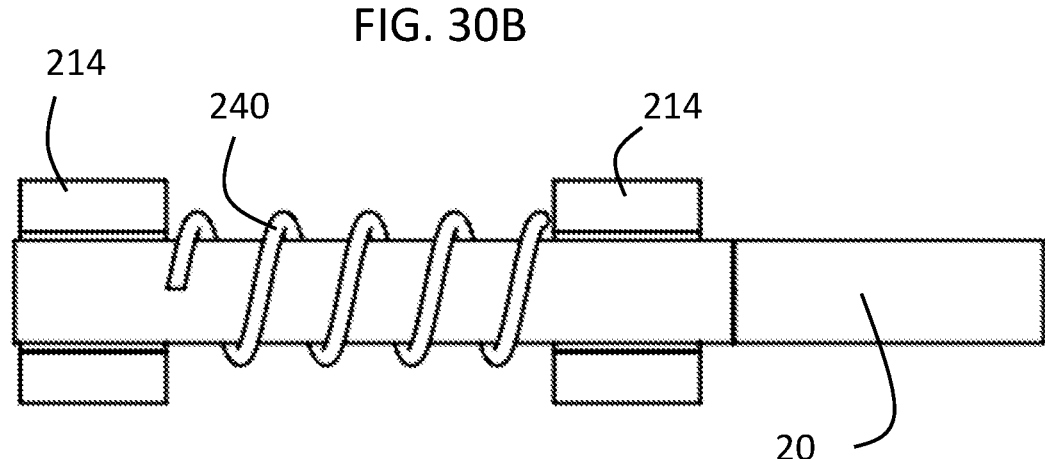

Reference is now made to FIGS. 30A and 30B, which are schematic illustrations of a coil 240 of smoking device 200 that is configured to be flattened by mechanical elements 214, in accordance with some applications of the present invention. As described hereinabove, for some applications, smoking device 200 includes a coil that is configured to generate an electromagnetic field. The coil is configured to heat one or more magnetically-heated materials (i.e., materials that are susceptible to being heated by a magnetic field (such as, magnetic materials and/or ferromagnetic materials)) within the capsule via magnetic induction. Typically, the control component of the smoking device drives an electric current through the coil in order to generate the magnetic field. In accordance with some applications, the magnetically-heated material is configured as a magnetically-heated rod 42 that is disposed along the length of the capsule (as shown in FIG. 7A), a magnetically-heated strip 44 that is disposed along the length of the capsule (as shown in FIG. 7B), a magnetically-heated tube 46 that is disposed along the length of the capsule (shown in FIG. 7C), and/or a plurality of magnetically-heated particles 48 (e.g., balls or beads) that are dispersed within the smoking material (as shown in FIG. 7D). Alternatively or additionally, a magnetically-heated material is disposed around the smoking material (e.g., underneath a paper covering), in a similar manner to that described with reference to the metallic foil that is heated via electrical resistive heating.

For some such applications, coil 240 has a circular cross section, and the coil is flattened by the mechanical elements 214 together with a portion of the capsule, subsequent to the portion of the capsule having been placed within the coil, as shown in FIG. 30A-B. The circular-cross-section of the coil typically facilitates easy insertion of the capsule to within the coil, while the flattened configuration of the capsule (and the coil) during heating of the smoking material facilitates the heating of the smoking material. For some applications, the flattened configuration of the capsule during heating of the smoking material facilitates the heating of the smoking material by reducing the distance between the magnetically-heated particles and the smoking material, as described hereinabove. For some applications, the flattened configuration of the coil facilitates the heating of the smoking material by reducing the cross-sectional area of the coil, thereby increasing the magnetic flux density through the coil relative to a coil that has a larger cross-section at a similar electrical current.

For some applications, coil 240 is integrated into a sleeve or tube within smoking device 200. Alternatively or additionally, the coil includes an inner and/or an outer lining (e.g., a polyimide inner and/or outer coating).

Figure 31A:
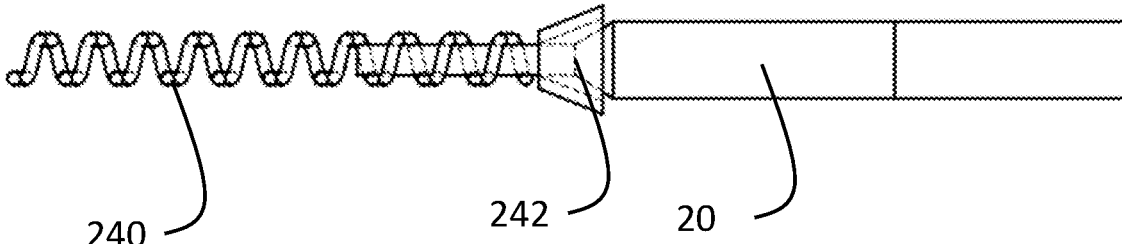
FIGS. 31A, 31B, 31C, and 31D are schematic illustrations of a coil of a smoking device that is pre-shaped in a flattened configuration, in accordance with some applications of the present invention.
Figure 31B:
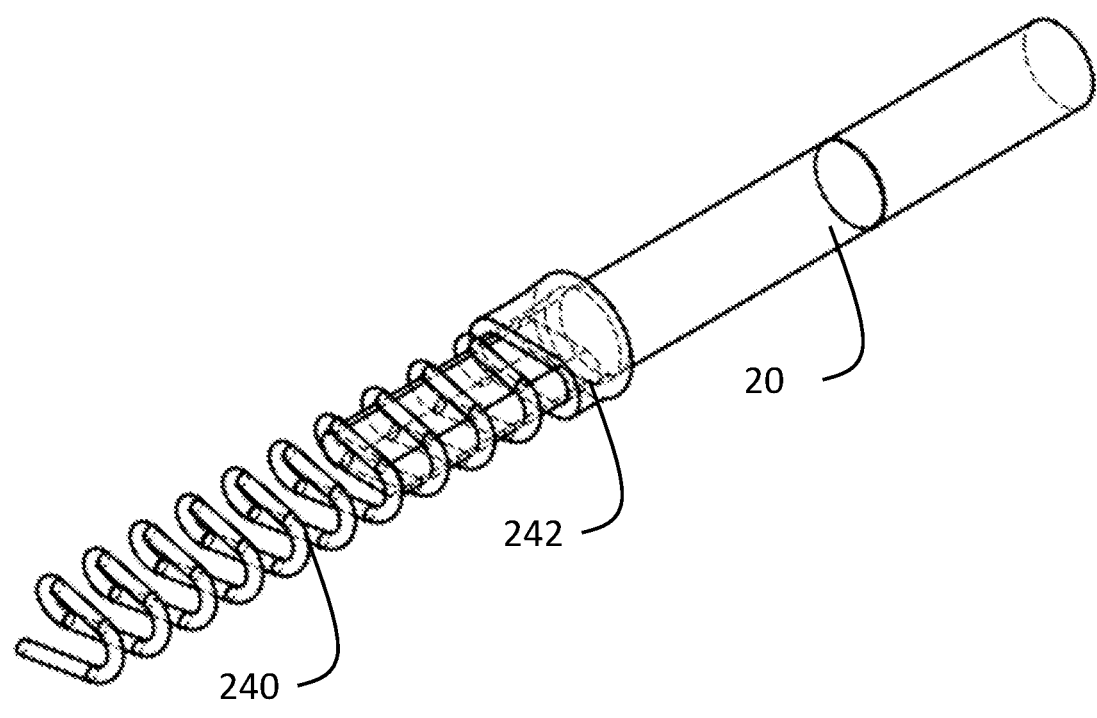
Figure 31C:
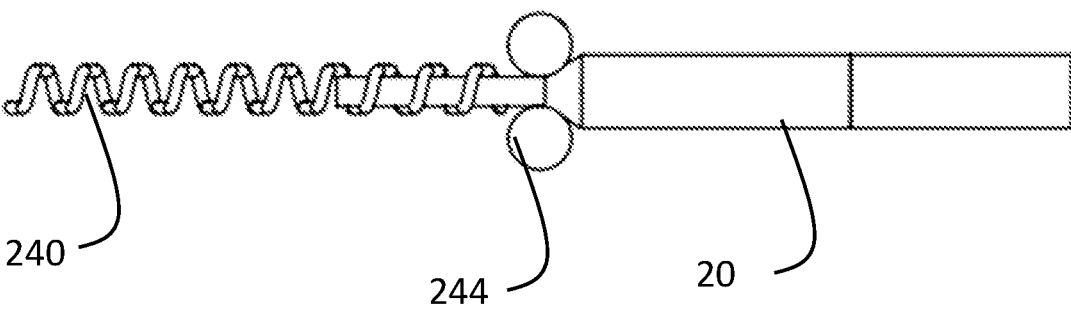
Figure 31D:
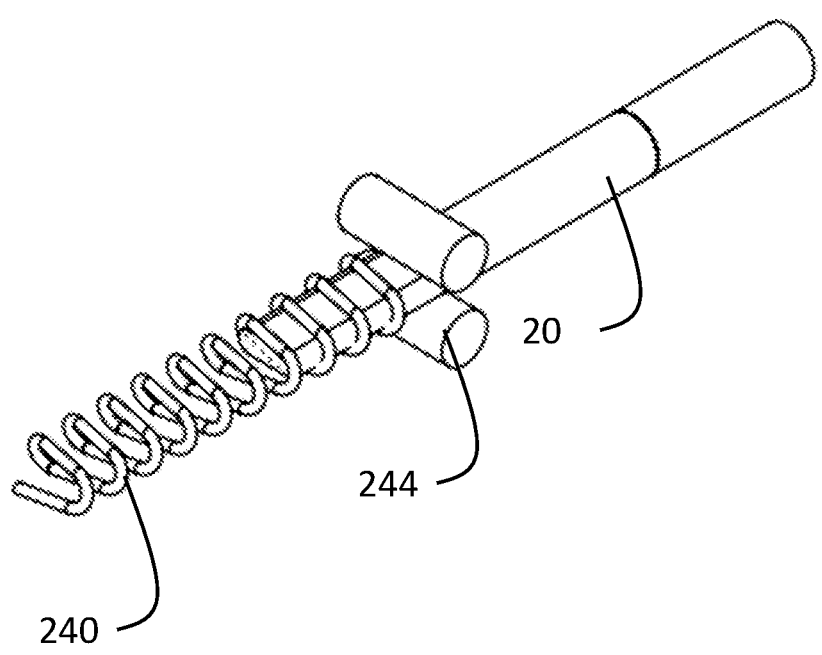

Reference is now made to FIGS. 31A, 31B, 31C, and 31D which are schematic illustrations of coil 240 of smoking device 200 that is pre-shaped in a flattened configuration (i.e., such that it is in the flattened configuration even in the absence of mechanical force acting on the coil), in accordance with some applications of the present invention. For some applications, a portion of the capsule is flattened as it is being inserted into the coil. For example, the portion of the capsule may be flattened via a funnel 242 (as shown in FIGS. 31A-B), and or by roller wheels 244 (as shown in FIGS. 31C-D). As described with reference to FIGS. 30A-B, for some applications, the flattened configuration of the capsule during heating of the smoking material facilitates the heating of the smoking material by reducing the distance between the magnetically-heated particles and the smoking material. For some applications, the flattened configuration of the coil facilitates the heating of the smoking material by reducing the cross-sectional area of the coil, thereby increasing the magnetic flux density through the coil relative to a coil that has a larger cross-section at a similar electrical current.

Figure 32A:
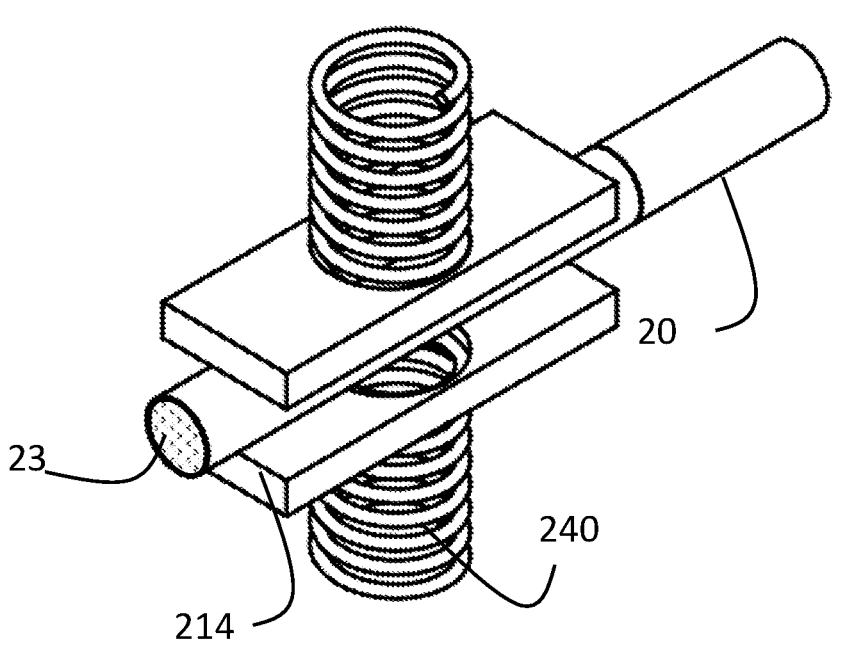
FIGS. 32A and 32B are schematic illustrations of a coil of a smoking device, in accordance with some applications of the present invention.
Figure 32B:
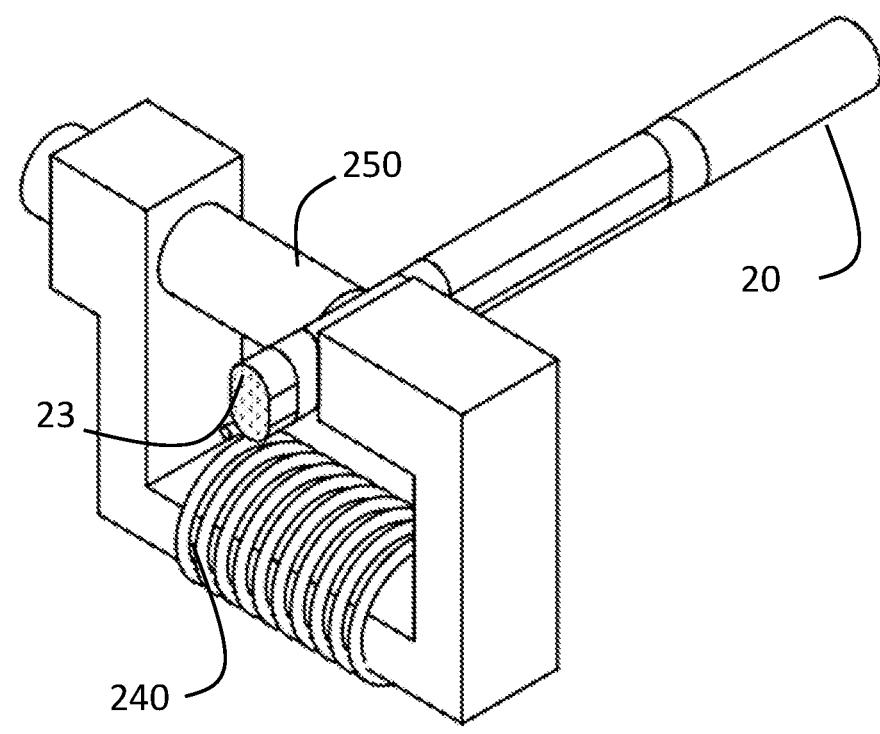

Reference is now made to FIGS. 32A and 32B, which are schematic illustrations of coil 240 of smoking device 200, in accordance with some applications of the present invention. For some applications, the capsule is not inserted into coil 240. For example, the axis of the coil may be perpendicular to the axis of the capsule and intersect the axis of the capsule (as shown in FIG. 32A), or the axis of the coil may be perpendicular with the axis of the capsule and not intersect the axis of the capsule (as shown in FIG. 32B). For some applications a material 250 with high magnetic permeability directs the magnetic field to the capsule, as shown in FIG. 32B. For some applications, material 250 is shaped in to define a magnetic circuit, with the capsule being inserted into a gap in the circuit. For some such applications, material 250 is configured to apply mechanical pressure to at least a portion of the capsule, thereby flattening the portion capsule, as shown in FIG. 32B. For some applications, the flattened configuration of the capsule during heating of the smoking material facilitates the heating of the smoking material by reducing the distance between the magnetically-heated particles and the smoking material, as described hereinabove. For some applications, by flattening the capsule, the gap in the magnetic circuit defined by material 250 is reduced, thereby increasing the magnetic permeability of the magnetic circuit and increasing magnetic flux through the capsule, relative to if the gap was larger.

Figure 33:
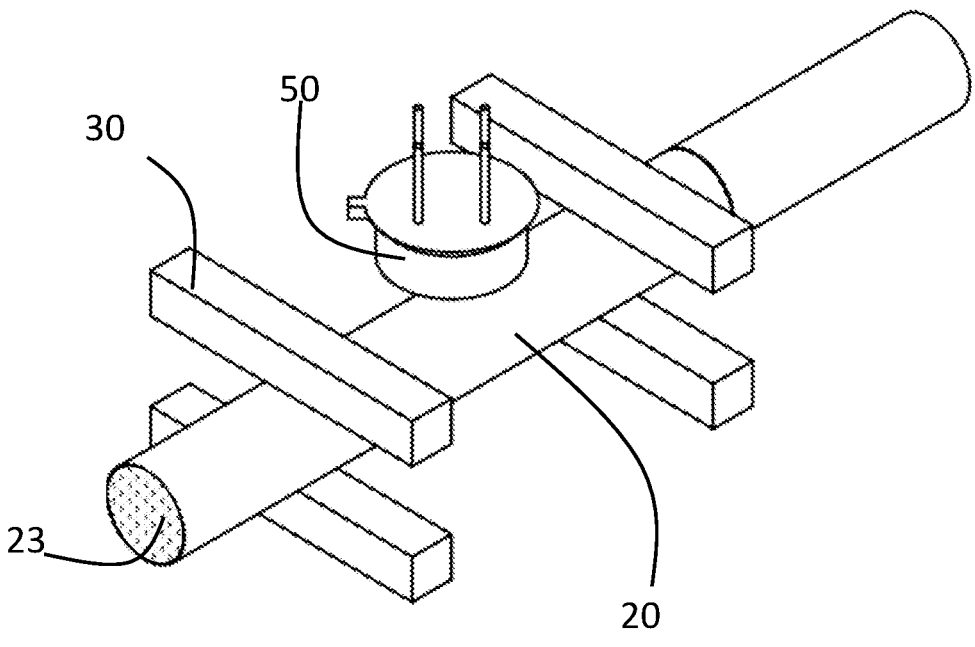
FIG. 33 is a schematic illustration of a capsule being heated, while the capsule is in a non-flattened, cylindrical shape, in accordance with some applications of the present invention.

Reference is now made to FIG. 33, which is a schematic illustration of capsule 20 being heated, while the capsule is in a non-flattened, cylindrical shape, in accordance with some applications of the present invention. As noted hereinabove, although some applications of the present disclosure are described as being applied to a capsule that is provided to a user in a flattened configuration and/or is flattened by the smoking device, the scope of the present disclosure includes applying any one of the features of capsule 20 that are described herein to a cylindrical capsule that is configured to remain cylindrical even upon being inserted into the smoking device, mutatis mutandis. For example, any one of the features described with respect to the structure of the capsule, components of the capsule, coverings of the capsule, inner linings of the capsule, identifying features of the capsule, etc., are applicable to a cylindrical capsule that is configured to remain cylindrical even upon being inserted into the smoking device, mutatis mutandis.

Figure 34:
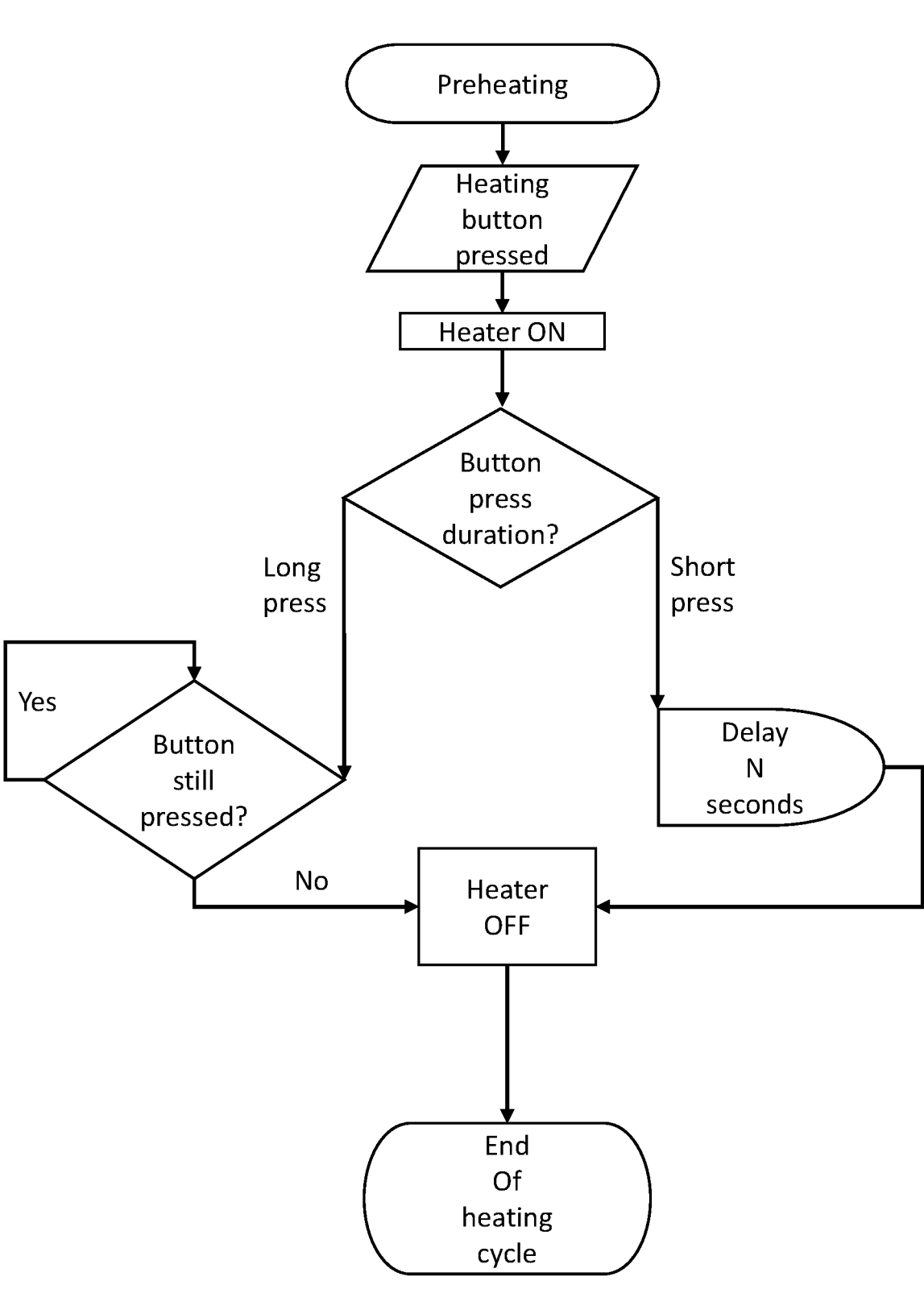
FIG. 34 is a flowchart showing steps that are performed by a smoking device, in accordance with some applications of the present invention.

Reference is now made to FIG. 34, which is a flowchart showing steps that are performed by smoking device 200, in accordance with some applications of the present invention. Typically, users have different smoking preferences from each other and some users' preferences vary. Some users wish to smoke a full capsule during a relatively short period, while others may wish to puff only occasionally. For users who wish to smoke a full capsule during a relatively short period it is typically more appropriate to heat the smoking material to the vaporization temperature of the active agents for a predefined period of time, to enable instant and prolonged vaporization of the active agents. For users who wish to puff only occasionally it is typically more appropriate to heat the smoking material to the vaporization temperature of the active agents only when the user actually wishes to puff from the capsule, such as to preserve the active agents while allowing for delays between puffs. (It is noted that, in some cases, prolonged heating versus intermittent heating will also influence the nature of the vapors released from the smoking material (such as taste, intensity, amount of vapors, etc.), and respective users may have different preferences.

Therefore, for some applications, the control component receives an indication from the user indicating whether they wish to smoke the active agents in a first mode or a second mode. Typically, the first mode is suitable for users who wish to smoke a full capsule during a relatively short period, whereas the second mode is suitable for users who wish to puff occasionally. Typically, in response to receiving an indication that the user wishes to smoke the active agents in the first mode, the control component heats the smoking material to the vaporization temperature of the one or more active agents for a predefined period of time (e.g., a period of time of between 60 seconds and 600 seconds). Further typically, in response to receiving an indication that the user wishes to smoke the active agents in the second mode, the control component heats the smoking material to the vaporization temperature only while receiving an active input from the user that they wish for the smoking material to be heated. For some applications, the smoking device includes a heating button (e.g., button 204 shown in FIG. 26) configured to be pressed by the user. The user pressing the button for a short press (i.e., for a duration that is less than a threshold duration (e.g., a threshold duration of between 0 seconds and 2 seconds)), is interpreted by the control component as meaning that the user wishes to smoke in the first mode, and the user pressing the button for a long press (i.e., for more than the threshold duration), is interpreted by the control component to mean that the user wishes to smoke the active agents in the second mode. For some applications, in the second mode, the heating is turned off either immediately upon release of the button, or a after a short delay (e.g., a delay of between 0 seconds and 5 seconds). For some applications, the smoking device is configured such that during a smoking session, the user can switch from the first mode to the second mode by pressing the button for a long press (i.e., for more than the threshold duration), and/or from the second mode to the first mode by pressing the button for a short press (i.e., for less than the threshold duration).

For some applications, the control component is configured to preheat the smoking material to a temperature that is below the vaporization temperature of the one or more active agents, prior to receiving the indication from a user indicating whether they wish to smoke the active agents in a first mode or a second mode. For example, the control component is configured to preheat the smoking material to the temperature that is below the vaporization temperature of the one or more active agents automatically, in response to the capsule being inserted into the smoking device. Alternatively or additionally, the control component is configured to preheat the smoking material to the temperature that is below the vaporization temperature of the one or more active agents, in response to an input from the user (e.g., an initial push of button 204). For some applications, when operating in the second mode, the control component preheats the smoking material to the temperature that is below the vaporization temperature of the one or more active agents in between presses of the button by the user. Typically, preheating the smoking material to a temperature that is below the vaporization temperature of the one or more active agents allows the heating of the smoking material to the vaporization temperature to occur more quickly and/or more uniformly than if the smoking material is not preheated. Typically, the preheating does not release the active agents since the preheating is performed to a lower temperature than the vaporization temperature of the active agents. For some applications, the smoking device is configured to preheat the smoking material in the manner described in the present paragraph, even without being configured to perform both the first and second modes of heating.

Referring again to FIG. 34, some of the above-described steps are shown in the flowchart. For some applications, the smoking material is initially preheated. In response to the button being pressed, the heating is switched on. If the button is pressed for a long press, the heating continues so long as the button is still being pressed, whereas if the button is pressed for a short press, the heating in turned off after predefined delay of N seconds (e.g., a period of time of between 60 seconds and 600 seconds).

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus for use with a cylindrically-shaped capsule that contains a smoking material containing one or more active agents, the apparatus comprising:
a smoking device configured to:
receive the cylindrically-shaped capsule that contains the smoking material;
flatten at least part of a portion of the capsule that contains the smoking material; and
vaporize one or more of the active agents from within the smoking material by heating the smoking material while at least part of the portion of the capsule that contains the smoking material is a flattened configuration, wherein:
the smoking device comprises a coil that is configured to heat the smoking material by generating a magnetic field such as to heat the capsule via magnetic induction; and
the coil is configured to be flattened while at least part of the portion of the capsule that contains the smoking material is disposed within the coil.

2. The apparatus according to claim 1, wherein the smoking device comprises mechanical elements that are configured to flatten at least part of the portion of the capsule that contains the smoking material by applying mechanical pressure to the capsule.

3. The apparatus according to claim 1, wherein the smoking device comprises a control component configured to:
receive an indication from a user indicating whether they wish to smoke the active agents in a first mode or a second mode;
in response to receiving an indication that the user wishes to smoke the active agents in the first mode, heat the smoking material to a vaporization temperature of the one or more active agents for a predefined period of time; and
in response to receiving an indication that the user wishes to smoke the active agents in the second mode, only heat the smoking material to the vaporization temperature while receiving an active input from the user that they wish for the smoking material to be heated.

4. The apparatus according to claim 3, wherein the control component is configured to preheat the smoking material to a temperature that is below the vaporization temperature of the one or more active agents, prior to receiving the indication from the user indicating whether they wish to smoke the active agents in the first mode or the second mode.

5. The apparatus according to claim 1, wherein the smoking device comprises two or more electrodes that are configured to heat the smoking material by generating resistive heating within the capsule by driving a current through a portion of the capsule.

6. The apparatus according to claim 5, wherein the electrodes are configured to move axially along a length of the capsule.

7. The apparatus according to claim 5, wherein the smoking device comprises a mechanism configured to bring the electrodes into pressurized contact with the capsule, in order to enhance electrical contact between the electrodes and the capsule.

8. The apparatus according to claim 5, wherein the capsule comprises an elongate capsule, wherein during the heating of the smoking material, the smoking device is configured to house the capsule such that airflow through the capsule is substantially along a length of the elongate capsule, and wherein a first one of the electrodes is configured to drive a current toward a second one of the electrodes along a length of more than 5 mm in an axial direction along a length of the capsule.

9. The apparatus according to claim 8, wherein the first one of the electrodes is configured to drive the current toward the second one of the electrodes along a length of more than 15 mm in the axial direction along the length of the capsule.

10. The apparatus according to claim 5, wherein the smoking device is configured to receive a capsule that includes a metallic foil surrounding the smoking material, and the electrodes are configured to drive the current through the metallic foil.

11. The apparatus according to claim 10, wherein the smoking device is configured to receive a capsule that includes a metallic foil surrounding the smoking material and a paper covering that covers the metallic foil, and wherein the electrodes are needle shaped and are configured to make electrical contact with the metallic foil by piercing through the paper covering.

12. The apparatus according to claim 1, wherein the coil is shaped to define a non-circular cross-sectional shape even before part of the portion of the capsule that contains the smoking material is introduced to within the coil, and wherein the smoking device is configured to flatten the part of the portion of the capsule that contains the smoking material prior to the part of the portion of the capsule that contains the smoking material being introduced to within the coil.

13. The apparatus according to claim 1, wherein the smoking device is configured to receive a cylindrically-shaped elongate capsule having a length of between 15 mm and 150 mm.

14. The apparatus according to claim 13, wherein the smoking device is configured to receive a cylindrically-shaped elongate capsule having a length of between 50 mm and 90 mm.

15. The apparatus according to claim 1, wherein the smoking device is configured to flatten the at least part of the portion of the capsule that contains the smoking material such that the part of the portion of the capsule that contains the smoking material defines a cross-sectional shape having a ratio of more than 2:1 between a long side of the cross-sectional shape and a short side of the cross-sectional shape.

16. The apparatus according to claim 15, wherein the smoking device is configured to flatten the at least part of the portion of the capsule that contains the smoking material such that the part of the portion of the capsule that contains the smoking material defines a cross-sectional shape having a ratio of more than 3:1 between a long side of the cross-sectional shape and a short side of the cross-sectional shape.

17. The apparatus according to claim 16, wherein the smoking device is configured to flatten the at least part of the portion of the capsule that contains the smoking material such that the part of the portion of the capsule that contains the smoking material defines a cross-sectional shape having a ratio of more than 4:1 between a long side of the cross-sectional shape and a short side of the cross-sectional shape.

18. The apparatus according to claim 17, wherein the smoking device is configured to flatten the at least part of the portion of the capsule that contains the smoking material such that the part of the portion of the capsule that contains the smoking material defines a cross-sectional shape having a ratio of more than 6:1 between a long side of the cross-sectional shape and a short side of the cross-sectional shape.

* * * * *